(12) United States Patent
Harris et al.

(10) Patent No.: US 8,575,121 B2
(45) Date of Patent: Nov. 5, 2013

(54) THERAPEUTIC APPLICATIONS OF P53 ISOFORMS IN REGENERATIVE MEDICINE, AGING AND CANCER

(75) Inventors: Curtis C. Harris, Bethesda, MD (US); Kaori Fujita, Bethesda, MD (US); Izumi Horikawa, Bethesda, MD (US); Borivoj Vojtesek, Brno (CZ); Jean-Christophe Bourdon, Dundee (GB); David P. Lane, Dundee (GB)

(73) Assignees: The United States of America as represented by the Secetary of the Department of Health and Human Services, Washington, DC (US); The University of Dundee, Dundee, Scotland (GB); Masaryk Memorial Cancer Institute, Brno (CZ)

( * ) Notice: Subject to any disclaimer, the term of this patent is extended or adjusted under 35 U.S.C. 154(b) by 163 days.

(21) Appl. No.: 12/742,250

(22) PCT Filed: Oct. 21, 2008

(86) PCT No.: PCT/US2008/080648
§ 371 (c)(1),
(2), (4) Date: Sep. 29, 2010

(87) PCT Pub. No.: WO2009/064590
PCT Pub. Date: May 22, 2009

(65) Prior Publication Data
US 2011/0243968 A1    Oct. 6, 2011

Related U.S. Application Data

(60) Provisional application No. 60/987,340, filed on Nov. 12, 2007.

(51) Int. Cl.
*C12N 15/11* (2006.01)
(52) U.S. Cl.
USPC ...................................................... 514/44 A
(58) Field of Classification Search
USPC ...................................................... 514/44 A
See application file for complete search history.

(56) References Cited

U.S. PATENT DOCUMENTS 6,506,559 B1 *  1/2003  Fire et al. ..................... 435/6.16

FOREIGN PATENT DOCUMENTS

| WO | WO94/16066 | * | 7/1994 |
| WO | WO 2009/029054 | | 3/2009 |

OTHER PUBLICATIONS

International Search Report dated Jul. 9, 2009 received in related International Application No. PCT/US2008/080648, filed Oct. 21, 2008.
Antoniades et al., "p53 expression during normal tissue regeneration in response to acute cutaneous injury in swine," 1994, J. Clin. Invest., 93(5), 2206-2214.
Arnada-Anzaldo et al., "Reassessing the role of p53 in cancer and ageing from an evolutionary perspective," 2007, Mech. Ageing Def., 12(4), 293-302.
Boomer et al., "p53-mediated activation of miRNA34 candidate tumor-suppressor genes," 2007, Current Biology, vol. 17(5), 1298-1307.
Bourdon et al., "p53 isoforms can regulate p53 transcriptional activity," 2005, Genes and Dev., 19, 2122-2137.
Chan et al., "The p53 Isoform Δp53 Lacks Intrinsic Transcriptional Activity and Reveals the Critical Role of Nuclear," 2007, Cancer Res., 67(5), 1959-1969.
Chen et al., "Loss of function of *def* selectively up-regulates Δ113p53 expression to arrest expanion growth of digestive organs in zebrafish," 2005, Genes & Development, 19, 2900-2911.
Gimeno et al., "Monitoring the effect of gene silencing by RNA interference in human CD34$^+$ cells injected into newborn RAG2$^{-/-}$ γC$^{-/-}$ mice: functional inactivation of p53 in developing T cells," 2004, Blood, 104, 3886-3893.
Maier et al., "Modulation of mammalian life span by the short isoform of p53," 2004, Genes & Development, 18, 306-319.
Murray-Zmijewski et al., "p53/p63/p73 isoforms: an orchestra of isoforms to harmonise cell differentiation and response to stress," 2006, Cell Death and Differentiation, 13, 962-972.
Papazoglu et al., "p53: at the crossroad between cancer and ageing," 2007, Journal of Pathology, 211, 124-133.
Raver-Shapira et al, "Tiny actors, great roles: microRNAs in p53's service," 2007, Cell Cycle, 6(21), 2656-2661.
Tarasov et al., "Differential regulation of microRNAs by p53 revealed by massively parallel sequencing: miR-34a is a p53 target that induces apoptosis and G1-arrest," 2007, Cell Cycle, vol. 6, No. 13, 1586-1593.
Tazawa et al., "Tumor-suppressive *miR-34a* induces senescence-like growth arrest through modulation of the E2F pathway in human colon cancer cells," 2007, PNAS, 104, 15472-15477.
Tyner et al., "p53 mutant mice that display early ageing-associated phenotypes," 2002, Nature, 415(6867), 45-53.

* cited by examiner

*Primary Examiner* — Brian Whiteman
(74) *Attorney, Agent, or Firm* — Kilpatrick Townsend & Stockton LLP

(57) ABSTRACT

The present invention provides methods and compositions for modulating cell senescence and cell proliferation using isoforms of the p53 tumor suppressor protein. The methods and compositions of the invention find use in inhibiting cancer cell growth or in generating populations of cells for tissue regeneration through the modulation of cell senescence and proliferation.

8 Claims, 71 Drawing Sheets

*Fig. 1 (Cont.)*
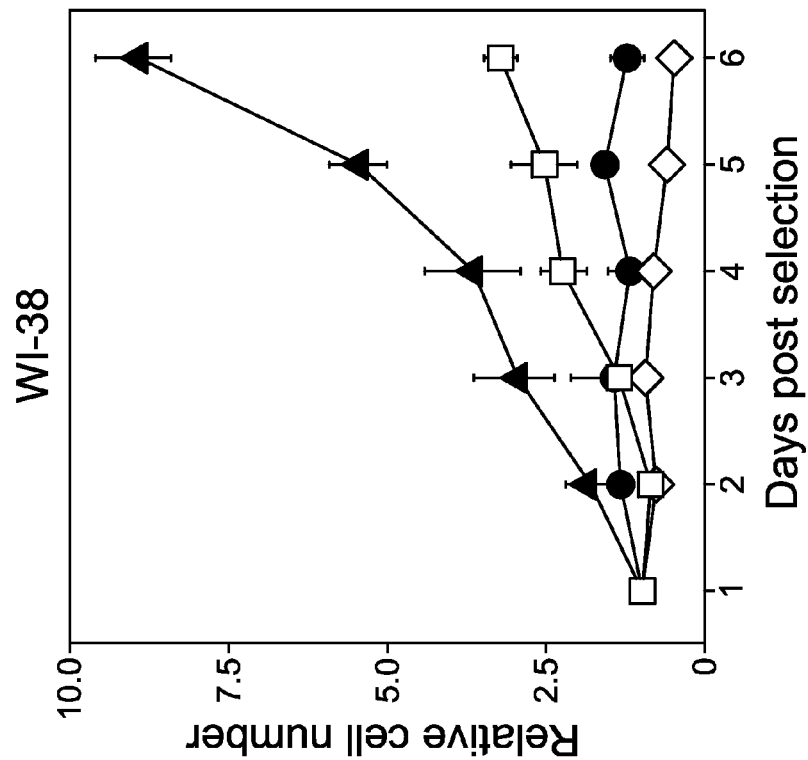
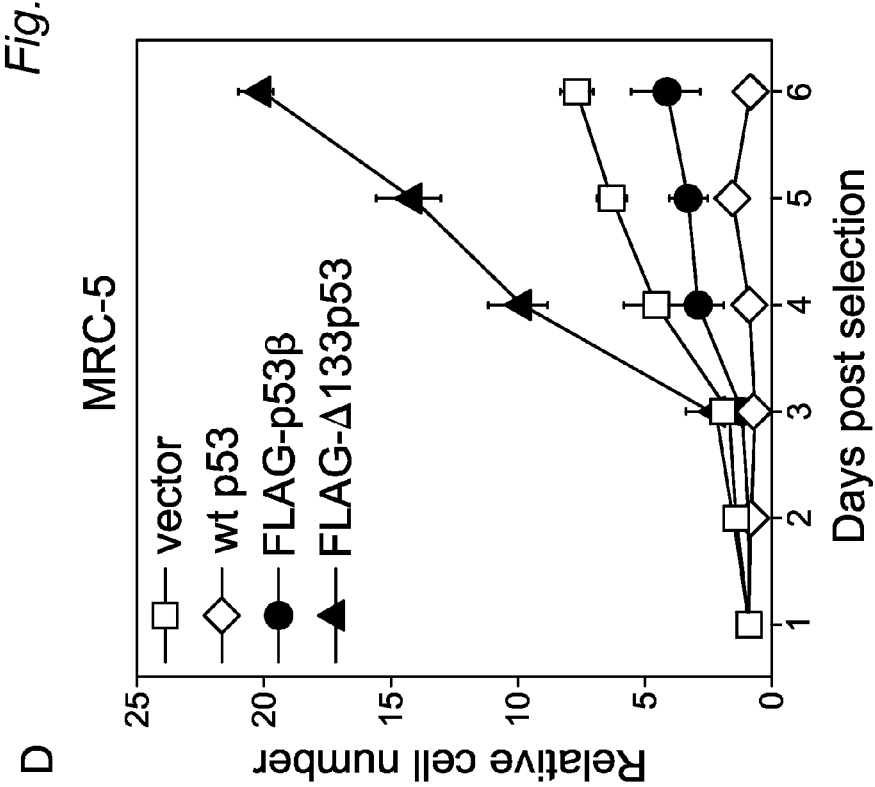

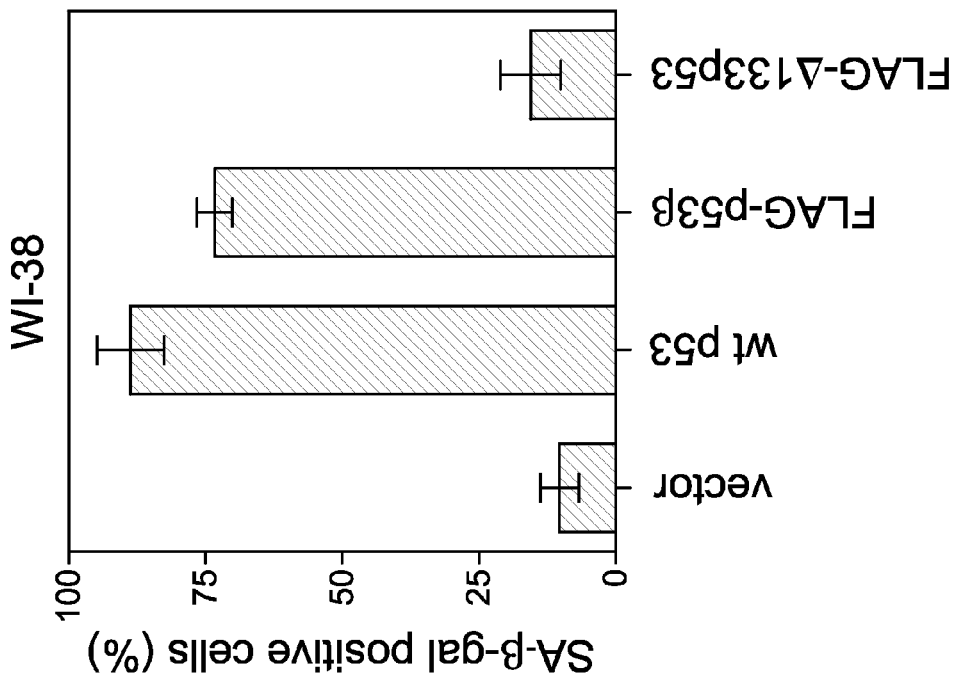
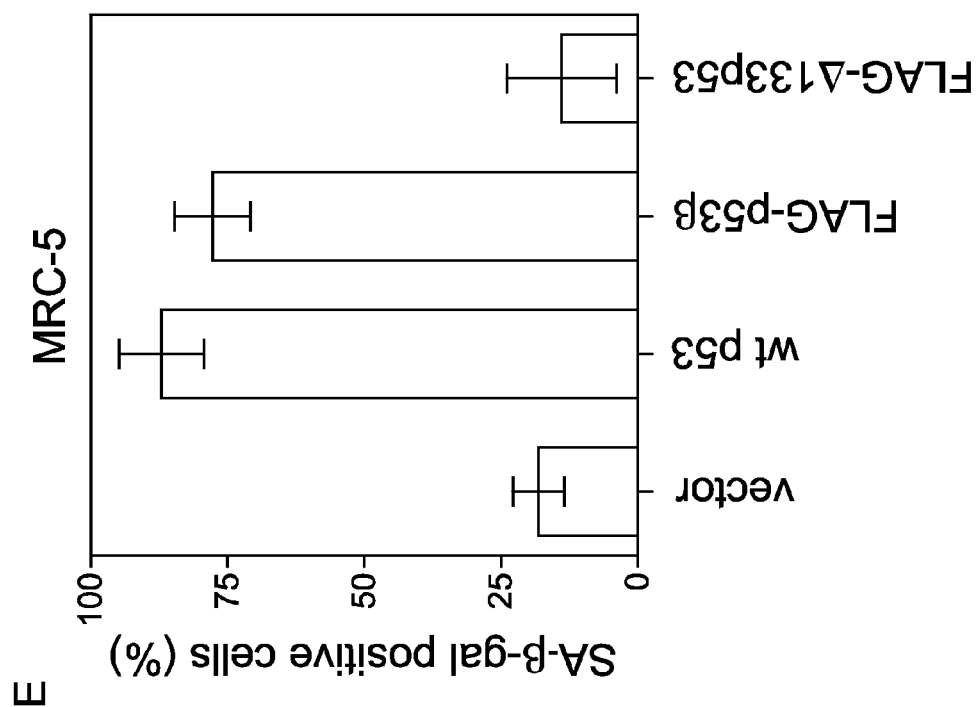
Fig. 1 (Cont.)

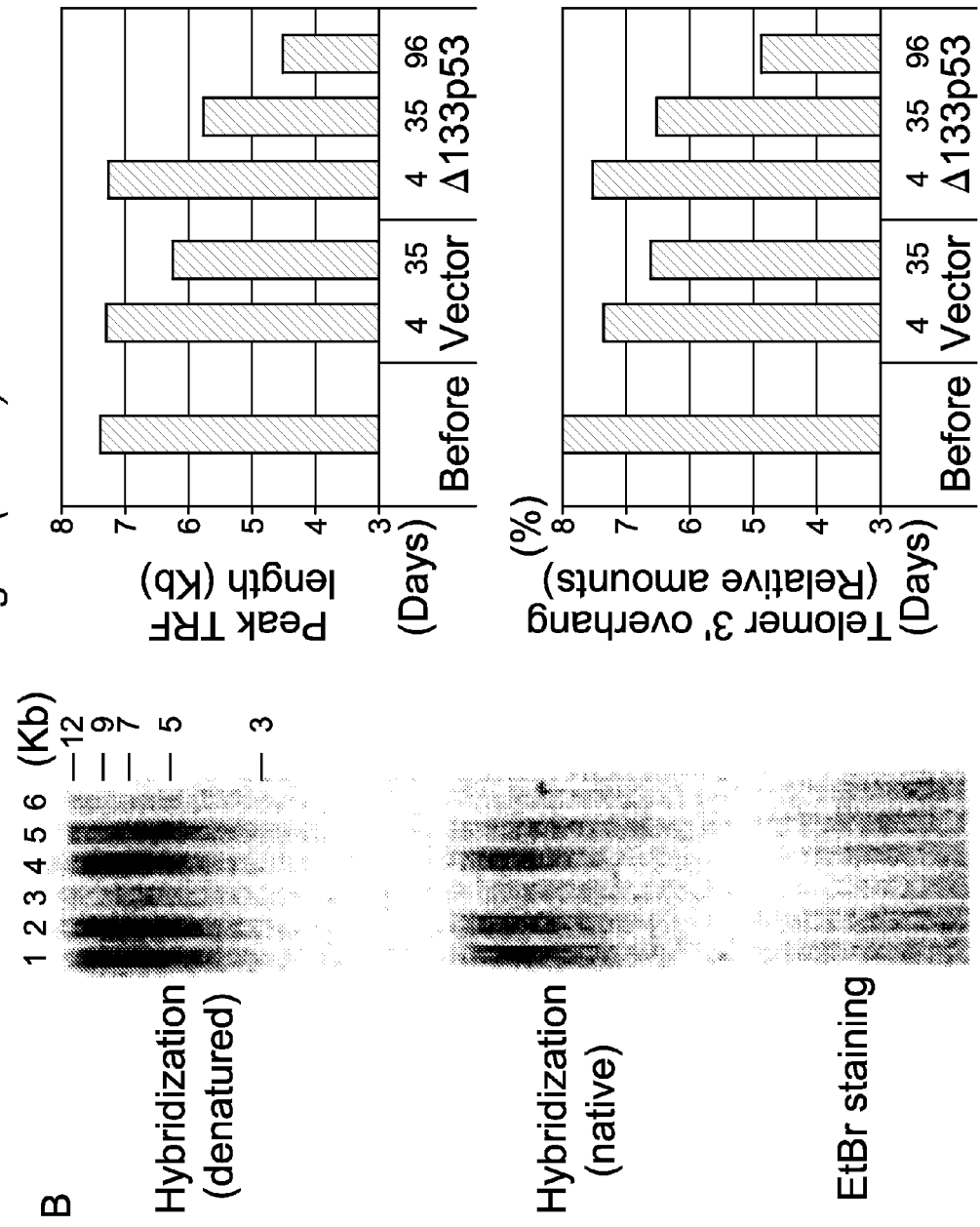

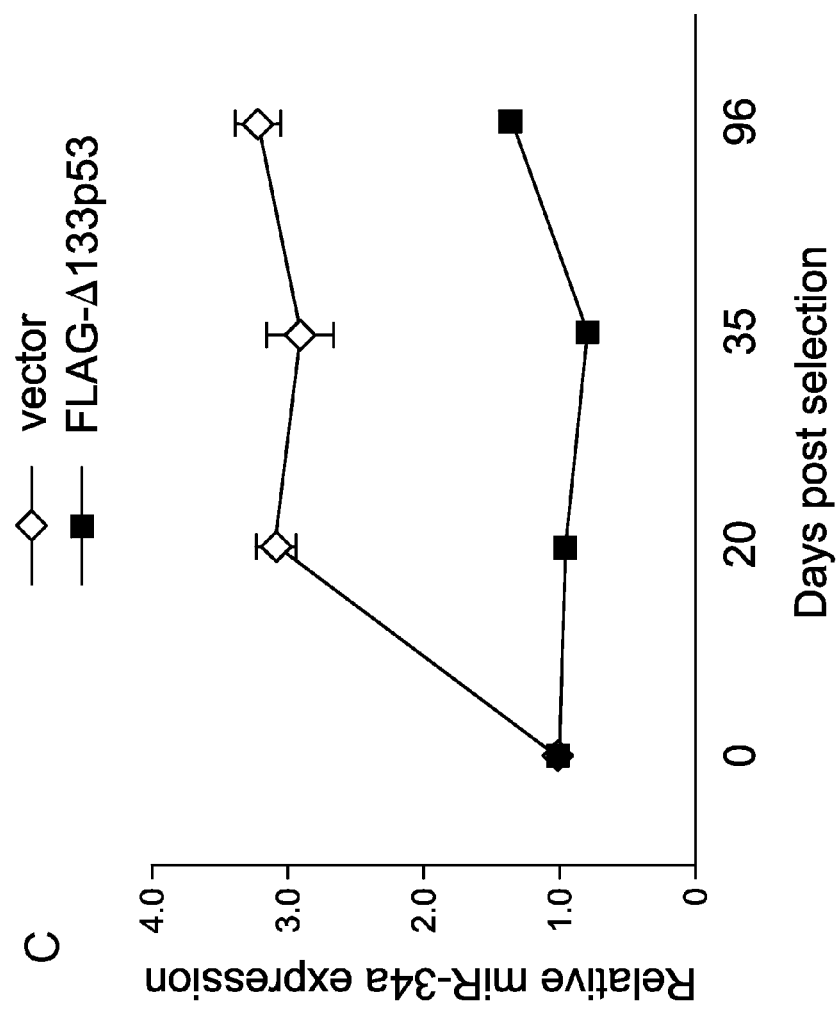

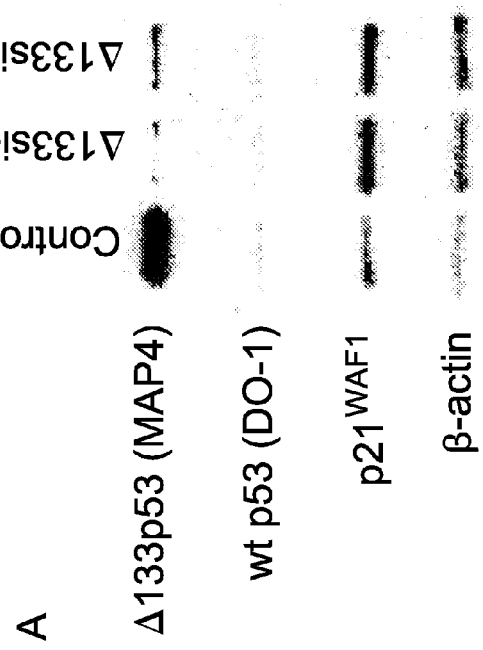
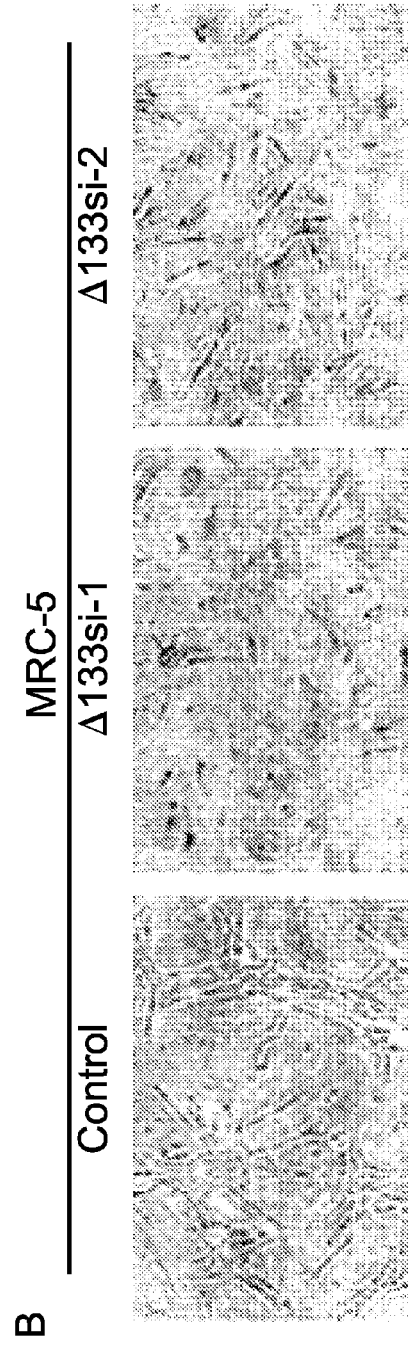
Figs. 3

Fig. 7
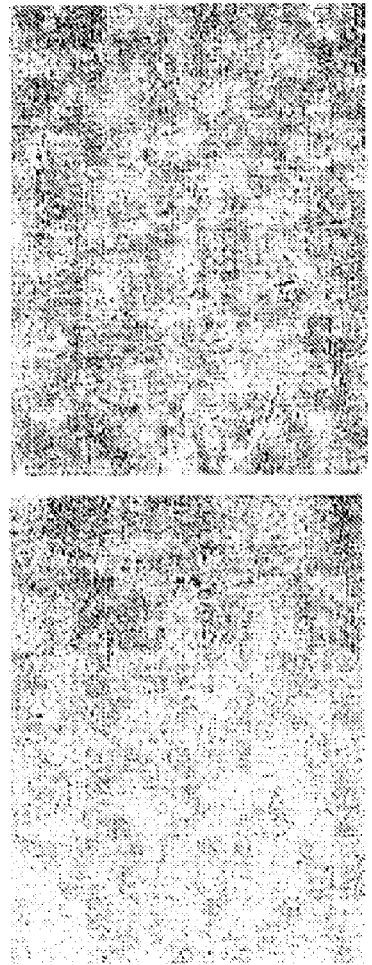
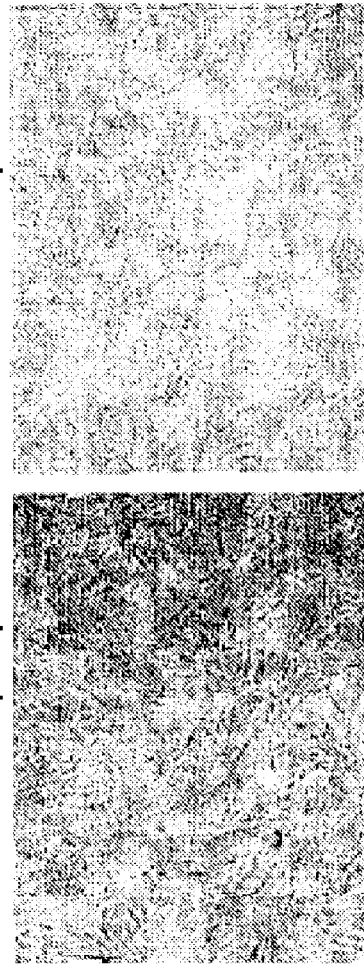

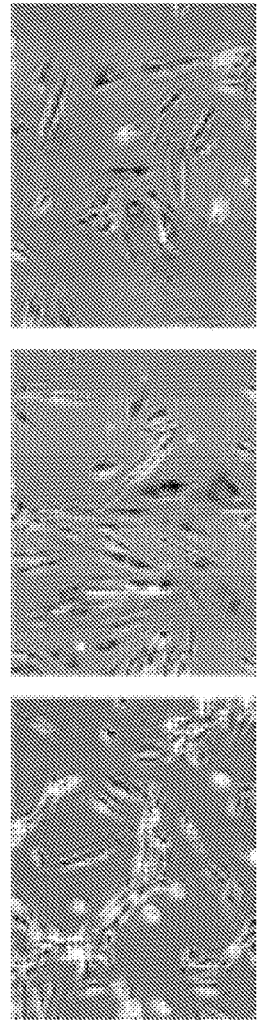
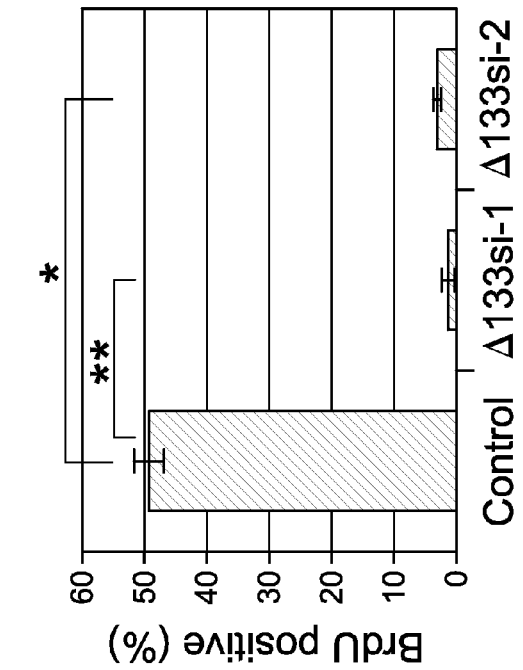
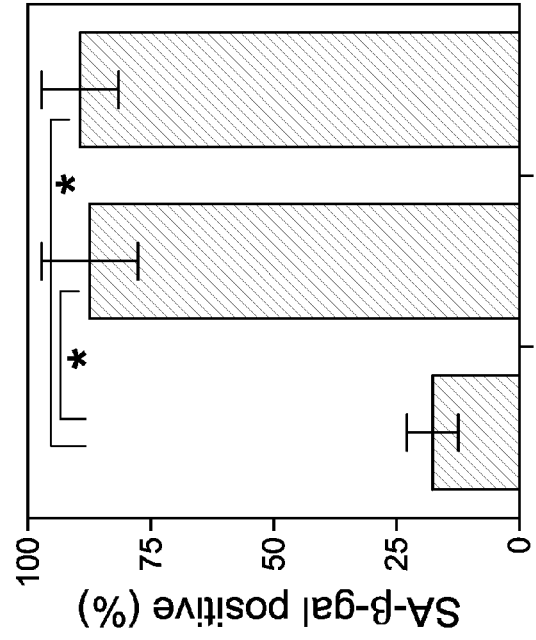
Figs. 15 (Cont.)

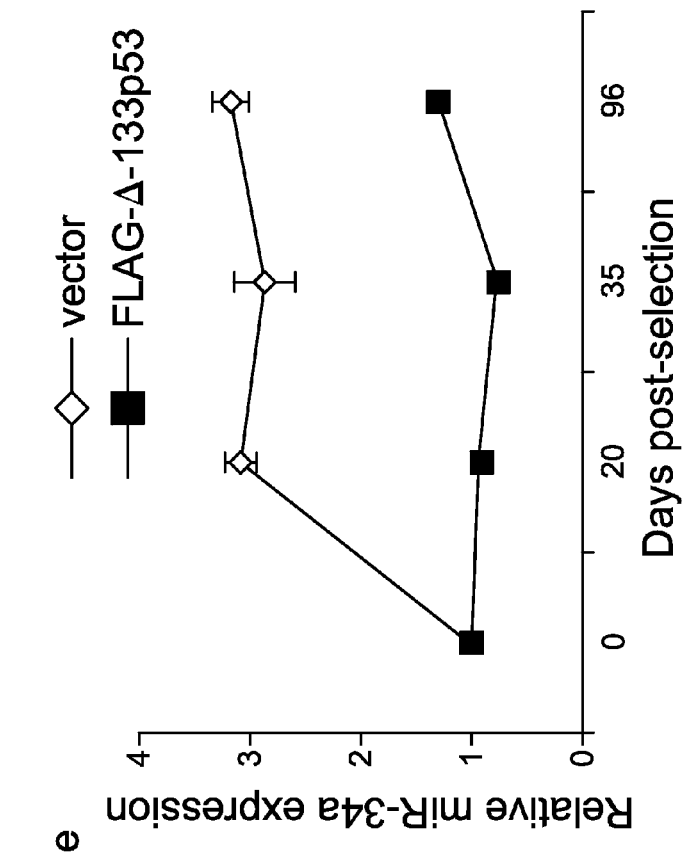
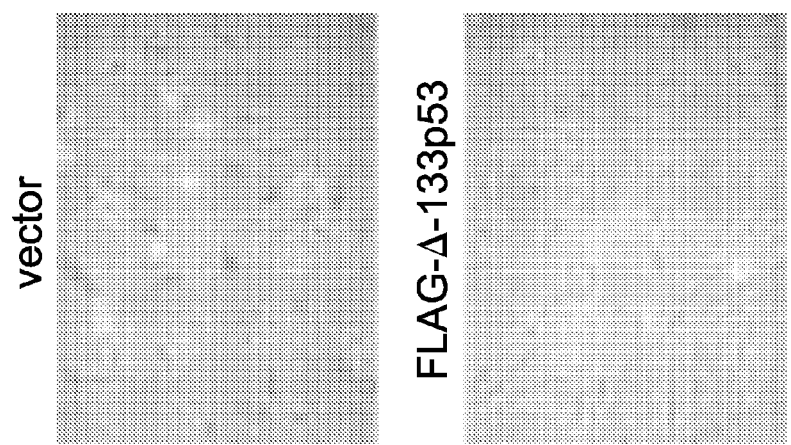
Figs. 16 (Cont.)

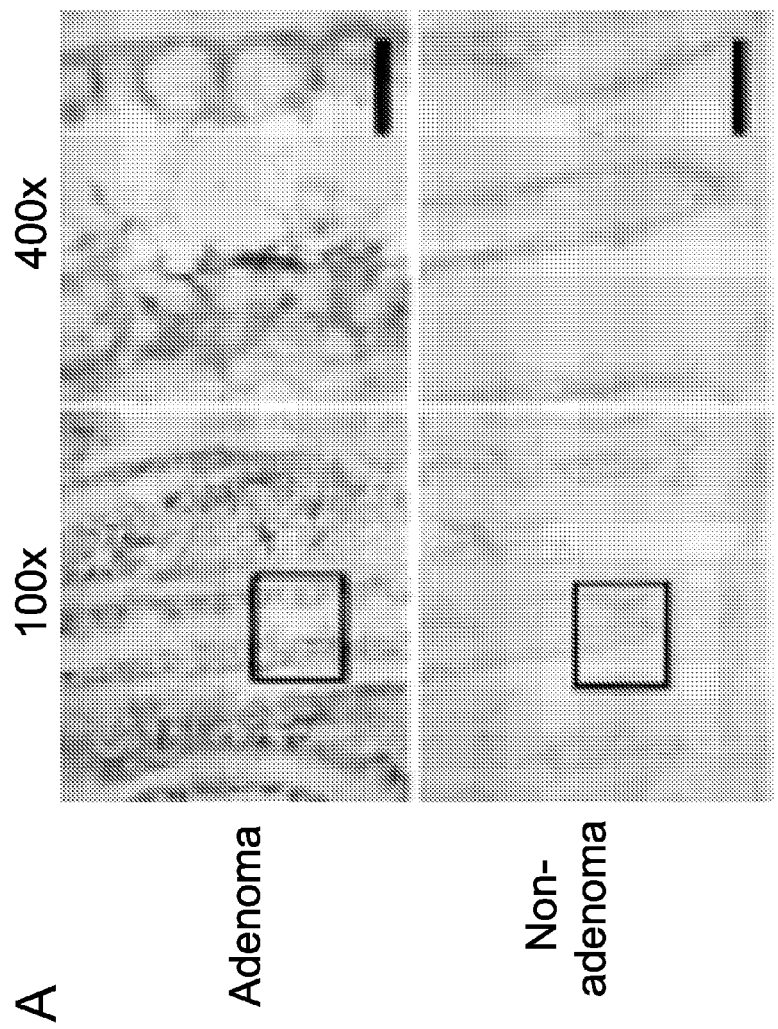

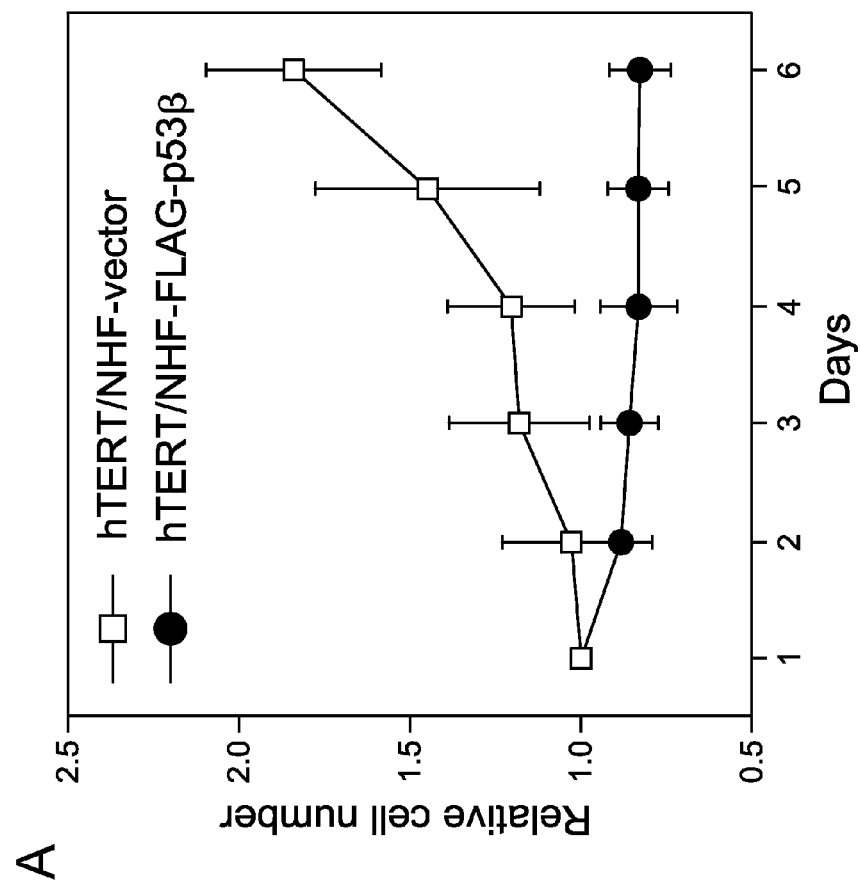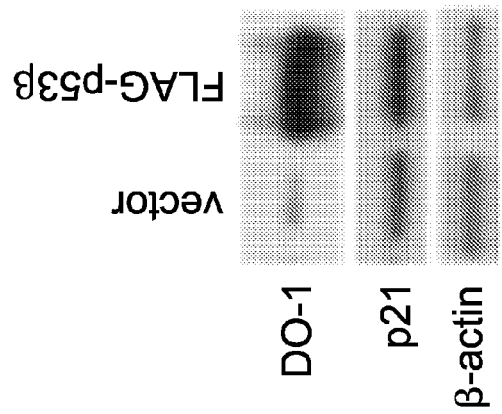
Fig. 26

*Fig. 26 (Cont.)*
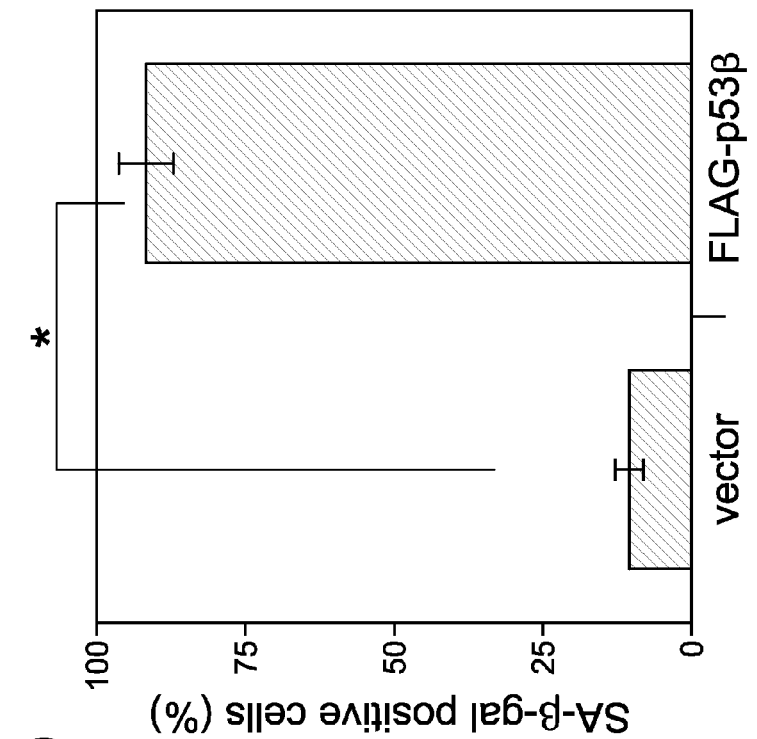
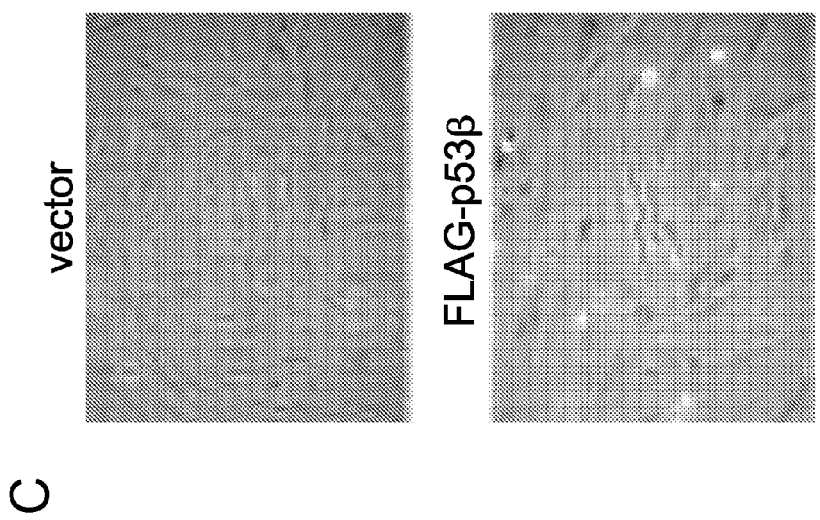

mRNA expression analysis of p53 isoforms in human fibroblasts

*Fig. 36*

FACS (Fluorescence-activated cell sorting) of human CD8+ T lymphocytes

A

| Donor | CD28+/CD57- (%) | CD28+/CD57+ (%) | CD28-/CD57- (%) | CD28-/CD57+ (%) |
|---|---|---|---|---|
| Female, 60 yrs | 42.1 | 8.3 | 10.7 | 38.9 |
| Male, 65 yrs | 37.9 | 4.2 | 8.8 | 49 |
| Male, 50 yrs | 19 | 4.7 | 13.2 | 63.2 |

Δ133p53 and p53β expression in human CD8+ T lymphocytes

Δ133p53 is not subject to proteasomal degradation

SEQUENCE LISTING

<160> NUMBER OF SEQ ID NOS: 18

<210> SEQ ID NO 1
<211> LENGTH: 25
<212> TYPE: RNA
<213> ORGANISM: Artificial Sequence
<220> FEATURE:
<223> OTHER INFORMATION: Description of Artificial Sequence:synthetic
    delta133si-1 stealth siRNA duplex oligonucleotide
    targeting delta133p53 mRNA

<400> SEQUENCE: 1
uguucacuug ugcccugacu uucaa                                              25

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule:
    synthetic delta133si-2 standard siRNA duplex oligonucleotide
    targeting delta133p53 mRNA
<220> FEATURE:
<223> OTHER INFORMATION: Description of Artificial Sequence:synthetic
    delta133si-2 standard siRNA duplex oligonucleotide
    targeting delta133p53 mRNA

<400> SEQUENCE: 2
cuugugcccu gacuuucaat t                                                  21

<210> SEQ ID NO 3
<211> LENGTH: 23
<212> TYPE: RNA
<213> ORGANISM: Artificial Sequence
<220> FEATURE:
<223> OTHER INFORMATION: Description of Artificial Sequence:synthetic
    antisense 2'-O-methyl oligonucleotide for
    inhibiting miR-34a
<220> FEATURE:
<221> NAME/KEY: modified_base
<222> LOCATION: (1)..(23)
<223> OTHER INFORMATION: 2'-O-methyl nucleotides

<400> SEQUENCE: 3
aacaaccagc uaagacacug cca                                                23

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence:synthetic
    antisense 2'-O-methyl oligonucleotide
    complementary to enhanced green fluorescent
    protein (EGFP) control
<220> FEATURE:
<221> NAME/KEY: modified_base
<222> LOCATION: (1)..(21)
<223> OTHER INFORMATION: 2'-O-methyl nucleotides

<400> SEQUENCE: 4
aaggcaagcu gacccugaag u                                                  21

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:synthetic

```
        32-P-labeled oligonucleotide in-gel hybridization
        probe

<400> SEQUENCE: 5
ccctaaccct aaccctaacc ctaa                                            24

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:synthetic
        RT-PCR primer to amplify wild type p53

<400> SEQUENCE: 6
ctcaccatca tcacactgga a                                               21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:synthetic
        RT-PCR primer to amplify wild type p53

<400> SEQUENCE: 7
tcattcagct ctcggaacat c                                               21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:synthetic
        RT-PCR primer specifically detecting alternative
        splicing for p53beta

<400> SEQUENCE: 8
ctttgaggtg cgtgtttgtg c                                               21

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:synthetic
        RT-PCR primer specifically detecting alternative
        splicing for p53beta

<400> SEQUENCE: 9
ttgaaagctg gtctggtcct ga                                              22

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:synthetic
        RT-PCR primer specificalyy amplifying delta133p53
        mRNA transcribed from the promoter in intron 4

<400> SEQUENCE: 10
tgggttgcag gaggtgctta c                                               21

<210> SEQ ID NO 11
<211> LENGTH: 22
<212> TYPE: DNA
<213> ORGANISM: Artificial Sequence
```

-continued

```
<220> FEATURE:
<223> OTHER INFORMATION: Description of Artificial Sequence:synthetic
      RT-PCR primer specificalyy amplifying delta133p53
      mRNA transcribed from the promoter in intron 4

<400> SEQUENCE: 11
ccactcggat aagatgctga gg                                              22

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence:synthetic
      C-terminal sequence of delta133p53 and p53beta
      isoforms

<400> SEQUENCE: 12

Asp Gln Thr Ser Phe Gln Lys Glu Asn Cys
  1               5                  10

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence:synthetic
      Multiple Antigenic Peptide peptide for raising
      antibody specifically recognizing delta133p53

<400> SEQUENCE: 13

Met Phe Cys Gln Leu Ala Lys Thr Cys
  1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence:synthetic
      Multiple Antigenic Peptide peptide for raising
      antibody specifically recognizing delta133p53

<400> SEQUENCE: 14

Phe Cys Gln Leu Ala Lys Thr Cys Pro
  1               5

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:synthetic
      quantitative PCR primer for plasminogen activator
      inhibitor-1 (PAI-1) mRNA

<400> SEQUENCE: 15
ctcctggttc tgcccaagt                                                  19

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:synthetic
      quantitative PCR primer for plasminogen activator
      inhibitor-1 (PAI-1) mRNA

<400> SEQUENCE: 16
```

-continued

```
caggttctct aggggcttcc                                              20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence:synthetic
      quantitative PCR primer for beta-2 microglobulin
      internal control mRNA

<400> SEQUENCE: 17
ttctggcctg gaggctatc                                               19

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence:synthetic
      quantitative PCR primer for beta-2 microglobulin
      internal control mRNA

<400> SEQUENCE: 18
tcaggaaatt tgactttcca ttc                                          23
```

THERAPEUTIC APPLICATIONS OF P53 ISOFORMS IN REGENERATIVE MEDICINE, AGING AND CANCER

CROSS-REFERENCES TO RELATED APPLICATIONS

This application is the U.S. National Stage entry of International Application No. PCT/US2008/080648, filed Oct. 21, 2008, which claims priority to U.S. Ser. No. 60/987,340, filed Nov. 12, 2007, the contents of which are hereby incorporated by reference in the entirety for all purposes.

BACKGROUND OF THE INVENTION

Cellular senescence was first described by Hayflick and Moorhead (1961) when they observed that normal human fibroblasts entered a state of irreversible growth arrest after serial passage in vitro. In contrast, cancer cells did not enter this growth arrested state and proliferated indefinitely. The maximum number of cell divisions that a cell can undergo, termed the Hayflick limit, varies from cell type to cell type and organism. In fibroblasts, this number is about 50 divisions, after which cell division ceases.

The process of cellular senescence can be triggered by multiple mechanisms, including telomere shortening, derepression of the INK4a/ARF locus, and DNA damage. As discussed below, all three of these mechanisms implicate the function of the tumor suppressor protein p53.

Telomere shortening provides a mechanism capable of counting cell divisions. Telomeres consist of repetitive DNA elements at the end of linear chromosomes that protect chromosome ends from degradation and recombination. Due to the intrinsic inability of the DNA replication machinery to copy the ends of linear molecules, telomeres become progressively shorter with each round of replication, thus providing a counting mechanism for keeping track of the number of cell divisions that have occurred in a population of cells. As increasing numbers of cell division occur, the telomeres reach a critically short length, which present as double-stranded DNA breaks that activate the p53 tumor suppressor protein resulting in telomere-initiated senescence or apoptosis.

Derepression of the INK4a/ARF locus can also serve as a cell division counting mechanism. The INK4a/ARF locus is normally expressed at very low levels in most tissues of young organisms but progressively becomes derepressed with aging. Thus, a cell division counting mechanism is provided by a progressively increased level of repression of the INK4a/ARF locus. The p16INK4a protein functions as an inhibitor of cyclin-dependent kinases CDK4 and CDK6, thus providing a G1 cell cycle arrest. ARF regulates p53 stability through inactivation of the p53-degrading ubiquitin ligase MDM2.

The accumulation of DNA damage over time can also serve as a trigger for cell senescence. As an organism ages, increases in DNA mutations, DNA oxidation, and chromosome losses are observed. These observations have prompted investigators to consider DNA damage as contributing to cellular senescence and organismal aging. As a guardian of cell cycle progression after DNA damage, p53 plays a role here too, as p53 induces the expression of the cell cycle inhibitor p21 when a cell has undergone DNA damage.

Given the direct impact that cell senescence has on cell division and cell cycle arrest, one would expect this process to play a central role in such diverse processes as aging, cancer, and tissue regeneration. The present invention provides methods and compositions for manipulating these diverse processes through the modulation of cell senescence.

BRIEF SUMMARY OF THE INVENTION

The present invention is based in part on the discovery that the switching of expression from one p53 isoform ($\Delta$133p53) to another (p53$\beta$) results in replicative cellular senescence in normal human fibroblasts. Specifically, the present inventors have discovered that p53$\beta$ and $\Delta$133p53 promotes and inhibits, respectively, cellular senescence when overexpressed. siRNA-mediated knockdown of endogenous $\Delta$133p53 induced cellular senescence. $\Delta$133p53 counteracted wild-type (wt) p53 to repress its transcriptional targets ($p21^{WAF1}$ and miR-34a) and inhibit wt p53-mediated degradation of TRF2, allowing cell proliferation beyond the normal senescence setpoint of telomeres. Accordingly, the present invention takes advantage of a novel telomere-mediated mechanism by which p53 regulates cellular senescence through inhibition of p53 activity by its own natural isoforms.

Accordingly, in one aspect, the present invention provides a method of promoting senescence in a cell by contacting the cell with an agent that inhibits the function or expression of $\Delta$133p53, thereby promoting cell senescence. The invention therefore also provides a use of such an inhibitory agent of $\Delta$133p53 for manufacturing a medicament for treating a disease in which cell senescence is inadequate.

In another aspect, the present invention provides a method of treating or preventing cancer cell growth by promoting cell senescence by contacting the cancer cell with an agent that inhibits the function or expression of $\Delta$133p53, thereby inhibiting cancer cell growth. Similarly, this invention provides a method for treating cancer by contacting cancer cells with an agent that inhibits the function or expression of $\Delta$133p53 in order to promote cancer cell senescence and therefore treat cancer. The invention therefore provides a use of such an inhibitory agent of $\Delta$133p53 for manufacturing a medicament for treating or preventing a disease or condition involving undesirable cellular proliferation such as various types of cancer.

In this invention, an inhibitory agent of $\Delta$133p53 may be an antisense oligonucleotide, an siRNA (e.g., shRNA), a ribozyme, or a small organic molecule. Preferably, such an inhibitor is effective specifically for this particular isoform of p53 protein and not other isoforms.

In another aspect, the present invention provides a method of extending the replicative lifespan of a cell by inhibiting cell senescence by contacting the cell with an agent that activates the function or expression of $\Delta$133p53, thereby inhibiting cell senescence and extending the replicative lifespan of the cell. The invention therefore provides a use of an activator of $\Delta$133p53 for manufacturing a medicament for treating a condition where cell replicative lifespan is inadequate.

In another aspect, the present invention provides a method of generating a population of cells for tissue regeneration by inhibiting cell senescence by: (a) contacting a cell suitable for tissue regeneration that has a finite number of cell divisions with an agent that activates the function or expression of $\Delta$133p53, thereby inhibiting cell senescence and increasing the number of cell divisions undergone by the cell, and (b) culturing the cell to obtain a cell population, thereby generating a population of cells for tissue regeneration. In some aspects of this embodiment, the agent comprises a nucleic acid for the overexpression of $\Delta$133p53, such as a polynucleotide sequence (e.g., a DNA sequence) encoding $\Delta$133p53 or an expression cassette capable of overexpressing the protein. The method for producing cell populations for tissue regeneration can be useful for treating or preventing degenerative diseases including various age-related conditions such as osteoporosis, osteoarthritis, macular degeneration, and atherosclerosis.

In another aspect, the present invention provides a method of promoting senescence in a cell by contacting the cell with an agent that activates the function or expression of p53β, thereby promoting cell senescence. In some embodiments, the agent comprises a nucleic acid encoding p53β, such as a polynucleotide sequence (e.g., a DNA sequence) or expression cassette encoding and capable of overexpressing p53β protein.

In another aspect, the present invention provides a method of treating or preventing cancer cell growth by promoting cell senescence by contacting the cancer cell with an agent that activates the function or expression of p53β, thereby inhibiting cancer cell growth. In some embodiments, the agent comprises a nucleic acid encoding p53β, such as a polynucleotide sequence (e.g., DNA) or expression cassette encoding and capable of overexpressing p53β protein.

In another aspect, the present invention provides a method of extending the replicative lifespan of a cell by inhibiting cell senescence, the method comprising the step of contacting the cell with an agent that inhibits the function or expression of p53β, thereby inhibiting cell senescence and extending the replicative lifespan of the cell. Similarly, the invention provides a method of preventing or treating a degenerative disease by inhibiting cell senescence. Degenerative diseases include various age-related conditions such as osteoporosis, osteoarthritis, macular degeneration, and atherosclerosis. For instance, the method includes the step of contacting cells or tissues that are susceptible of the degenerative disease or involved in the disease with an agent that inhibits the function or expression of p53β, therefore inhibits cell senescence and prevents or treats the degenerative disease.

In another aspect, the present invention provides a method of extending the replicative lifespan of a cell by inhibiting cell senescence by way of contacting the cell with an agent that inhibits the function or expression of miR-34a, thereby inhibiting cell senescence and extending the replicative lifespan of the cell. An exemplary agent useful for this purpose is an antisense oligonucleotide that specifically inactivates miR-34a.

In another aspect, this invention provides a method for enhancing or restoring immune functions by extending T cell lifespan. The method includes the step of contacting the T cell with an agent that activates the function or expression of Δ133p53, thereby extending the lifespan of the T cell and enhancing or restoring immune functions. The agent may comprise a polynucleotide sequence encoding Δ133p53, or comprise an expression cassette comprising a polynucleotide sequence encoding Δ133p53. In contrast, the invention also provides a method for enhancing or restoring immune functions by extending T cell lifespan by the means of contacting the T cell with an agent that inhibits the function or expression of p53β. Such an agent may be an siRNA, e.g., an shRNA, or a ribozyme. Furthermore, a method is provided for enhancing or restoring immune functions by extending T cell lifespan, the method comprising the step of contacting the T cell with an agent that inhibits the function or expression of miR-34a (such as an antisense oligonucleotide capable of inactivating miR-34a), thereby extending the lifespan of the T cell and enhancing or restoring immune functions.

In another aspect, the present invention provides a method of generating a population of cells for tissue regeneration by inhibiting cell senescence by: (a) contacting a cell suitable for tissue regeneration that has a finite number of cell divisions with an agent that inhibits the function or expression of p53β, thereby inhibiting cell senescence and increasing the number of cell divisions undergone by the cell, and (b) culturing the cell to obtain a cell population, thereby generating a population of cells for tissue regeneration.

In this invention, an inhibitory agent of p53β may be an antisense oligonucleotide, an siRNA (e.g., shRNA), a ribozyme, or a small organic molecule. Preferably, such an inhibitor is effective specifically to one isoform of the p53 protein and not to other isoforms.

In yet another aspect, the present invention provides a composition for promoting cell senescence comprising an siRNA directed to Δ133p53. In some cases, the siRNA is an shRNA. In an aspect of this embodiment, the siRNA comprises or consists of the sequence 5'-UGU UCA CUU GUG CCC UGA CUU UCA A-3' (SEQ ID NO:1) or 5'-CUU GUG CCC UGA CUU UCA A[dT][dT]-3' (SEQ ID NO:2). Optionally, a physiologically acceptable excipient is also present in this composition. In one example, this composition may be used for promoting senescence and inhibiting cellular proliferation by suppressing Δ133p53 activity, and therefore for use in treating conditions relevant to undesired cell proliferation, such as various types of cancer.

In another aspect, the present invention provides a method for identifying a compound that modulates cell senescence via its effect on Δ133p53 or p53β. In general, the method includes these steps: (a) contacting a candidate compound with a sample that comprises Δ133p53 or p53β, and (b) determining the functional effect of the compound (such as increased or decreased cell proliferation, cell cycle arrest, or apoptosis), based on which one may determine whether the compound is a modulator (e.g., an activator or inhibitor) of the respective p53 isoform. For instance, increased cell proliferation would indicate a test compound's role as a suppressor of senescence; whereas decreased cell proliferation, cell cycle arrest, or increased apoptosis would indicate a test compound's role as a promoter of the senescence. Accordingly, the identified modulator may be useful for preventing or treating cancer, or for extending a cell's replicative lifespan, depending on the specific effect of the modulator on Δ133p53 or p53ß and therefore on senescence. A candidate compound can be of any chemical nature: a small molecule or a macromolecule such as protein, lipid, polysaccharide, polynucleotide, etc., synthetic or naturally occurring.

In various aspects of this invention, the agent useful for suppressing the effects of a p53 isoform by inhibiting or inactivating the expression or function of the isoform can be an antisense oligonucleotide, an siRNA (such as a shRNA), a ribozyme, or a small organic molecule. In further aspects, the cell whose growth is to be suppressed can be a cancer cell. In some aspects of the above embodiments, the agent useful for enhancing the effects of a p53 isoform comprises a DNA for the overexpression of Δ133p53 or p53β.

BRIEF DESCRIPTION OF THE DRAWINGS

FIG. 7. Senescence-associated (SA)-β-galactosidase (gal) staining of MRC-5 fibroblasts overexpressing wt p53, FLAG-tagged p53β and FLAG-tagged Δ133p53. MRC-5 with control vector is also shown.

FIG. 26. p53β overexpression induces cellular senescence in human fibroblasts with ectopically expressed telomerase. a, Effects of p53β on cell proliferation. hTERT/NHF cells (Sengupta et al. *EMBO J.* 22, 1210-1222 (2003)) were transduced with the retroviral vector driving FLAG-tagged p53β or control vector (a zeocin-resistant version). Cell proliferation assay was carried out as in FIG. 16a. b, Upregulation of p21$^{WAF1}$ by p53β. overexpression in hTERT/NHF cells. c, Representative pictures of SA-β-gal staining. d, Summary of SA-β-gal staining. The data were mean±s.d. from three independent experiments. *, p<0.01.

DETAILED DESCRIPTION OF THE INVENTION

I. Introduction

Figure 1:
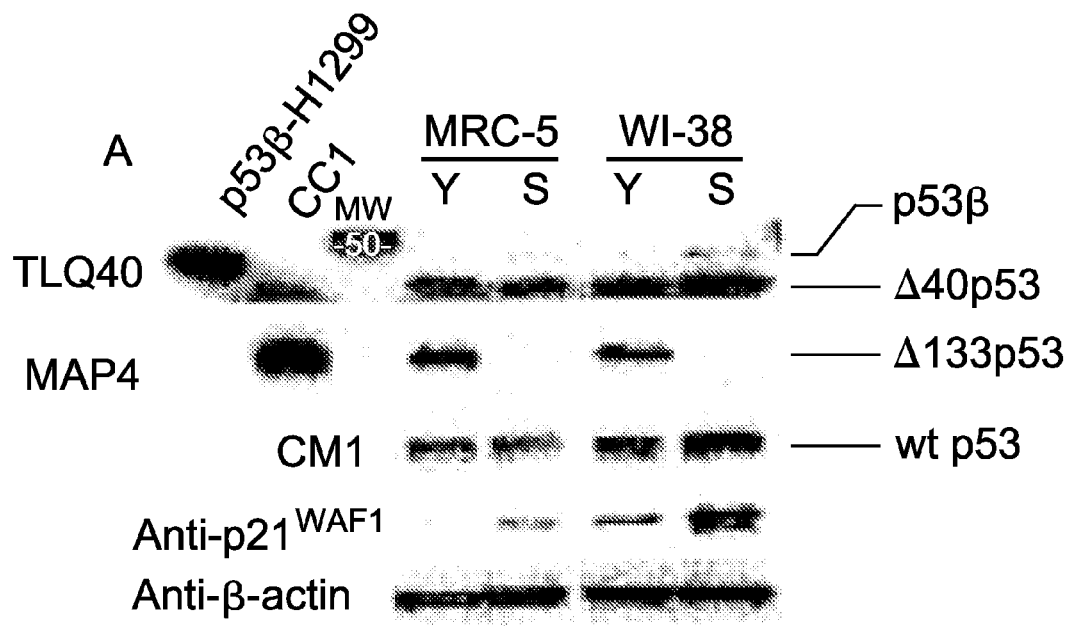
FIGS. 1. p53β and Δ133p53 are involved in cellular senescence and proliferation: (A) Induction of p53β and repression of Δ133p53 at replicative senescence. The immunoblot analyses were performed in early-passage (Y) and senescent (S) human fibroblast strains MRC-5 and WI-38. The examined passage numbers were 30 (Y) and 65 (S) for MRC-5; and 30 (Y) and 58 (S) for WI-38. TLQ40, an antibody detecting p53(3 isoforms; MAP4, an antibody detecting Δ133p53; CM1, an antibody detecting wt p53. Δ40p53β (Ghosh, A. et al., *Mol. Cell. Biol.* 24:7987 (2004)) was a predominant form detected by TLQ40 and was constitutively expressed in both early-passage and senescent cells. p21$^{WAF1}$ expression was also examined. β-actin was a loading control. H1299 cells overexpressing p53β and CC1 cells (Horikawa, I. et al., *Hum. Mol. Genet.* 4:313 (1995)) were used as the positive controls for p53β and Δ133p53, respectively. (B) miR-34a expression during replicative senescence. The same set of MRC-5 and WI-38 fibroblasts as used in (A) were examined for miR-34a expression by real-time qRT-PCR. The data were normalized with control RNU66 expression and shown as the relative values. Three independent experiments were carried out and the reproducible results were obtained. (C) Retroviral overexpression of p53β and Δ133p53 in human fibroblasts. The retroviral vectors driving wt p53, FLAG-tagged p53β and FLAG-tagged Δ133p53 were transduced to human fibroblasts at early passage (at passage number 30 for both strains) and the immunoblot analyses of the overexpressed p53 isoforms, MDM2 and p21$^{WAF1}$ were performed. Protein samples were prepared from the cells at 8 days after retroviral transduction. The anti FLAG antibody detected FLAG-tagged p53β and FLAG-tagged Δ133p53, and the DO-12 antibody detected all the three p53 isoforms. β-actin was a loading control. (D) Effects of p53β and Δ133p53 on cell proliferation. The cells were plated at 8 days after retroviral transduction and the cell numbers were counted daily. Vector (open squares), wt p53 (open diamonds), FLAG-p53β (closed circles), and FLAG-Δ133p53 (closed triangles). The data (mean±standard error) were from three independent experiments. (E) Senescence-associated β-galactosidase (SA-β-gal) assay. The cells were examined at 8 days after retroviral transduction. The data (mean±standard error) were from three independent experiments.
Figure 1:
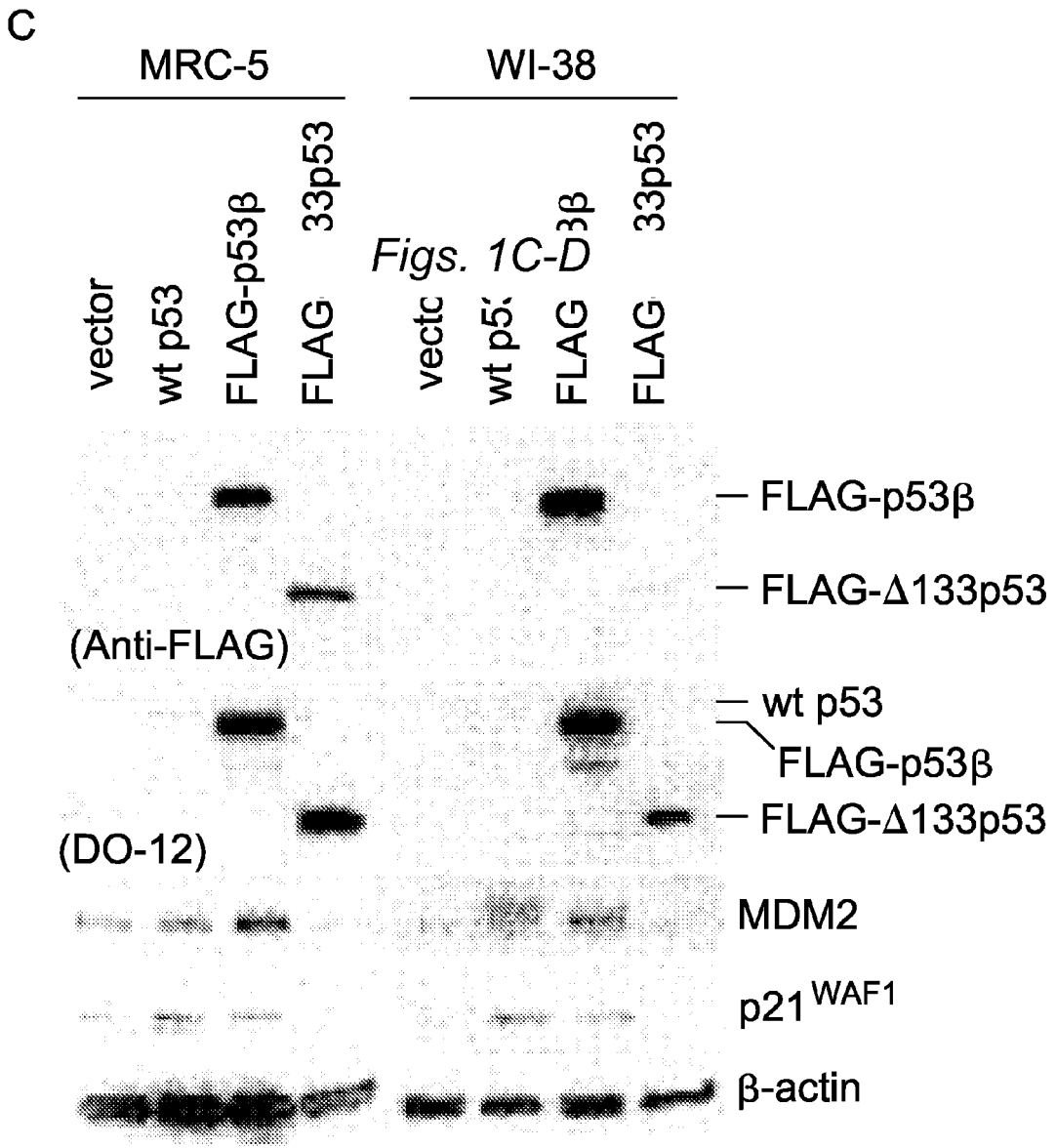

The finite division potential of normal human cells leads to cellular senescence, which functions as a barrier to human cell transformation and carcinogenesis (Collado, M., et al., *Cell* 130:223 (2007)). The induction and prevention of cellular senescence in human cells involve the regulation of the specific chromosome end structure, telomeres (Verdun, R. E. et al., *Nature* 447:924 (2007)). The tumor suppressor protein p53 plays a central role in sensing and signaling a variety of intrinsic stresses (e.g., telomere dysfunction) and environmental cues that induce cellular senescence (Collado, M., et al., *Cell* 130:223 (2007); Herbig, U. et al., *Mol. Cell.* 14:501 (2004)). p53 and Arf can also cooperate to have anti-oxidative and anti-aging activities (Matheu, A. et al., *Nature* 448:375 (2007)). Many of the mutant p53 proteins observed in human cancers inhibit the tumor suppressive functions of full-length, wild-type p53 (wt p53) in a dominant-negative manner (Rozan, L. M. et al., *Cell Death Differ.* 14:3 (2007)). It is suggested that some p53 mutants also gain a tumor-promoting function independent of the inhibition of wt p53 (Rozan, L. M. et al., *Cell Death Differ.* 14:3 (2007); Kastan, M. B. et al., *Nat. Cell Biol.* 9:489 (2007)). The human p53 gene encodes, in addition to wt p53, several N-terminally, internally and C-terminally truncated isoforms due to alternative promoter usage and RNA splicing (Chan, W. M. et al., *Cancer Res.* 67:1959 (2007), Bourdon, J. C. et al., *Genes Dev.* 19:2122 (2005)). A plausible hypothesis is that these p53 isoforms cooperate or compete with wt p53 to modulate the p53's multiple functions. To test this hypothesis, we examine here the roles of two major isoforms, p53β (lacking the C-terminal oligomerization domain due to an alternative splicing) and Δ133p53 (transcribed from the alternative promoter in intron 4 and lacking the N-terminal transactivation and proline-rich domains) (Bourdon, J. C. et al., *Genes Dev.* 19:2122 (2005)), in the regulation of cellular senescence and their functional interplay with wt p53. Our data provide novel insights into the p53 regulation of cellular replicative lifespan.

II. p53 Proteins p53 is a protein of apparent molecular 53 kDa on SDS PAGE that functions as a transcription factor that, among other functions, regulates the cell cycle and functions as a tumor suppressor. p53 has been described as "the guardian of the genome", referring to its role in providing stability by preventing genome mutation. Among p53's anti-cancer activities include: activation of DNA repair proteins when DNA has sustained damage; cell cycle arrest at the G1/S regulation point when a cell has sustained DNA damage, thus allowing DNA repair proteins time to fix the damage before allowing continuation of the cell cycle; and the initiation of apoptosis or the programmed cell death, if the DNA damage proves to be irreparable.

Accordingly, p53 can induce growth arrest, apoptosis, and cell senescence. In normal cells, p53 is generally held in an inactive form, bound to the protein MDM2 (HDM2 in humans), which prevents p53 activity and promotes p53 degradation by acting as a ubiquitin ligase. Active p53 is induced in response to various cancer-causing agents such as UV radiation, oncogenes, and some DNA-damaging drugs. DNA damage is sensed by 'checkpoints' in a cell's cycle, and causes proteins such as ATM, CHK1 and CHK2 to phosphorylate p53 at sites that are close to or within the MDM2-binding region and p300-binding region of the protein. Oncogenes also stimulate p53 activation, mediated by the protein p14ARF. Some oncogenes can also stimulate the transcription of proteins which bind to MDM2 and inhibit its activity. Once activated, p53 activates expression of several genes including one encoding for p21, a cell cycle inhibitor. p21 binds to G1-S-phase and S-phase cyclin CDK complexes inhibiting their activity. See, e.g., Mills, *Genes & Development*, 19: 2091-2099 (2005) for a review.

Other isoforms or variants of p53 have been identified (see Bourdon, *Brit. J. Cancer*, 97: 277-282 (2007)). For example, two isoforms of p53, p63 and p73, which are encoded by distinct genes, have been identified (Kaghad et al., *Cell* 90: 809-819 (1997); and Yang et al. *Mol. Cell.* (1998)). Human p53 isoforms may also arise due to alternative promoter usage and alternative splicing. Alternative promoter usage, for example, can give rise to the expression of an N-terminally truncated p53 protein initiated at codon 133 (Δ133p53). Adding to the complexity of p53 isoforms is the alternative splicing of intron 9 of the p53 gene to provide the isoforms p53β and p53γ. Combined with alternative promoter usage, this gives rise to the p53 isoforms: p53, p53β, p53γ, Δ133p53, Δ133p53β, and Δ133p53γ. The use of an alternative promoter in intron 2 gives rise to the additional isoforms, Δ40p53, Δ40p53β, and Δ40p53γ. While the presence of these multiple p53 isoforms has been established, the biological function of these isoforms remains obscure. The present invention is based in part on an elucidation of the role for two of these isoforms, Δ133p53 and p53β, in the opposing functions of cell senescence and cell proliferation.

III. Definitions

The term "p53" refers generally to a protein of apparent molecular weight of 55 kDa on SDS PAGE that functions as a tumor suppressor as described herein. The protein and nucleic sequences of the p53 protein from a variety of organisms from humans to *Drosophila* are known and are available in public databases, such as in accession numbers, NM_000546, NP_000537, NM_011640, and NP_035770, for the human and mouse sequences.

The term "Δ133p53" refers generally to the isoform of p53 which arises from initiation of transcription of the p53 gene from codon 133, which results in an N-terminally truncated p53 protein. This isoform comprises the following p53 protein domains: the majority of the DNA binding domain, the NLS, and the C-terminal sequence DQTSFQKENC (SEQ ID NO:12) (see Bourdon, Brit. J. Cancer, 97: 277-282 (2007)).

The term "p53β" refers generally to the isoform of p53 wiich arises from alternative splicing of intron 9 to provide a p53 isoform comprising the following p53 protein domains: TAD1, TAD2, prD, the DNA binding domain, the NLS, and the C-terminal sequence DQTSFQKENC (SEQ ID NO:12) (see Bourdon, Brit. J. Cancer, 97: 277-282 (2007)).

The term "cell senescence" refers generally to the phenomenon where normal diploid differentiated cells lose the ability to divide after undergoing a finite number of cell divisions characteristic of a particular type of cell.

The term "replicative lifespan" refers generally to the finite number of cell divisions undergone by a particular cell type before undergoing cell senescence and losing the ability to further divide.

The term "extending replicative lifespan" refers generally to the continuation of cell division in a normal diploid cell beyond the finite number of cell divisions at which cell senescence would occur.

The term "siRNA" refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 nucleotides in length, e.g., 20, 21, 22, 23, 24, 25, 26, 27, 28, 29, or 30 nucleotides in length.

The term "shRNA" refers generally to an siRNA that is introduced into a cell as part of a larger DNA construct. Typically, such constructs allow stable expression of the siRNA in cells after introduction, e.g., by integration of the construct into the host genome.

An "antisense" oligonucleotide or polynucleotide is a nucleotide sequence that is substantially complementary to a target polynucleotide or a portion thereof and has the ability to specifically hybridize to the target polynucleotide.

Ribozymes are enzymatic RNA molecules capable of catalyzing specific cleavage of RNA. The composition of ribozyme molecules preferably includes one or more sequences complementary to a target mRNA, and the well known catalytic sequence responsible for mRNA cleavage or a functionally equivalent sequence (see, e.g., U.S. Pat. No. 5,093,246, which is incorporated herein by reference in its entirety). Ribozyme molecules designed to catalytically cleave target mRNA transcripts can also be used to prevent translation of subject target mRNAs.

The term "promoting" as used, for example in the context of "promoting senescence," refers generally to conditions or agents which increase, induce, open, activate, facilitate, enhance activation, sensitize, agonize, or up regulate cell senescence.

The phrase "functional effects" in the context of assays for testing compounds that modulate a protein of the invention includes the determination of a parameter that is indirectly or directly under the influence of a protein of the invention, e.g., a chemical or phenotypic effect such as altered transcriptional activity of p53 isoforms and the downstream effects of such proteins on cellular metabolism and proliferation or growth. A functional effect therefore includes transcriptional activation or repression, the ability of cells to proliferate or undergo apoptosis, whether and at what point cells undergo senescence, among others. "Functional effects" include in vitro, in vivo, and ex vivo activities.

By "determining the functional effect" is meant assaying for a compound that increases or decreases a parameter that is indirectly or directly under the influence of a p53 isoform of the invention, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape), chromatographic; or solubility properties for the protein; ligand binding assays, e.g., binding to antibodies; measuring inducible markers or transcriptional activation of the marker; measuring changes in enzymatic activity; the ability to increase or decrease cellular proliferation, senescence, apoptosis, cell cycle arrest, measuring changes in cell surface markers. The functional effects can be evaluated by many means known to those skilled in the art, e.g., microscopy for quantitative or qualitative measures of alterations in morphological features, measurement of changes in RNA or protein levels for other genes expressed in a cell, measurement of RNA stability, identification of downstream or reporter gene expression (CAT, luciferase, GFP and the like), e.g., via chemiluminescence, fluorescence, colorimetric reactions, antibody binding, inducible markers, etc.

"Inhibitors," "activators," and "modulators" of the proteins of the invention are used to refer to activating, inhibitory, or modulating molecules identified using in vitro and in vivo assays of p53 isoforms. Inhibitors are compounds that, e.g., bind to, partially or totally block activity, decrease, prevent, delay activation, inactivate, desensitize, or down regulate the activity or expression of p53 isoforms. "Activators" are compounds that increase, open, activate, facilitate, enhance activation, sensitize, agonize, or up regulate activity of p53 isoforms, e.g., agonists Inhibitors, activators, or modulators also include genetically modified versions of p53 isoforms, e.g., versions with altered activity, as well as naturally occurring and synthetic ligands, antagonists, agonists, antibodies, peptides, cyclic peptides, nucleic acids, antisense molecules, ribozymes, RNAi molecules, small organic molecules and the like. Such assays for inhibitors and activators include, e.g., expressing p53 isoforms in vitro, in cells, or cell extracts, applying putative modulator compounds, and then determining the functional effects on activity, as described above.

Samples or assays comprising p53 isoforms that are treated with a potential activator, inhibitor, or modulator are compared to control samples without the inhibitor, activator, or modulator to examine the extent of inhibition. Control samples (untreated with inhibitors) are assigned a relative protein activity value of 100% Inhibition of p53 isoforms is achieved when the activity value relative to the control is about 80%, preferably 50%, more preferably 25-0%. Activation of p53 isoforms is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, peptide, circular peptide, lipid, fatty acid, siRNA, polynucleotide, oligonucleotide, etc., to be tested for the capacity to directly or indirectly modulate p53 isoforms. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

IV. Nucleic Acids and Proteins of the Invention

A. General Recombinant DNA Methods

This invention relies on routine techniques in the field of recombinant genetics. Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et. al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

B. Methods for Isolating Nucleotide Sequences Encoding Δ133p53 or p53β

In general, the nucleic acid sequences encoding Δ133p53 or p53β and related nucleic acid sequence homologues can be cloned from cDNA libraries or isolated using amplification techniques with oligonucleotide primers. Nucleic acids encoding Δ133p53 or p53β can also be isolated from expression libraries using antibodies as probes.

Advantageously, the cloning of Δ133p53 or p53β or other p53 isoforms can employ the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of Δ133p53 or p53β directly from mRNA, from cDNA, from genomic libraries or cDNA libraries. Degenerate oligonucleotides can be designed to amplify Δ133p53 or p53β homologues for other species using known sequences. Restriction endonuclease sites can be incorporated into the primers. Genes amplified by the PCR reaction can be purified from agarose gels and cloned into an appropriate vector.

The nucleic acids encoding Δ133p53 or p53β or other p53 isoforms are typically cloned into intermediate vectors before transformation into prokaryotic or eukaryotic cells for replication and/or expression. These intermediate vectors are typically prokaryote vectors, e.g., plasmids, or shuttle vectors. The isolated nucleic acids encoding Δ133p53 or p53β or other p53 isoforms comprise nucleic acid sequences these proteins and subsequences, interspecies homologues, alleles and polymorphic variants thereof.

C. Expression of Δ133p53 or p53β in Prokaryotes and Eukaryotes

To obtain high level expression of a cloned gene, such as those cDNAs encoding Δ133p53 or p53β, one typically subclones Δ133p53 or p53β nucleic acids into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing Δ133p53 or p53β proteins are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of Δ133p53 or p53β encoding nucleic acid in host cells. A typical expression cassette thus contains a promoter operably linked to the nucleic acid sequence encoding Δ133p53 or p53β proteins and signals required for efficient polyadenylation of the transcript, ribosome binding sites, and translation termination. Additional elements of the construct may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

Many conventional vectors for transport of genetic information into a cell may be used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation and detection, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Standard transfection methods may be used to introduce the nucleic acid constructs of the invention into bacterial, mammalian, yeast or insect cell lines. Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983). These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra).

An advantageous expression system involves the use of retroviral expression vectors to express the constructs of the invention. After the cloning of a suitable nucleic acid encoding Δ133p53 or p53β or an inhibitory nucleic acid into an appropriate retroviral vector, the nucleic acid constructs are transfected into an appropriate retroviral packaging cell such as PE 501, BOSC, ψCRE, GP+E-86, PA317, ψCRIP, GP+envAm12, and Phoenix, among others, depending on the cell type to be ultimately infected with the resulting retrovirus (see, e.g., *Recombinant Gene Expression Protocols in Methods* in *Molecular Biol.*, vol. 62, ed. R. Tuan, Humana Press (1997)).

V. Inhibition of p53 Isoforms Using Nucleic Acids

Inhibitory nucleic acids to Δ133p53 or p53β, such as siRNA, shRNA, ribozymes, or antisense molecules, can be synthesized and introduced into cells using methods known in the art. Molecules can be synthesized chemically or enzymatically in vitro (Micura, *Agnes Chem. Int. Ed. Emgl.* 41: 2265-9 (2002); Paddison et al., *Proc. Natl. Acad. Sci. USA*, 99: 1443-8 2002) or endogenously expressed inside the cells in the form of shRNAs (Yu et al., *Proc. Natl. Acad. Sci. USA*, 99: 6047-52 (2002); McManus et al., *RNA* 8, 842-50 (2002)). Plasmid-based expression systems using RNA polymerase III U6 or H1, or RNA polymerase II U1, small nuclear RNA promoters, have been used for endogenous expression of shRNAs (Brummelkamp et al., *Science*, 296: 550-3 (2002); Sui et al., *Proc. Natl. Acad. Sci. USA*, 99: 5515-20 (2002); Novarino et al., *J. Neurosci.*, 24: 5322-30 (2004)). Synthetic siRNAs can be delivered by electroporation or by using lipophilic agents (McManus et al., *RNA* 8, 842-50 (2002); Kishida et al., *J. Gene Med.*, 6: 105-10 (2004)). Alternatively, plasmid systems can be used to stably express small hairpin RNAs for the suppression of target genes (Dykxhoorn et al., *Nat. Rev. Mol. Biol.*, 4: 457-67 (2003)). Various viral delivery systems have been developed to deliver shRNA-expressing cassettes into cells that are difficult to transfect (Brummelkamp et al., *Cancer Cell*, 2: 243-7 (2002); Rubinson et al., *Nat. Genet.*, 33: 401-6 2003). Furthermore, siRNAs can also be delivered into live animals. (Hasuwa et al., *FEBS Lett.*, 532, 227-30 (2002); Carmell et al., *Nat. Struct. Biol.*, 10: 91-2 (2003); Kobayashi et al., *J. Pharmacol. Exp. Ther.*, 308: 688-93 (2004)).

Methods for the design of siRNA or shRNA target sequences have been described in the art. Among the factors to be considered include: siRNA target sequences should be specific to the gene of interest and have ~20-50% GC content (Henshel et al., *Nucl. Acids Res.*, 32: 113-20 (2004); G/C at the 5' end of the sense strand; A/U at the 5' end of the antisense strand; at least 5 A/U residues in the first 7 bases of the 5' terminal of the antisense strand; and no runs of more than 9 G/C residues (Ui-Tei et al., *Nucl. Acids Res.*, 3: 936-48 (2004)). Additionally, primer design rules specific to the RNA polymerase will apply. For example, for RNA polymerase III, the polymerase that transcribes from the U6 promoter, the preferred target sequence is 5'-GN18-3'. Runs of 4 or more Ts (or As on the other strand) will serve as terminator sequences for RNA polymerase III and should be avoided. In addition, regions with a run of any single base should be avoided (Czauderna et al., *Nucl. Acids Res.*, 31: 2705-16 (2003)). It has also been generally recommended that the mRNA target site be at least 50-200 bases downstream of the start codon (Sui et al., *Proc. Natl. Acad. Sci. USA*, 99: 5515-20 (2002); Elbashir et al., *Methods*, 26: 199-213 (2002); Duxbury and Whang, *J. Surg. Res.*, 117: 339-44 (2004) to avoid regions in which regulatory proteins might bind. Additionally, a number of computer programs are available to aid in the design of suitable siRNA and shRNAs for use in the practice of this invention.

Ribozymes that cleave mRNA at site-specific recognition sequences can be used to destroy target mRNAs, particularly through the use of hammerhead ribozymes. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art.

Gene targeting ribozymes necessarily contain a hybridizing region complementary to two regions, each of at least 5 and preferably each 6, 7, 8, 9, 10, 11, 12, 13, 14, 15, 16, 17, 18, 19 or 20 contiguous nucleotides in length of a target mRNA. In addition, ribozymes possess highly specific endoribonuclease activity, which autocatalytically cleaves the target sense mRNA.

With regard to antisense, siRNA or ribozyme oligonucleotides, phosphorothioate oligonucleotides can be used. Modifications of the phosphodiester linkage as well as of the heterocycle or the sugar may provide an increase in efficiency. Phosphorothioate is used to modify the phosphodiester linkage. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo.

Inhibitory oligonucleotides can be delivered to a cell by direct transfection or transfection and expression via an expression vector. Appropriate expression vectors include mammalian expression vectors and viral vectors, into which has been cloned an inhibitory oligonucleotide with the appropriate regulatory sequences including a promoter to result in expression of the antisense RNA in a host cell. Suitable promoters can be constitutive or development-specific promoters. Transfection delivery can be achieved by liposomal transfection reagents, known in the art (e.g., Xtreme transfection reagent, Roche, Alameda, Calif.; Lipofectamine formulations, Invitrogen, Carlsbad, Calif.). Delivery mediated by cationic liposomes, by retroviral vectors and direct delivery are efficient. Another possible delivery mode is targeting using antibody to cell surface markers for the target cells.

For transfection, a composition comprising one or more nucleic acid molecules (within or without vectors) can comprise a delivery vehicle, including liposomes, for administration to a subject, carriers and diluents and their salts, and/or can be present in pharmaceutically acceptable formulations. Methods for the delivery of nucleic acid molecules are described, for example, in Gilmore, et al., *Curr Drug Delivery* (2006) 3:147-5 and Patil, et al., *AAPS Journal* (2005) 7:E61-E77, each of which are incorporated herein by reference. Delivery of siRNA molecules is also described in several U.S. Patent Publications, including for example, 2006/0019912; 2006/0014289; 2005/0239687; 2005/0222064; and 2004/0204377, the disclosures of each of which are hereby incorporated herein by reference. Nucleic acid molecules can be administered to cells by a variety of methods known to those of skill in the art, including, but not restricted to, encapsulation in liposomes, by iontophoresis, by electroporation, or by incorporation into other vehicles, including biodegradable polymers, hydrogels, cyclodextrins (see, for example Gonzalez et al., 1999, *Bioconjugate Chem.*, 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and US Patent Application Publication No. 2002/130430), biodegradable nanocapsules, and bioadhesive microspheres, or by proteinaceous vectors (O'Hare and Normand, International PCT Publication No. WO 00/53722). In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

Examples of liposomal transfection reagents of use with this invention include, for example: CellFectin, 1:1.5 (M/M) liposome formulation of the cationic lipid N,NI,NII,NIII-tetramethyl-N,NI,NII,NIII-tetrapalmit-y-spermine and dioleoyl phosphatidylethanolamine (DOPE) (GIBCO BRL); Cytofectin GSV, 2:1 (M/M) liposome formulation of a cationic lipid and DOPE (Glen Research); DOTAP (N-[1-(2,3-dioleoyloxy)-N,N,N-tri-methyl-ammoniummethylsulfate) (Boehringer Manheim); Lipofectamine, 3:1 (M/M) liposome formulation of the polycationic lipid DOSPA and the neutral lipid DOPE (GIBCO BRL); and (5) siPORT (Ambion); HiPerfect (Qiagen); X-treme GENE (Roche); RNAicarrier (Epoch Biolabs) and TransPass (New England Biolabs).

In some embodiments, antisense, siRNA, or ribozyme sequences are delivered into the cell via a mammalian expression vector. For example, mammalian expression vectors suitable for siRNA expression are commercially available, for example, from Ambion (e.g., pSilencer vectors), Austin, Tex.; Promega (e.g., GeneClip, siSTRIKE, SiLentGene), Madison, Wis.; Invitrogen, Carlsbad, Calif.; InvivoGen, San Diego, Calif.; and Imgenex, San Diego, Calif. Typically, expression vectors for transcribing siRNA molecules will have a U6 promoter.

In some embodiments, antisense, siRNA, or ribozyme sequences are delivered into cells via a viral expression vector. Viral vectors suitable for delivering such molecules to cells include adenoviral vectors, adeno-associated vectors, and retroviral vectors (including lentiviral vectors). For example, viral vectors developed for delivering and expressing siRNA oligonucleotides are commercially available from, for example, GeneDetect, Bradenton, Fla.; Ambion, Austin, Tex.; Invitrogen, Carlsbad, Calif.; Open BioSystems, Huntsville, Ala.; and Imgenex, San Diego, Calif.

VI. Assays of Cell Senescence, Cell Proliferation, and Apoptosis

Any of a number of known methods for the determination and measurement of cell senescence, cell proliferation, and apoptosis may be used in the practice of this invention. Direct measurements of cell proliferation include direct counting of cells using, e.g., a hematocytometer, measurement of the incorporation of labeled DNA precursors such as $^3$H-thymidine and BrdU, or through the measurement of cell markers that are expressed in proliferating cells, such PCNA, or by measurement of a marker for cellular metabolism such as MTT (see, e.g., Hughes, D., Cell proliferation and apoptosis, Taylor & Francis Ltd, UK (2003). Other methods such as soft agar growth or colony formation in suspension, contact inhibition and density limitation of growth, or growth factor or serum dependence of growth, among others, may be used to assess cell growth, especially of cancer cells as compared to normal cells (see, e.g., Freshney, *Culture of Animal Cells a Manual of Basic Technique*, 3rd ed., Wiley-Liss, New York (1994)).

A number of markers for cell senescence may be used to monitor this process in the practice of this invention. The most common of these markers is senescence-associated-β-galactoside (Dimri, G. P. et al., *Proc. Natl. Acad. Sci. USA* 92:9363 (1995)), although others such, as the direct measurement of telomere length by in situ hybridization, and age-dependent cellular accumulation of lipofucin in cells (Coates, *J. Pathol.*, 196: 371-3 (2002)), are also known.

Typical assays used to detect and measure apoptosis include microscopic examination of cellular morphology, TUNEL assays for DNA fragmentation, caspase activity assays, annexin-V externalization assays, and DNA laddering assays, among others (see, e.g., Hughes, D., *Cell proliferation and apoptosis*, Taylor & Francis Ltd, UK (2003)).

VII. Methods to Identify Modulators

A variety of methods may be used to identify compounds that modulate p53 isoforms. Typically, an assay that provides a readily measured parameter is adapted to be performed in the wells of multi-well plates in order to facilitate the screening of members of a library of test compounds as described herein. Thus, in one embodiment, an appropriate number of cells or other suitable preparation can be plated into the cells of a multi-well plate, and the effect of a test compound on a p53 isoform can be determined.

The compounds to be tested can be any small chemical compound, or a macromolecule, such as a protein, sugar, nucleic acid or lipid. Typically, test compounds will be small chemical molecules and peptides. Essentially any chemical compound can be used as a test compound in this aspect of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods are used which involve providing a combinatorial chemical or peptide library containing a large number of potential therapeutic compounds. Such "combinatorial chemical libraries" or "ligand libraries" are then screened in one or more assays, as described herein, to identify those library members (particular chemical species or subclasses) that display a desired characteristic activity. In this instance, such compounds are screened for their ability to reduce or increase the function or expression of the p53 isoforms of the invention.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries are well known to those of skill in the art. Such combinatorial chemical libraries include, but are not limited to, peptide libraries (see, e.g., U.S. Pat. No. 5,010,175, Furka, *Int. J. Pept. Prot. Res.*, 37:487-493 (1991) and Houghton et al., *Nature*, 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *PNAS USA*, 90:6909-6913 (1993)), vinylogous polypeptides (Hagihara et al., *J. Amer. Chem. Soc.*, 114:6568 (1992)), nonpeptidal peptidomimetics with glucose scaffolding (Hirschmann et al., *J. Amer. Chem. Soc.*, 114:9217-9218 (1992)), analogous organic syntheses of small compound libraries (Chen et al., *J. Amer. Chem. Soc.*, 116:2661 (1994)), oligocarbamates (Cho et al., *Science*, 261:1303 (1993)), and/or peptidyl phosphonates (Campbell et al., *J. Org. Chem.*, 59:658 (1994)), nucleic acid libraries (see Ausubel, Berger and Sambrook, all supra), peptide nucleic acid libraries (see, e.g., U.S. Pat. No. 5,539, 083), antibody libraries (see, e.g., Vaughn et al., *Nature Biotechnology*, 14(3):309-314 (1996) and PCT/US96/10287), carbohydrate libraries (see, e.g., Liang et al., *Science*, 274: 1520-1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100- about 1500 different compounds. It is possible to assay many plates per day; assay screens for up to about 6,000, 20,000, 50,000, or 100,000 or more different compounds is possible using the integrated systems of the invention.

EXAMPLES

The following examples are offered to illustrate, but not to limit the claimed invention.

Example 1

Methods and Materials

Cells

CC1, a human choriocarcinoma cell line expressing Δ133p53 due to the genomic rearrangement deleting the exons 2, 3 and 4 (Horikawa, I. et al., *Hacm. Mol. Genet.* 4:313 (1995)), was a gift from Dr. Mitsuo Oshimura (Tottori University, Japan). Fibroblasts from Li-Fraumeni syndrome patients (MDAH041, MDAH087 and MDAH172) (Bischoff, F. Z. et al., *Cancer Res.* 50:7979 (1990)) were kindly provided by Dr. Michael Tainsky (Case Western Reserve University, Cleveland, Ohio). Normal human fibroblast strains (MRC-5 and WI-38), H1299 and 293T were obtained from American Type Culture Collection (Manassas, Va.). hTERT/NHF, an hTERT (human telomerase reverse transcriptase)-immortalized human fibroblast cell line, was previously described (Sengupta, S. et al., *EMBO J.* 22:1210 (2003)).

Plasmid Constructs

To generate the retroviral expression vectors of human p53 isoforms, full-length p53, FLAG-tagged p53β and FLAG-tagged Δ133p53 were PCR-amplified using pSVrp53, pSVp53β and pSVDNp53 (Bourdon, J. C. et al., *Genes Dev.* 19:2122 (2005)), respectively, as the templates, and then inserted into Not I and Eco RI sites of pQCXIN vector (BD Biosciences). A retroviral shRNA construct for p53 knockdown, targeting nucleotide positions 1026 to 1044 in NM_000546 (Brummelkamp, T. R. et al., *Science* 296:550 (2002)), was derived from pSUPERretro vector carrying a ptuomycin-resistant gene (Oligoengine, Seattle, Wash.). To generate a retroviral vector driving the dominant-negative mutant of Siah-1A (FLAG-Siah1-ΔRING), the human Siah-1A cDNA fragment (nucleotide positions 325 to 966 in NM_003031.3) was PCR-amplified using a 5' primer with FLAG tag sequence and cloned into pBABE-puro. The resulting construct drives an N-terminally deleted Siah-1A protein (residues 70 to 282) missing the RING finger domain (Hu, G. et al., *Mol. Cell. Biol.* 19:724 (1999)). For a retroviral vector driving FLAG-tagged Siah1-Δ6 (a stable form of Siah-1A, consisting of residues 6 to 282) (Tanikawa, J. et al., *J. Biol. Chem.* 279:55393 (2004)), the human Siah-1A cDNA fragment (nucleotide positions 133 to 966 in NM_003031.3) was amplified and processed in the same way. These constructs were verified by DNA sequencing. The retroviral construct pLPC-Myc-TRF2 was a gift from Dr. Titia de Lange (Rockefeller University, NY).

Retroviral Vector Production and Transduction

The retroviral constructs were transfected into Phoenix packaging cells (Orbigen, Inc.) using Lipofectamin 2000 (Invitrogen). Vector supernatants were collected 48 h after transfection and used to infect cells in the presence of 8 μg/ml polybrene (Sigma-Aldrich). Two days after infection, the infected cells were selected with 600 μg/ml of G418 (Sigma-Aldrich), 2 μg/ml of puromycin (Sigma-Aldrich) or 1 mg/ml of zeocin (Invitrogen).

siRNA and Antisense Oligonucleotides

A stealth siRNA duplex oligoribonucleotide targeting Δ133p53 mRNA (Δ133si-1, 5'-UGU UCA CUU GUG CCC UGA CUU UCA A-3', SEQ ID NO:1), its scrambled control, and a standard siRNA duplex oligoribonucleotide targeting Δ133p53 mRNA (Δ133si-2, 5'-CUU GUG CCC UGA CUU UCA A[dT][dT]-3', SEQ ID NO:2) were synthesized at Invitrogen. The following antisense 2'-O-methyl oligonucleotides were purchased from Integrated DNA Technologies (Coralville, Iowa): 5'-AAC AAC CAG CUA AGA CAC UGC CA-3' (SEQ ID NO:3) for inhibiting miR-34a; and 5'-AAG GCA AGC UGA CCC UGA AGU-3' (SEQ ID NO:4) as a control, which is complementary to the enhanced green fluorescence protein (EGFP). These siRNA and antisense oligonucleotides were transfected at the final concentration of 12 nM and 40 nM, respectively, into MRC-5 and WI-38 fibroblasts by using the Lipofectamine RNAiMAX transfection reagent (Invitrogen) according to the supplier's protocol.

Cell Proliferation Assay, Senescence-Associated-Galactosidase (SA-β-gal) Staining, Examination of Cellular Replicative Lifespan, and Bromo-Deoxyuridine (BrdU) Incorporation Assay For cell proliferation assay, 2.4×10$^5$ cells per well were plated into 12-well plates. These cells were collected and counted daily for a week using a hematocytometer. The experiments were performed at least twice and data at each time point were in triplicate. For examining cellular replicative lifespan, the number of cells was counted at each passage, and the number of population doublings (PDL) achieved between passages was determined by log$_2$ (number of cells obtained/number of cells inoculated) (Michishita, E. et al., *Mol. Biol. Cell* 16:4623 (2005); Pereira-Smith, O. M. et al., *Somatic Cell Genet.* 7:411 (1981)). SA-β-gal staining was performed as previously described (Dimri, G. P. et al., *Proc. Natl. Acad. Sci. USA* 92:9363 (1995)). For BrdU incorporation assay, cells were incubated with 10 μM of BrdU for 24 h. The incorporated BrdU was detected using an anti-BrdU monoclonal antibody (Amersham Biosciences) and observed with a fluorescent microscope. The nuclei were counterstained with 4',6-diamidino-2-phenylindole (DAPI).

Immunoblot Analysis and Immunoprecipitation

Cells were lysed in RIPA buffer [10 mM Tris-HCl, pH 7.5, 150 mM NaCl, 0.1% SDS, 0.1% sodium deoxycholate, 1 mM EDTA, 1% NP-40, complete protease inhibitors (Roche), phosphatase inhibitor cocktail 1 and 2 (Sigma)]. Lysates were separated by SDS-PAGE and transferred to nitrocellulose membranes (BIO-RAD). Immunoblot analysis was accomplished according to standard procedures using ECL detection (Amersham Bioscience) or SuperSignal West Dura Extended Duration system (PIERCE).

A polyclonal antibody specifically recognizing Δ133p53 (MAP4) was raised at Moravian Biotechnology (Brno, Czech Republic) in rabbits injected with a mixture of peptides MFC-QLAKTC (SEQ ID NO:13) and FCQLAKTCP (SEQ ID NO:14), which were synthesized as Multiple Antigenic Peptide by G. Bloomberg (University of Bristol, Bristol, UK). The other primary antibodies used were: TLQ40 (Bourdon, J. C. et al., *Genes Dev.* 19:2122 (2005; Murray-Zmijewski, F. et al., *Cell Death Differ.* 13:962 (2006)) for p53β; CM1 (Bourdon, J. C. et al., *Genes Dev.* 19:2122 (2005); Murray-Zmijewski, F. et al., *Cell Death Differ.* 13:962 (2006)), DO-12 (Chemicon) and DO-1 (Santa Cruz) for p53; H-164 (Santa Cruz) for p21$^{WAF1}$; SMP14 (Santa Cruz) for MDM2; 4A794 (Upstate) for TRF2; M2 monoclonal antibody (Sigma) for FLAG tag; AC-15 (Sigma) for β-actin; anti-Myc tag antibody (Invitrogen); anti-ubiquitin ligase Siah-1A (Aviva Systems Biology); and anti-β-catenin mouse monoclonal antibody (BD Biosciences). Horseradish peroxidase-conjugated goat anti-mouse or anti-rabbit antibodies (Santa Cruz) were used as secondary antibodies.

Real-Time qRT-PCR for Quantification of microRNA (miRNA) Expression

RNA samples were prepared by using Trizol (Invitrogen). Reverse transcriptase reactions were performed using TagMan miRNA reverse transcription kit (Applied Biosystems, cat. no. 4366596) and a miR-34a-specific primer. The TagMan miRNA assay kit for miR-34a (Applied Biosystems, cat. no. 4373278) was used according to the supplier's protocol. Real-time PCR reactions were performed in triplicate. RNU66 (Applied Biosystems, cat. no. 4373382) was used as a control for quantification. Based on Ct (cycle threshold) values from miR-34a and RNU66 detections, normalized miR-34a expression was calculated by using the ΔΔCt method according to the supplier's protocol (protocol no. 4310255B and User Bulletin no. 4303859B at http://www.appliedbiosystems.com/index.cfm).

Measurement of Telomeric 3' Overhang and Telomere Length

Genomic DNA samples were digested with Hinf I and electrophoresed through 0.7% agarose gel. After drying at 25° C. for 30 min in a Bio-Rad model 583 gel dryer, the gel was hybridized with $^{32}$P-labeled [CCCTAA]$_4$ (SEQ ID NO:5) oligonucleotide as previously described (Miura, N. et al., *Cancer Genet. Cytogenet.* 93:56 (1997)), followed by washing and signal detection using the Typhoon 8600 system (Molecular Dynamics, Sunnyvale, Calif.). The amounts of telomeric 3' overhangs, normalized with loaded DNA amounts detected with ethidium bromide (EtBr) staining of the gel, were quantitated by using the ImageQuant version 5.2 software (Molecular Dynamics). After alkali denaturation (0.5M NaOH/1.5M NaCl) and neutralization (2.5M NaCl/0.5M Tris-HCl, pH 7.5) of the dried gel, the same procedures were repeated to examine telomere length, which was indicated as a peak TRF (terminal restriction fragment) length.

Example 2

Expression of p53β and Δ133p53 and p53 Target Genes

Figure 5:
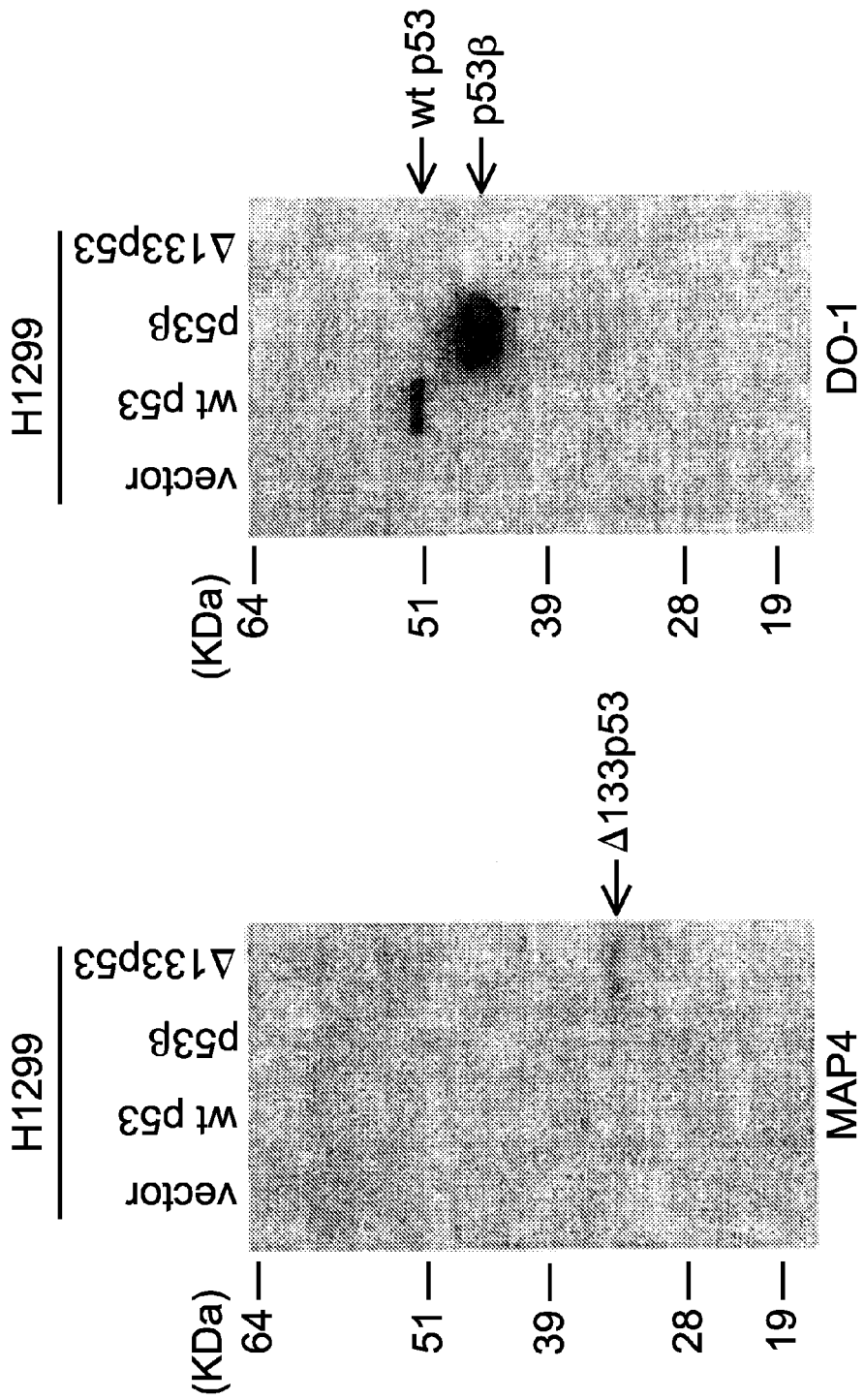
FIG. 5. MAP4 specifically recognizes Δ133p53. H1299 cells (p53-null) transfected with the expression vector for wild-type (wt) p53, p53β or Δ133p53 were analyzed in Western blot using MAP4 (left) and DO-1 (right) antibodies. MAP4 detects Δ133p53, but not wt p53 or p53β.
Figure 6:
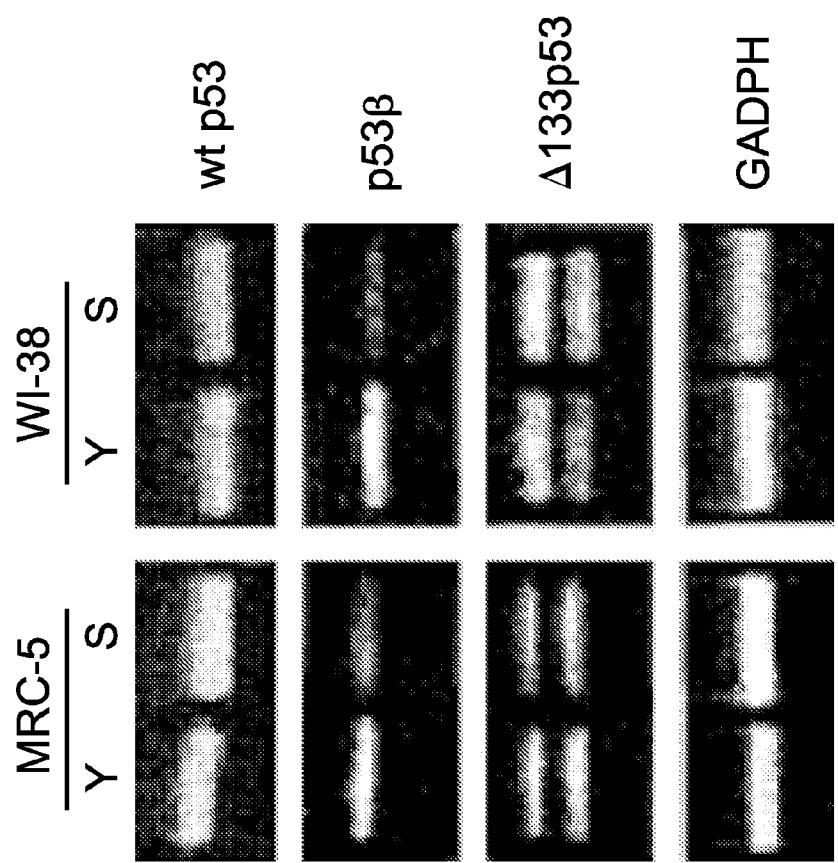
FIG. 6. mRNA expression analysis of p53 isoforms in human fibroblasts. The same sets of cells as in FIG. 1A were analyzed by RT-PCR. In contrast to protein levels, mRNA of p53β was decreased in senescent cells and Δ133p53 was primarily unchanged. The primers to amplify wt p53 were: 5'-CTC ACC ATC ATC ACA CTG GAA-3' (SEQ ID NO:6) and 5'-TCA TTC AGC TCT CGG AAC ATC-3' (SEQ ID NO:7). The primers specifically detecting the alternative splicing for p53β were: 5'-CTT TGA GGT GCG TGT TTG TGC-3' (SEQ ID NO:8) and 5'-TTG AAA GCT GGT CTG GTC CTG A-3'(SEQ ID NO:9). The primers specifically amplifying Δ133p53 mRNA transcribed from the promoter in intron 4 were: 5'-TGG GTT GCA GGA GGT GCT TAC-3' (SEQ ID NO:10)and 5'-CCA CTC GGA TAA GAT GCT GAG G-3' (SEQ ID NO:11). The lower bands correspond to the reported Δ133p53 sequences (GenBank DQ186650). The upper bands are from mRNA with intron 5 unspliced. GAPDH was amplified as a control as previously described (Horikawa, I. et al., *Mol. Carcinog.* 22:65 (1998)).

The antibodies specific to p53β (TLQ40) (Bourdon, J. C. et al., *Genes Dev.* 19:2122 (2005); Murray-Zmijewski, F. et al.,

*Cell Death Differ.* 13:962 (2006)) and Δ133p53 (MAP4; see Materials and Methods and FIG. 5) were raised and used to examine the endogenous expression of p53β and Δ133p53 in normal human fibroblast strains (MRC-5 and WI-38) at early passage and at replicative senescence (Y and S, respectively, in FIG. 1A). While the expression of wt p53 (detected by CM1) showed no changes during replicative senescence in these fibroblasts, p53β was specifically detected when the cells became senescent. In remarkable contrast, the expression of Δ133p53 was diminished in the senescent cells. The RT-PCR analyses showed neither an increase in the alternative RNA splicing producing p53β nor a decrease in the usage of the intron 4 promoter driving Δ133p53 in senescent fibroblasts (FIG. 6), suggesting that the induction of p53β and the repression of Δ133p53 occur at the posttranscriptional levels during replicative senescence. The senescence-associated changes in p53β and Δ133p53 coincided with the upregulation of p21$^{WAF1}$ (FIG. 1A), an effector of p53-mediated cellular senescence (Herbig, U. et al., *Mol. Cell.* 14:501 (2004); Brown, J. P. et al., *Science* 277:831 (1997)). An increased expression of miR-34a, a microRNA (miRNA) that is transcriptionally activated by wt p53 and has an ability to induce cellular senescence when overexpressed (Chang, T. C. et al., *Mol. Cell.* 26:745 (2007); He, L. et al., *Nature* 447:1130 (2007); Raver-Shapira, N. et al., *Mol. Cell.* 26:731 (2007)), was observed in MRC-5 and WI-38 when they entered into senescence (FIG. 1B), suggesting that the endogenous expression of miR-34a is involved in the p53-mediated regulation of replicative senescence.

Example 3

Figure 8:
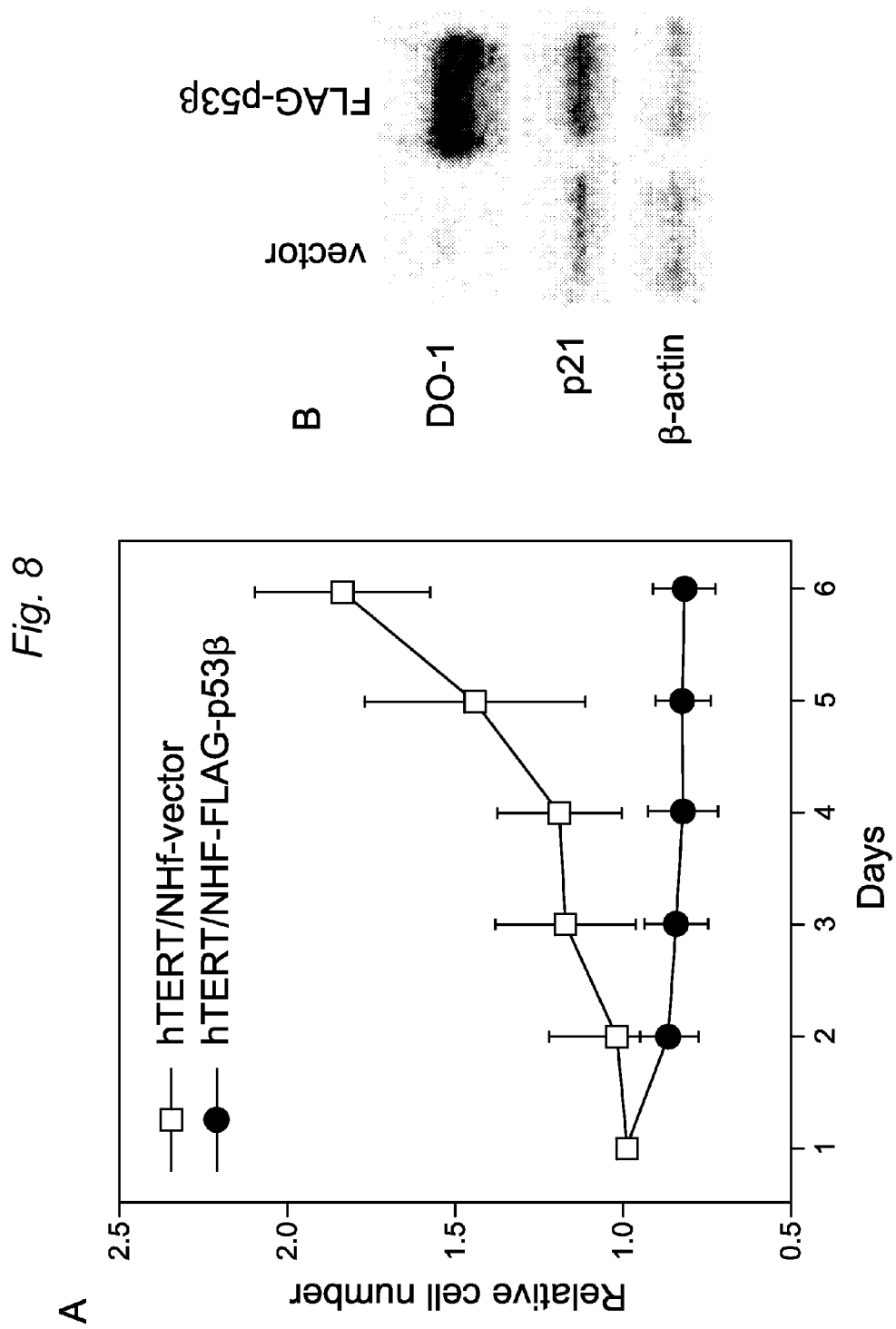
FIG. 8. p53β overexpression induces cellular senescence in human fibroblasts with ectopically expressed telomerase. (A) Effects of p53β on cell proliferation. hTERT (human telomerase reverse transcriptase)-immortalized human fibroblasts (hTERT/NHF) were transduced with the retroviral vector driving FLAG-tagged p53β or control vector (a zeocin-resistant version). Cell proliferation assay was carried out as in FIG. 2B. (B) Upregulation of p21$^{WAF1}$ by p53β overexpression in hTERT/NHF cells. (C) Representative pictures of SA-β-gal staining. (D) Summary of SA-β-gal staining. The data were mean±standard error from three independent experiments.
Figure 8:
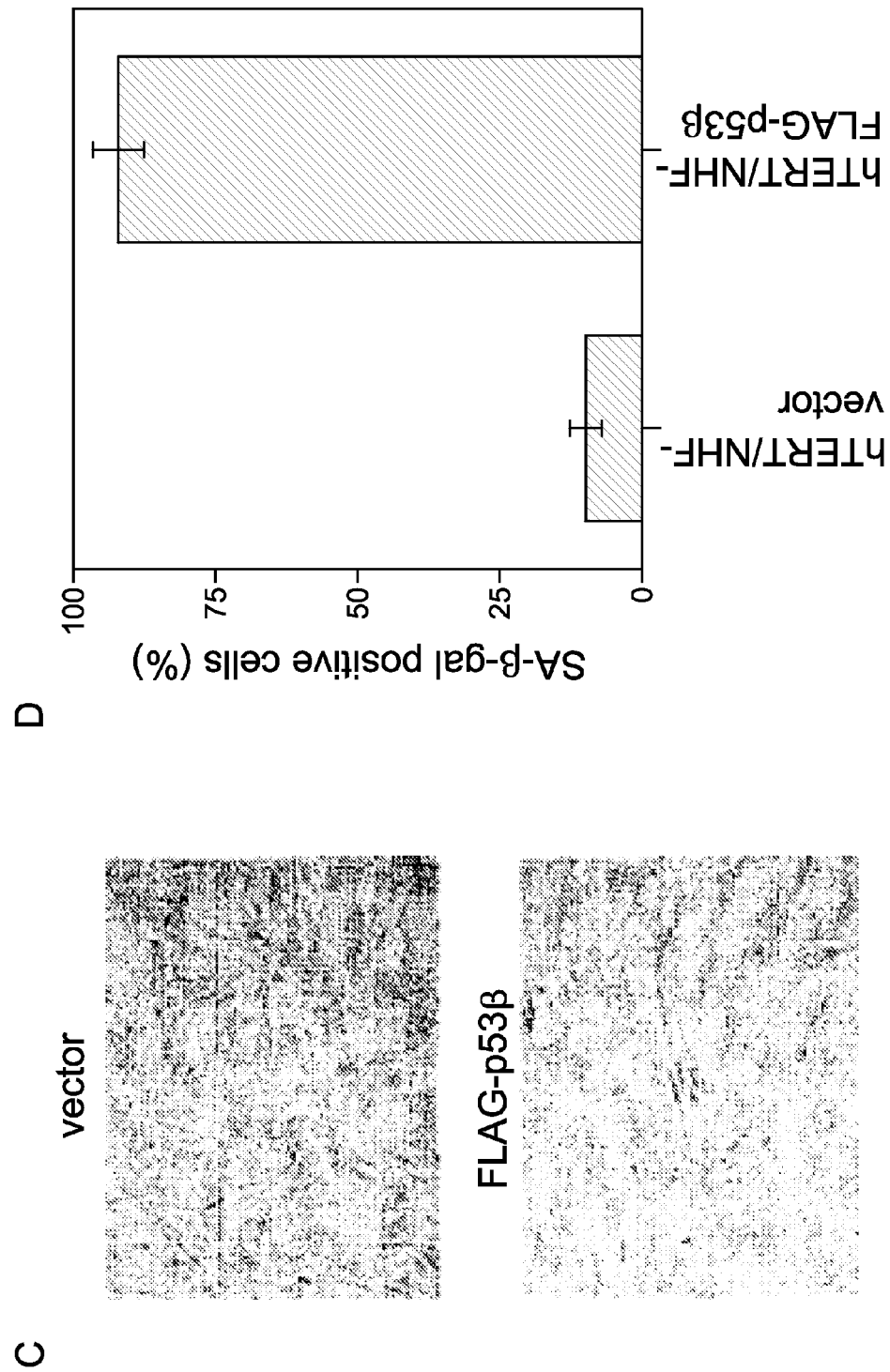

Effect of Overexpression of p53β and Δ133p53 on Cell Proliferation and Senescence The senescence-specific changes in the endogenous p53β and Δ133p53 expression prompted us to examine the effects of overexpression of these p53 isoforms on cell proliferation and senescence. The FLAG-tagged p53β and Δ133p53, as well as wt p53, were retrovirally expressed in the early-passage human fibroblast strains (FIG. 1C). Similar to wt p53, p53β inhibited cell proliferation (FIG. 1D) and induced cellular senescence, characterized by the senescence-associated β-galactosidase (SA-β-Gal) activity (FIG. 1E and FIG. 7). The senescence induction by p53β overexpression was associated with the upregulation of the wt p53 transcriptional targets, p21$^{WAF1}$ and MDM2 (Rozan, L. M. et al., *Cell Death Differ.* 14:3 (2007)) (FIG. 1C), confirming that p53β enhances the intrinsic transcriptional activity of p53 as previously described (Bourdon, J. C. et al., *Genes Dev.* 19:2122 (2005)). p53β also inhibited cell proliferation and induced cellular senescence in a telomerase-immortalized fibroblast cell line (FIG. 8). However, p53β had no effects on cell proliferation, cellular senescence or the expression of p21$^{WAF1}$ and MDM2 in p53-null MDAH041 fibroblasts (Yin, Y. et al., *Cell* 70:937 (1992)) (data not shown; also see FIG. 13A below), indicating that p53β co-operates with wt p53 to enhance its senescence-inducing activity. In marked contrast to wt p53 and p53β, the overexpression of Δ133p53 accelerated cell proliferation of the normal human fibroblasts (FIG. 1D) without inducing cellular senescence (FIG. 1E and FIG. 7), and repressed the expression of p21$^{WAF1}$ and MDM2 (FIG. 1C).

Figure 2:
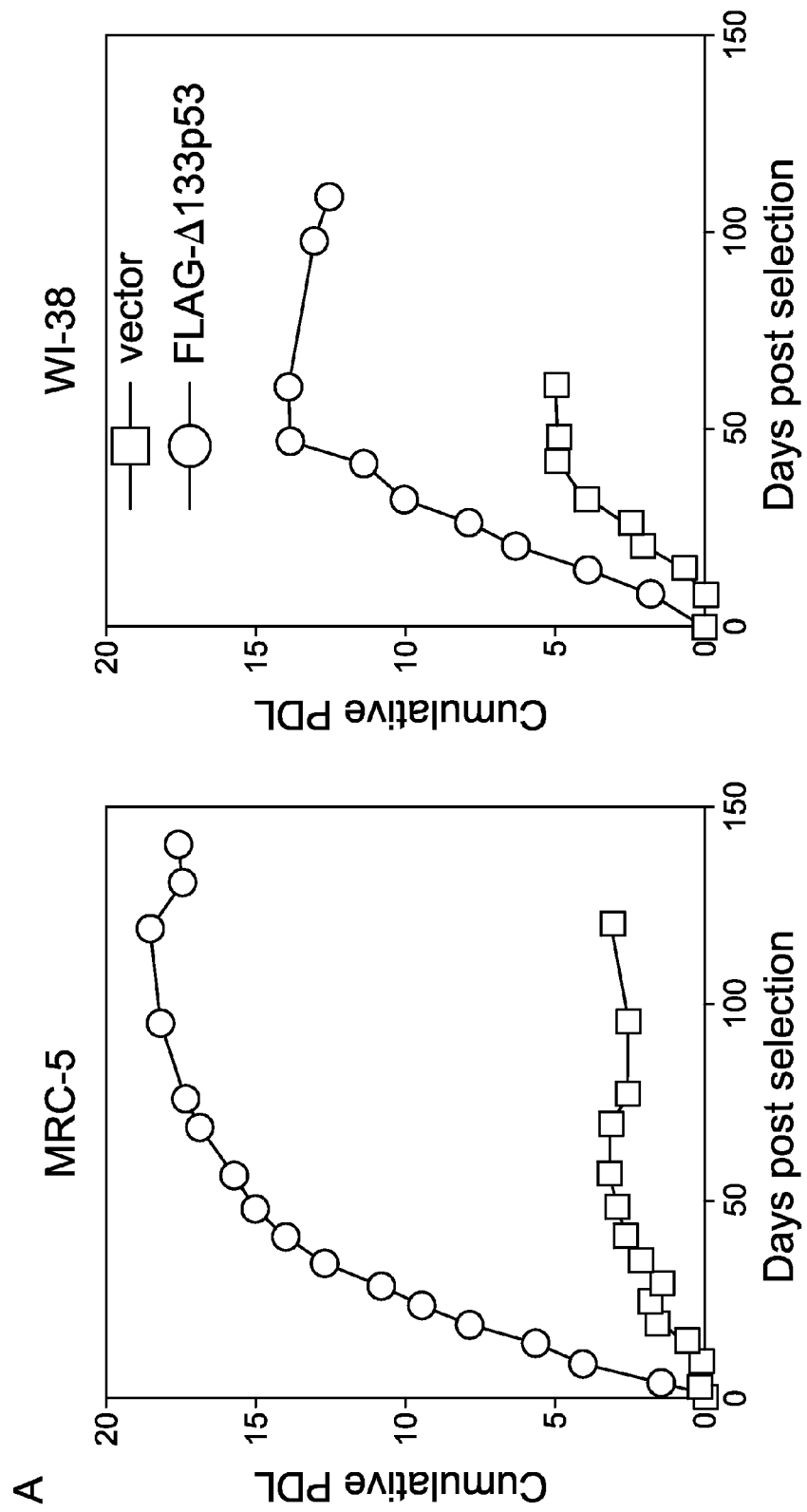
FIG. 2. Overexpression of Δ133p53 extends replicative lifespan. (A) Examination of cellular replicative lifespan. The FLAG-Δ133p53 retroviral vector (open circles) or the control vector (open squares) was transduced to human fibroblasts at late passage (MRC-5 at passage 53 and WI-38 at passage 51). The cumulative population doublings (PDL) were calculated and plotted to days after G418 selection. (B) Telomere length and telomeric 3' overhang in Δ133p53-overexpressing cells. Genomic DNA samples from MRC-5 with FLAG-Δ133p53 or control vector were used in the in-gel hybridization with $^{32}$P-[CCCTAA]$_4$ (SEQ ID NO:5) probe under denatured (for telomere length) and native (for telomeric 3' overhang) conditions. Lane 1, MRC-5 before transduction; lanes 2-3, vector control (days 4 and 35 post selection); lanes 4-6, FLAG-Δ133p53 (days 4, 35 and 96 post selection). The telomere lengths were measured as peak TRF (terminal restriction fragment) lengths. The amounts of telomeric 3' overhang were normalized with loaded DNA amounts (EtBr) and shown as percent signals to the cells before transduction. (C) Repression of miR-34a expression by Δ133p53. RNA samples from MRC-5 (at passage 53) before transduction (day 0), MRC-5 with control vector and MRC-5 overexpressing Δ133p53 (at days 20, 36 and 96 post selection) were analyzed as in FIG. 1B. The value before transduction was defined as 1.0 and the expression levels in the other samples were expressed as the relative values. (D) Extension of cellular replicative lifespan by inhibition of miR-34a expression. The late-passage MRC-5 fibroblasts were transfected with the antisense oligonucleotide against miR-34a and the control oligonucleotide (EGFP) every four days and the cumulative PDL were examined as in (A) (left panel). The downregulation of miR-34a expression was confirmed by the real-time qRT-PCR (right panel).
Figure 2:
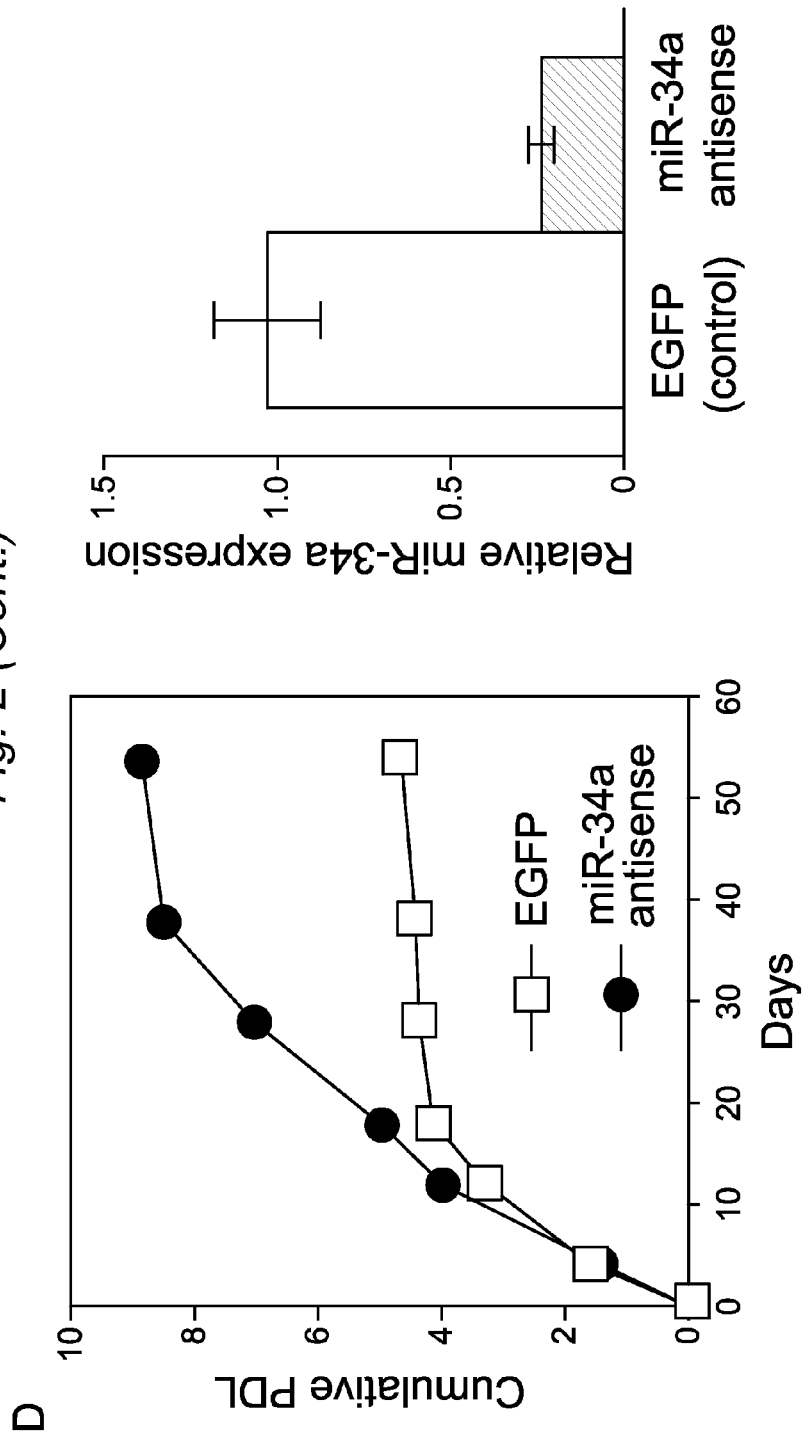
Figure 9:
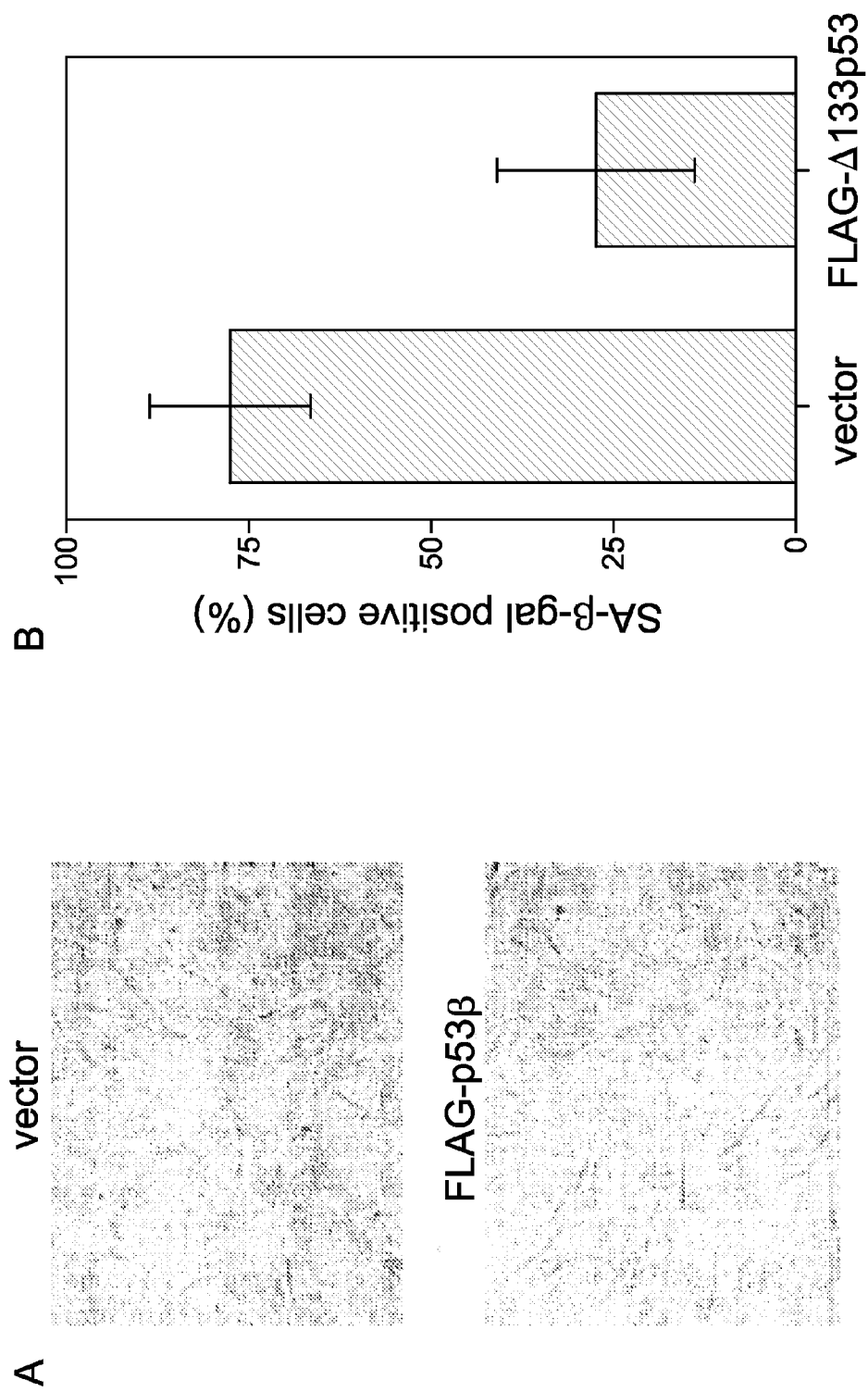
FIG. 9. Δ133p53 overexpression delays replicative senescence in late-passage human fibroblasts. MRC-5 fibroblasts with control vector or FLAG-tagged Δ133p53 (same cells as in FIG. 3A) were stained for SA-β-gal activity at 10 days post G418 selection. (A) Representative pictures. (B) Data summary.

The biological effects of Δ133p53 were more evident when it was overexpressed in the late-passage human fibroblasts, just before the senescent stage (FIG. 2). In the fibroblast strains MRC-5 and WI-38, whereas the vector control cells underwent senescent growth arrest at only three or five population doublings (PDLs) after retroviral transduction, the Δ133p53-overexpressing cells bypassed this normal senescence point and continued to proliferate for an additional 10 or 15 PDLs (FIG. 2A and FIG. 9). The analysis of telomeres revealed that the Δ133p53-induced extension of the replicative lifespan was not due to telomere stabilization: both the overall length of telomeres and the amount of telomeric 3' overhangs continued to be reduced in the Δ133p53-overexpressing cells (FIG. 2B). The peak length of telomere terminal restriction fragments (TRF) in the Δ133p53-overexpressing MRC-5 at the end of the replicative lifespan was reduced down to 4.3 Kbs, which was 1.8-Kb shorter than that in the senescent vector control cells. The relative amount of 3' overhangs at the end of the replicative lifespan was also less in the Δ133p53-overexpressing cells than in the vector control cells (37% in the former versus 71% in the latter). These data suggest that the Δ133p53 expression allowed normal human cells to continue proliferating beyond the checkpoint defined by a certain level of telomere length and 3' overhang amount, which would otherwise lead to cellular senescence (Stewart, S. A. et al., *Nat. Genet.* 33:492 (2003)). As shown in FIG. 2C, the expression of miR-34a in Δ133p53-overexpressing MRC-5 fibroblasts remained restricted to low levels throughout their replicative lifespan. The inhibition of miR-34a expression by an antisense oligonucleotide extended the replicative lifespan in MRC-5 fibroblasts (FIG. 2D). These results suggest that the impaired induction of this p53 target miRNA contributes to the extension of replicative lifespan by Δ133p53.

Example 4

Effect of Inhibition of Δ133p53 on Cell Senescence

Figure 3:
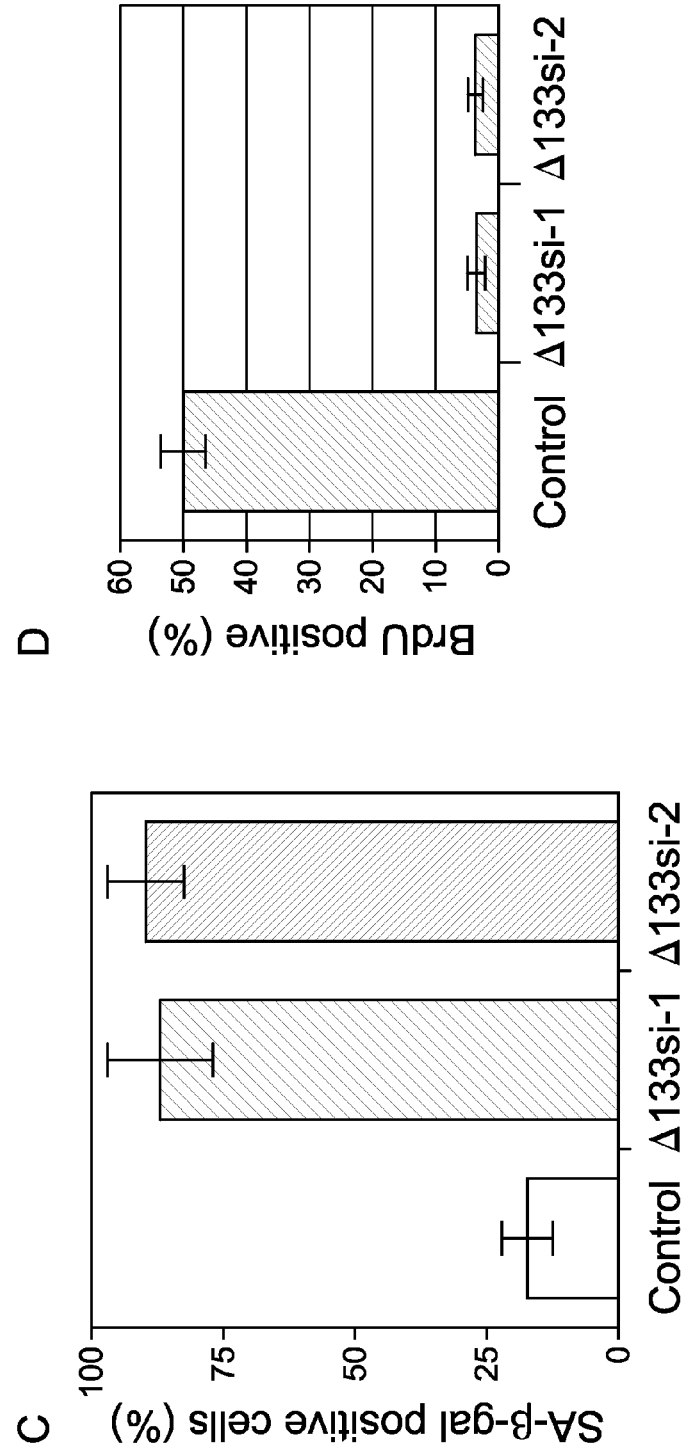
FIG. 3. Knockdown of endogenous Δ133p53 expression induces cellular senescence. Early-passage MRC-5 fibroblasts (at passage 32) were transfected with siRNAs targeting Δ133p53 (Δ133si-1 and Δ133si-2) and a control oligonucleotide twice (at day 1 and day 4), and at day 7 were used for immunoblot analyses (A) and examined for SA-β-Gal activity (B and C) and bromo-deoxyuridine (BrdU) incorporation (D). (A) siRNA-mediated repression of Δ133p53. Expressions of wt p53 (DO-1 antibody), Δ133p53 (MAP4 antibody) and p21$^{WAF1}$ were examined. β-actin was a loading control. (B) Representative pictures of SA-β-Gal staining. (C) Summary of SA-β-Gal assay. The data (mean±standard error) were from two independent experiments. (D) Summary of BrdU incorporation assay. The number of BrdU-positive cells/the total number of cells examined (at least 100 cells for each sample) was recorded.
Figure 10:
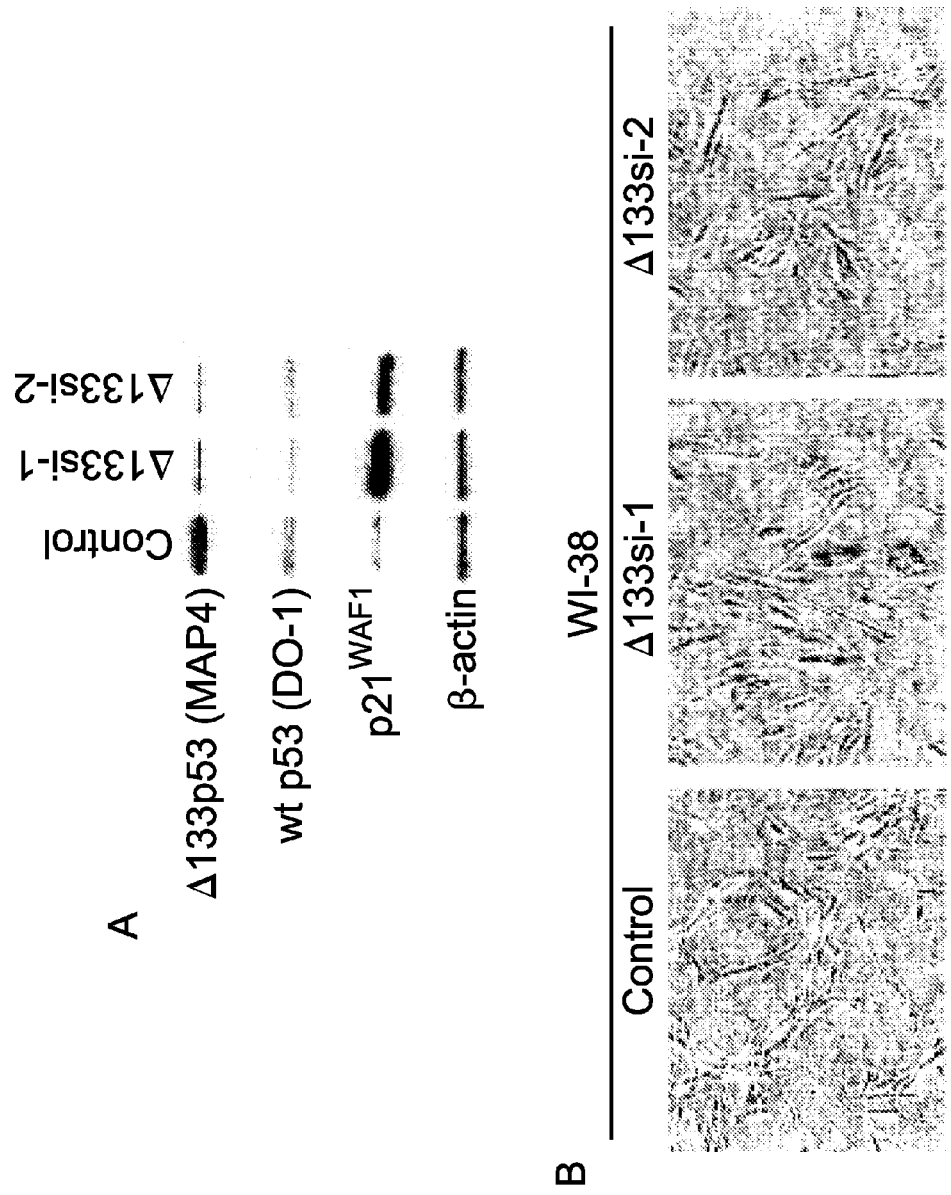
FIG. 10. Knockdown of endogenous Δ133p53 induces cellular senescence. Early-passage WI-38 fibroblasts (at passage 30) were transfected with siRNAs targeting Δ133p53 (Δ133si-1 and Δ133si-2) and a control oligonucleotide and examined in immunoblot analyses (A), SA-β-Gal assay (B) and BrdU incorporation assay (C), as performed in FIG. 3.
Figure 10:
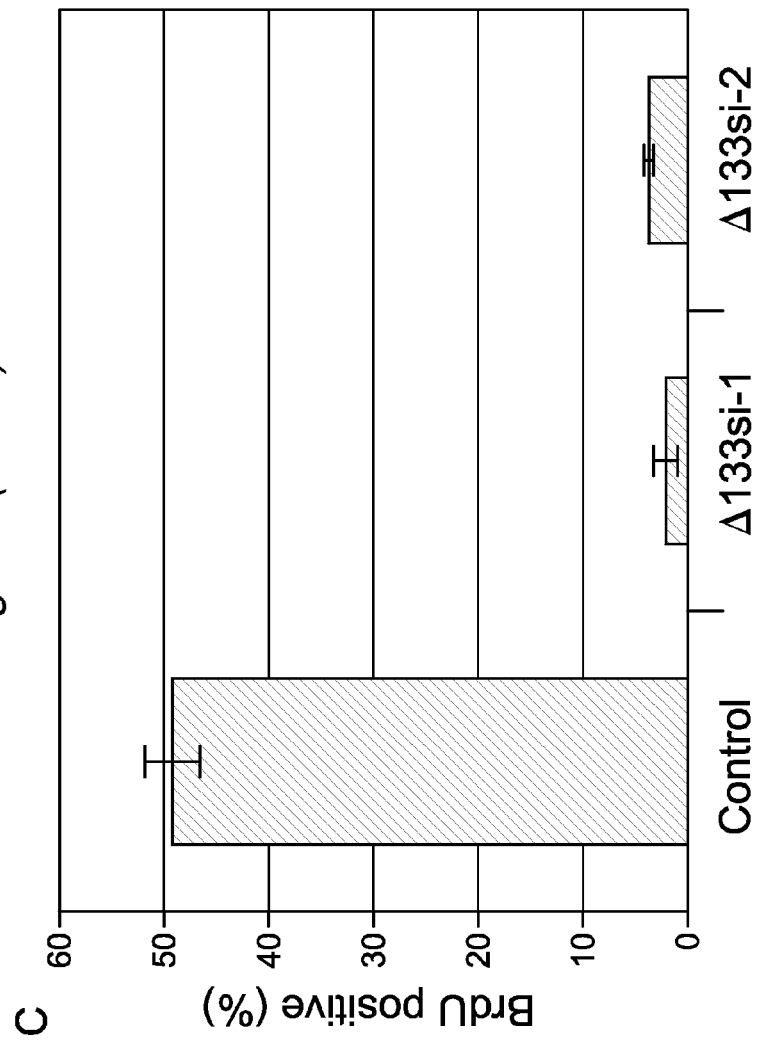

To examine the physiological role of Δ133p53 in the regulation of cellular senescence, the endogenous expression of Δ133p53 was knocked down by RNA interference in early-passage MRC-5 (FIG. 3) and WI-38 fibroblasts (FIG. 10). Two small interfering RNA (siRNA) oligonucleotides (Δ133si-1 and Δ133 si-2), which target the sequences that are present in Δ133p53 mRNA as 5' untranslated region but spliced out of wt p53 mRNA as intron 4, efficiently down-regulated the endogenous Δ133p53 without affecting wt p53 expression (FIG. 3A and FIG. 10A). The cells transfected with Δ133si-1 and Δ133si-2, but not those with a control scrambled oligonucleotide, underwent a senescent growth arrest uniformly and rapidly (within 7 days), showing the flattened cell morphology (FIG. 3B and FIG. 10B), the induction of SA-β-Gal activity (FIG. 3B, 3C and FIG. 10B), the attenuation of BrdU incorporation (FIG. 3D and FIG. 10C) and the upregulation of p21$^{WAF1}$ (FIG. 3A and FIG. 10A). These results indicate that the endogenous expression of Δ133p53 is critical to the replicative potential of normal human fibroblasts, and that the downregulation of Δ133p53 plays a causative role in a physiological induction of cellular senescence.

The continuous cell proliferation beyond the normal senescence checkpoint with a progressive erosion of telomeres was previously observed in various human cell culture systems, including SV40 large T- and HPV E6/E7-expressing fibroblasts (Harley, C. B. et al., *Gerontol.* 27:375 (1992)). Similar to these precedents, the lifespan extension by Δ133p53 was associated with the impaired expression of p21$^{WAF1}$ (FIG. 1C), a cyclin-dependent kinase inhibitor responsible for p53-mediated cellular senescence (Herbig, U. et al., *Mol. Cell.* 14:501 (2004); Brown, J. P. et al., Science 277:831 (1997)). The repression of miR-34a by Δ133p53 (FIG. 2C) may allow a group of genes for cell cycle progression to remain expressed (Chang, T. C. et al., *Mol. Cell.* 26:745 (2007)). It is thus likely that the dysregulated cell cycle progression, even in the presence of short telomeres, underlay the lifespan extension by Δ133p53. Our results indicate that Δ133p53 might also have an effect on telomeres.

Example 5

Effect of Inhibition of Δ133p53 on Proteins Involved in Telomere Length

Figure 4:
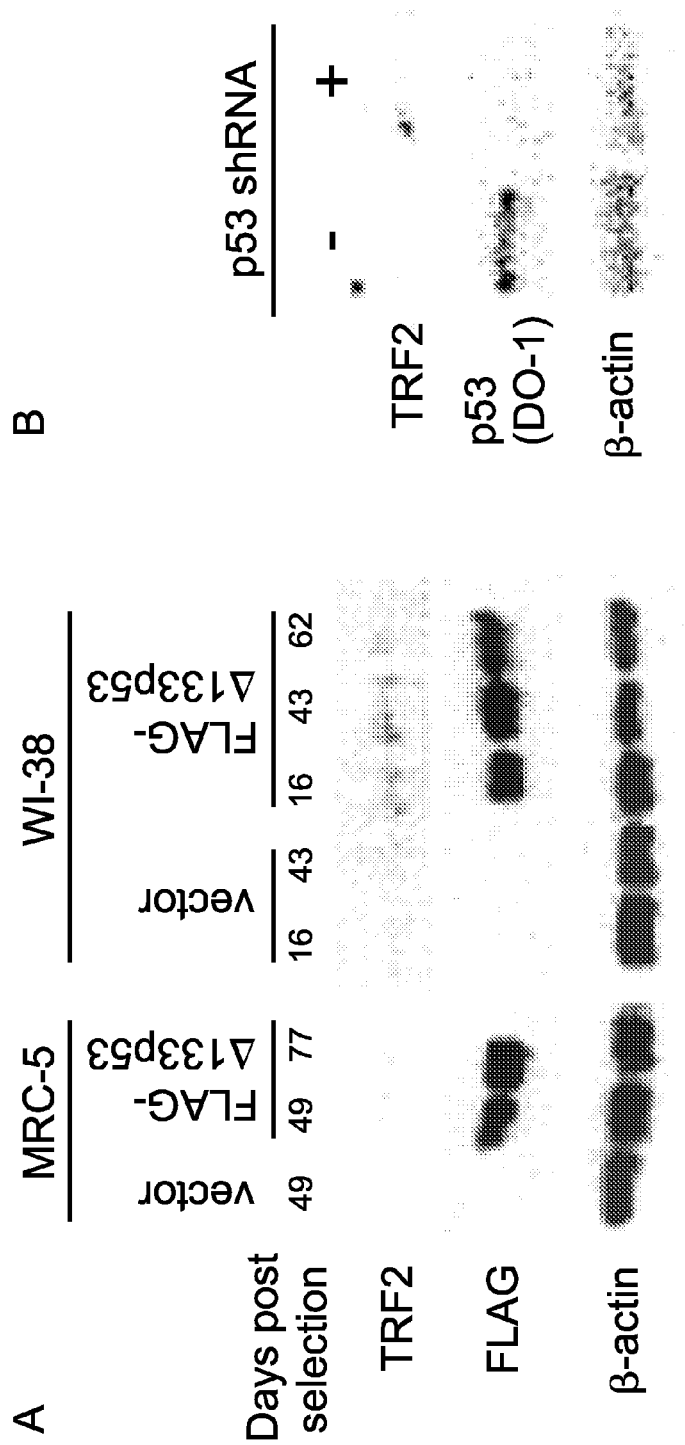
FIG. 4. Δ133p53 inhibits wt p53-mediated degradation of TRF2. (A) Immunoblot analysis of TRF2 expression in Δ133p53-overexpressing cells. MRC-5 and WI-38 fibroblasts with FLAG-Δ133p53 or control vector at indicated days after G418 selection (see FIG. 2A) were examined for TRF2 expression. The expression of Δ133p53 was confirmed by anti-FLAG antibody. (B) Immunoblot analysis of TRF2 in p53-knocked down cells. A telomerase-immortalized fibroblast cell line (hTERT/NHF) was transduced with the retroviral shRNA vector targeting p53. (C) p53 regulation of miR-34a expression. hTERT/NHF cells transduced with p53 shRNA (left) and treated with 10 μM of Nutlin-3a for 36 h (right) were examined for miR-34a expression, as in FIG. 1B. The data is shown as the relative expression level to control cells (−). (D) TRF2 expression in fibroblasts from Li-Fraumeni syndrome patients. MDAH041 has a p53 frame-shift mutation (−), and MDAH087 and MDAH172 have p53 missense mutations (mt) (Yin, Y. et al., *Cell* 70:937 (1992)). p53-heterozygous (wt/− and wt/mt) and homozygous (−/− and mt/mt) fibroblasts were examined in parallel. (E) Δ133p53 abrogates wt p53-mediated downregulation of TRF2. Cells (293T) were retrovirally transduced with Myc-tagged TRF2, wt p53 and FLAG-tagged Δ133p53 as indicated. Anti-Myc, anti-FLAG and DO-1 antibodies were used in immunoblot analyses. (F) Effects of a proteasome inhibitor (MG-132) on TRF2 expression. Control hTERT/NHF, Δ133p53-overexpressing hTERT/NHF and p53-knocked down hTERT/NHF were cultured in the presence (+) or absence (−) of 10 μM of MG-132 (Sigma-Aldrich) for 5 hrs and examined for TRF2 expression. (G) TRF2 accumulation by the inhibition of Siah-1A activity. The FLAG-tagged, dominant-negative mutant of Siah-1A (FLAG-Siah1-ΔRING) was expressed in MDAH041 fibroblasts (arrow). β-catenin, known to be degraded by Siah-1A (Matsuzawa, S. I. et al., *Mol. Cell.* 7:915 (2001)), was examined to confirm the activity of FLAG-Siah1-ΔRING. β-actin was a loading control in (A), (B), (D), (E), (F) and (G). (H) Overexpression of TRF2 extends replicative lifespan. MRC-5 fibroblasts at passage 39 were transduced with the retroviral vector driving Δ133p53 or control vector (G418 resistant) and selected with G418 for 7 days. These cells were then transduced with the retroviral vector driving TRF2 or control vector (puromycin resistant), selected with puromycin, and examined for cellular replicative lifespan as in FIG. 2A. For each combination of retroviral transductions, the cumulative PDL at days post puromycin selection were recorded.
Figure 4:
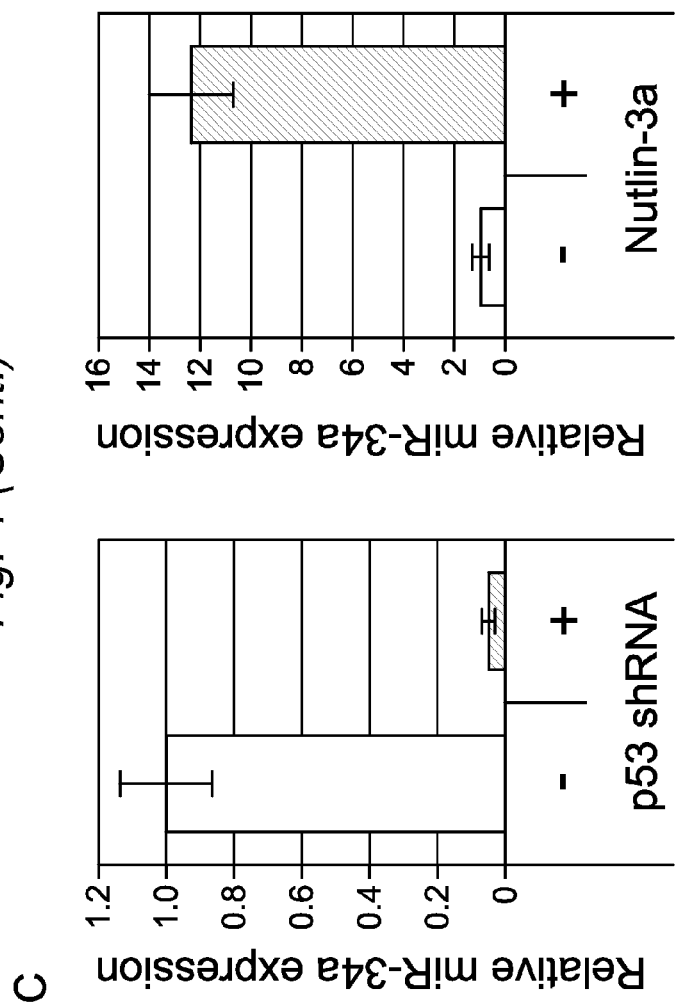
Figure 4:
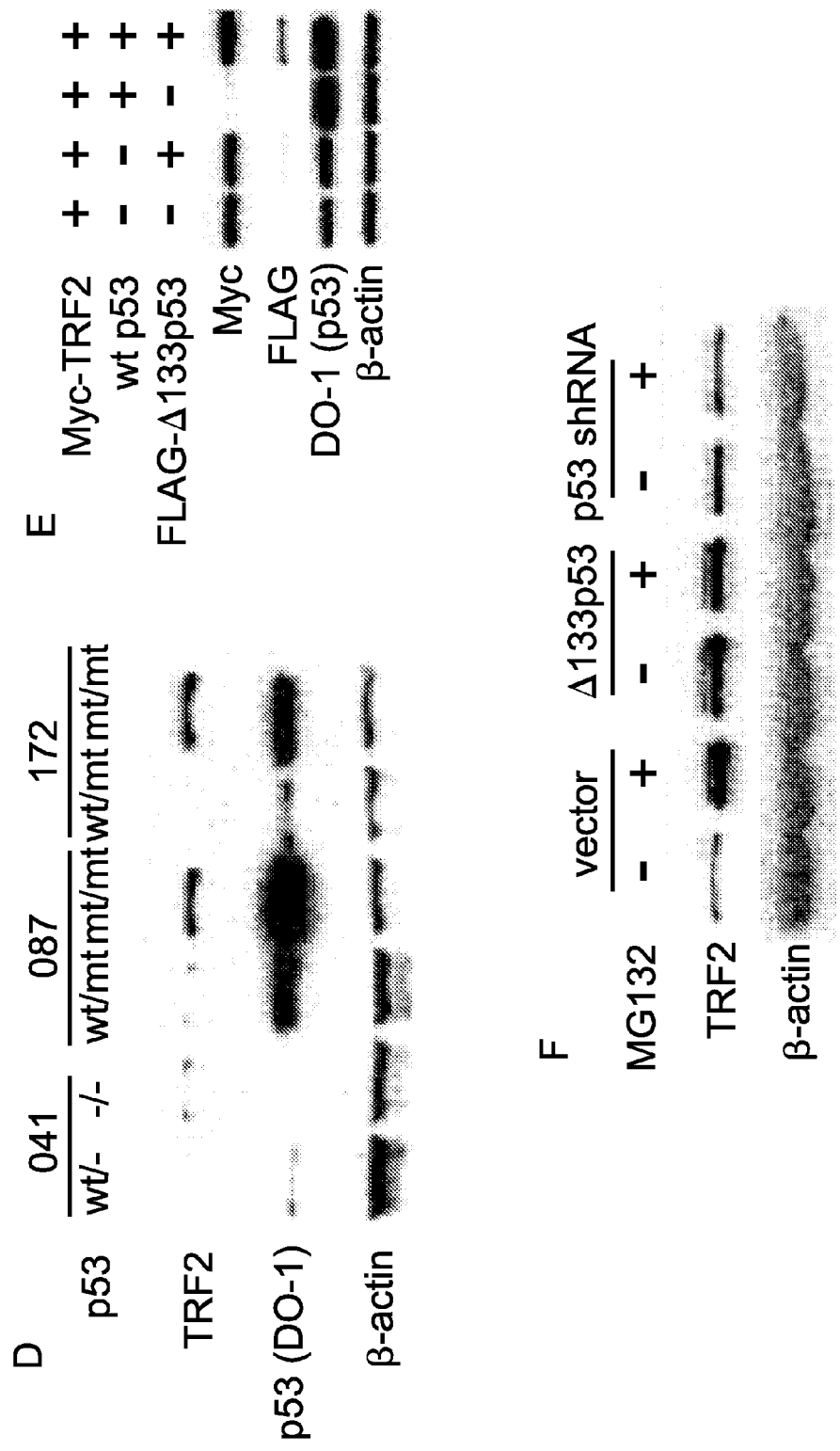
Figure 4:
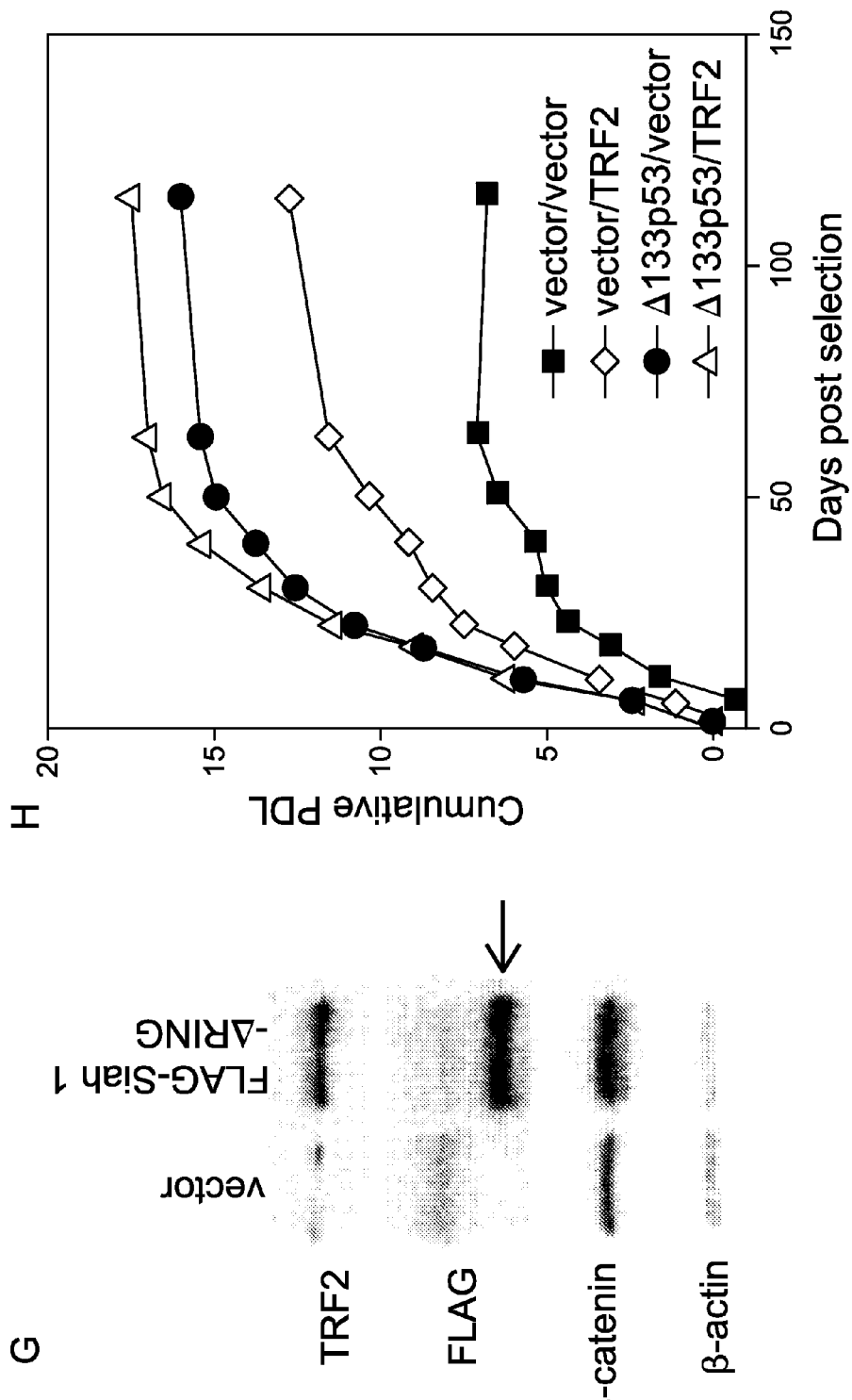
Figure 11:
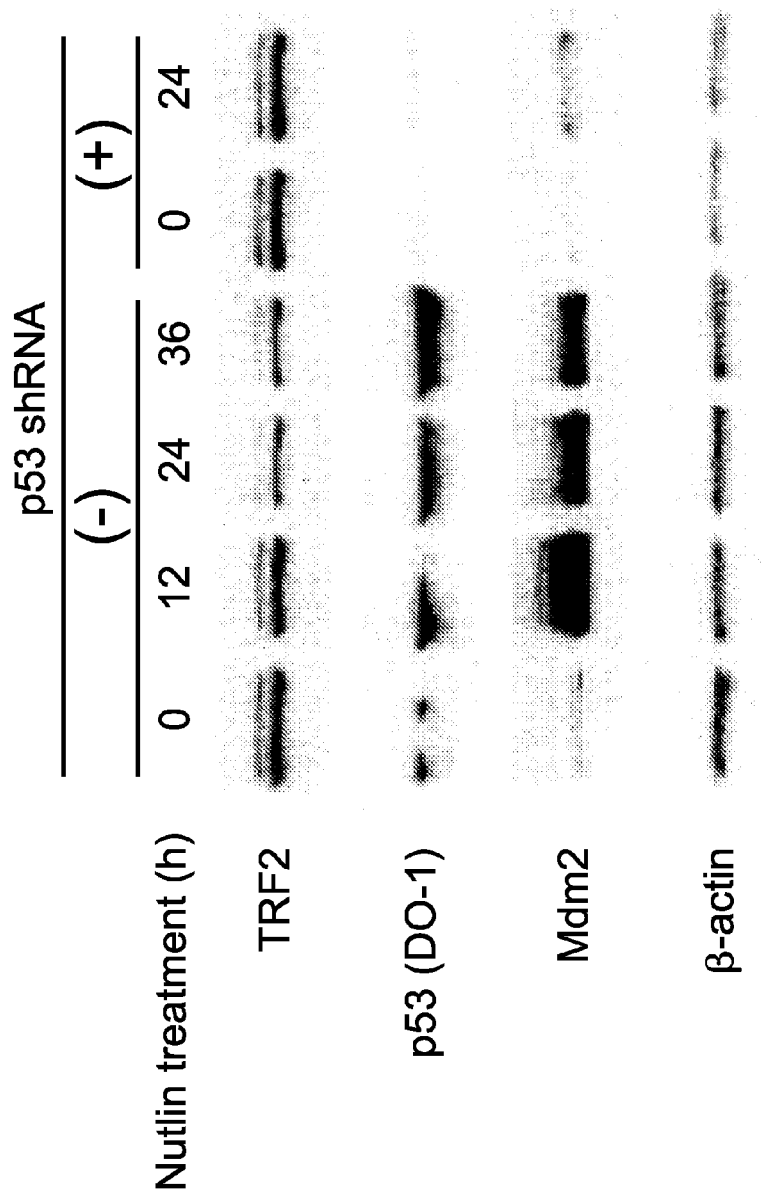
FIG. 11. Nutlin-3A downregulates TRF2 protein in a p53-dependent manner. hTERT/NHF cells with (+) or without (−) p53 shRNA were treated with 10 μM of Nutlin-3A (Cayman Chemical) for the indicated time period and examined for TRF2, p53 and MDM2 amounts in immunoblot analyses. β-actin was a loading control.

The overexpression of the telomere binding protein, TRF2, in cells with attenuated p53 function reset the senescence setpoint of telomeres to a shorter length and delayed the onset of cellular senescence (Karlseder, J. et al., *Science* 295:2446 (2002)). Therefore, we investigated whether Δ133p53 functions in part through the regulation of TRF2 expression. The upregulation of TRF2 was observed at all of the time points examined in the two fibroblast strains overexpressing Δ133p53 (FIG. 4A). We also found that shRNA knockdown of p53 induced the expression of TRF2 protein (FIG. 4B). Consistently, the small-molecule inhibitor of MDM2 (Nutlin-3a) (Buolamwini, J. K. et al., *Curr. Cancer Drug Targets* 5:57 (2005)), which increases p53 stability and transcriptional activity, resulted in a p53-dependent decrease in TRF2 expression (FIG. 11). These p53-dependent changes in TRF2 protein expression were inversely correlated with the changes in expression of the p53-regulated miR-34a: the shRNA knockdown of p53 and the treatment with Nutlin-3a reduced and induced miR-34a expression, respectively (FIG. 4C). However, a direct, miR-34a-targeted downregulation of TRF2 protein was unlikely because the retroviral overexpression of miR-34a resulted in no change in TRF2 expression (data not shown).

Figure 12:
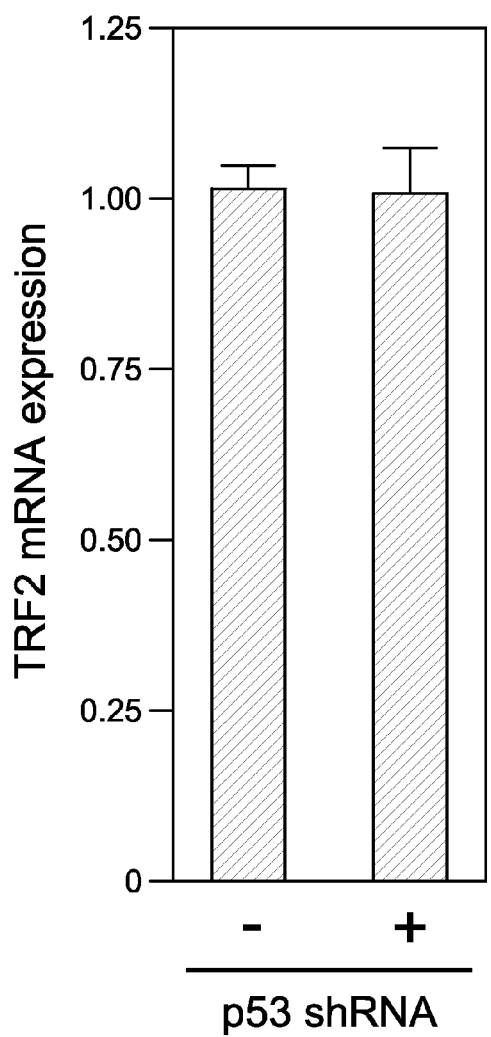
FIG. 12. The p53 knockdown-induced increase in TRF2 protein is not due to an increase in TRF2 mRNA. hTERT/NHF cells with (+) and without (−) p53 shRNA were examined for TRF2 mRNA expression by the real-time qRT-PCR (cat. no. 04689038001, Roche Applied Science).

In three fibroblast strains derived from Li-Fraumeni syndrome patients (FIG. 4D; MDAH041, MDAH087 and MDAH178) (Yin, Y. et al., *Cell* 70:937 (1992)), the loss of wt p53 allele (−/− and mt/mt) induced or enhanced the TRF2 expression, providing further evidence for the repression of TRF2 by wt p53. As shown in FIG. 4E, although Δ133p53 by itself did not affect the TRF2 expression, it had the ability to cancel the wt p53-mediated downregulation of TRF2. The treatment of human fibroblasts with a proteasome inhibitor MG-132 resulted in an increased TRF2 protein amount comparable with that in the p53-knocked-down and Δ133p53-expressing cells, while the same treatment did not lead to an additional increase in these cells (FIG. 4F). The increase in TRF2 protein expression by p53 knockdown occurred without a change in TRF2 mRNA expression (FIG. 12). These findings indicate that wt p53 negatively regulates TRF2 through a proteasomal degradation pathway and that the inhibition of wt p53 by shRNA knockdown and Δ133p53 expression stabilizes TRF2, providing a mechanistic, causative link between the p53 inactivation and the TRF2 upregulation in human cancers (Nakanishi, K. et al., *Clin. Cancer Res.* 9:1105 (2003); Nijjar, T. et al., *Oncogene* 24:3369 (2005)).

Figure 13:
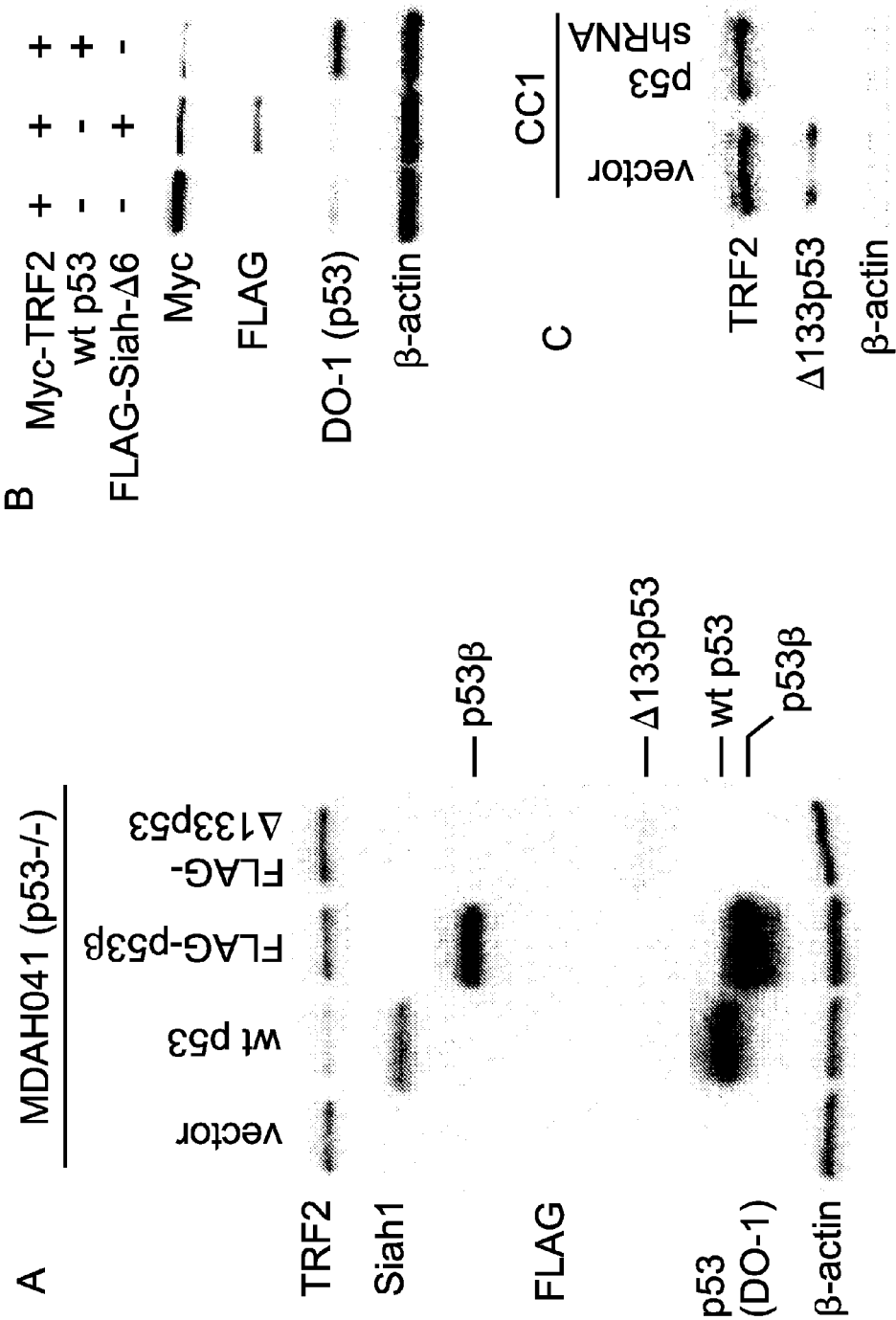
FIG. 13. Δ133p53 does not affect TRF2 expression in the absence of wt p53. (A) wt p53, FLAG-tagged p53β and FLAG-tagged Δ133p53 were retrovirally expressed in MDAH041 (p53−/−) fibroblasts. Neither p53β nor Δ133p53 changed TRF2 expression in these cells, while a significant decrease in TRF2 was observed with wt p53. The expression of Siah-1A was also examined and shown to be induced by wt p53. The expression of p53 isoforms was confirmed with anti-FLAG antibody and/or anti-p53 antibody (DO-1). (B) Downregulation of TRF2 by Siah-1A overexpression. Cells (293T) were retrovirally transduced with Myc-tagged TRF2, FLAG-tagged Siah1-Δ6 (a stable form of Siah-1A) (Tanikawa, J. et al., *J. Biol. Chem.* 279:55393 (2004)) and wt 53 as indicated. Anti-Myc, anti-FLAG and DO-1 antibodies were used in immunoblot analyses. (C) Δ133p53 was knocked down by p53 shRNA in CC1 cells, which express Δ133p53 but not wt p53 due to a genomic rearrangement (Horikawa, I. et al., *Hum. Mol. Genet.* 4:313 (1995)). No change in TRF2 expression was observed with a remarkable decrease in Δ133p53 (confirmed by immunoblot using MAP4). β-actin was a loading control in (A), (B) and (C).

We did not find a physical interaction between TRF2 and wt p53 in an immunoprecipitation (IP)-Western blot analysis (data not shown) and assumed that wt p53 regulates the TRF2 degradation through its transcriptional target involved in the proteasome pathway, rather than through a direct association with TRF2. MDM2, an E3 ubiquitin ligase well known to be transcriptionally upregulated by wt p53 (Rozan, L. M. et al., *Cell Death Differ.* 14:3 (2007)), was unlikely to be responsible for the wt p53-mediated TRF2 degradation, because the p53-dependent decrease in TRF2 expression occurred even when MDM2 was inactivated by its specific inhibitor Nutlin-3a (FIG. 11). Because TRF2 contains a Myb DNA-binding domain at the C-terminus (van Steensel, B. et al., *Cell* 92:401 (1998)), we focused on another E3 ubiquitin ligase transcriptionally induced by wt p53, Siah-1A (Matsuzawa, S. et al., *EMBO J.* 17:2736 (1998)) (FIG. 13A), which causes protein degradation through a Myb DNA-binding domain (Tanikawa, J. et al., *J. Biol. Chem.* 279:55393 (2004)). As shown in FIG. 4G, the accumulation of endogenous TRF2 was observed with the inhibition of endogenous Siah-1A activity by the dominant-negative mutant lacking the RING finger domain (Hu, G. et al., *Mol. Cell. Biol.* 19:724 (1999)). It was also shown that the overexpression of Siah-1A activity resulted in the downregulation of TRF2 (FIG. 13B). These results suggest that Siah-1A is responsible for the wt p53-induced TRF2 degradation.

The present data and our previous results (Bourdon, J. C. et al., *Genes Dev.* 19:2122 (2005)) suggest that Δ133p53 can inhibit the transcriptional activity of wt p53. The effects of Δ133p53 in the presence of wt p53, an in vivo physical interaction of wt p53 and Δ133p53 shown by an IP-Western experiment (data not shown), and the lack of the N-terminal transactivation domain in Δ133p53 all suggest the dominant-negative regulation of the wt p53 function by Δ133p53. By analogy to the gain-of-function activity of some mutant p53 proteins (Kastan, M. B. et al., *Nat. Cell Biol.* 9:489 (2007)), we investigated whether Δ133p53 also functions independently of wt p53. When Δ133p53 was overexpressed in the Li-Fraumeni syndrome fibroblast MDAH041 null for p53 (homozygous for a frameshift mutation at codon 184) (Yin, Y. et al., *Cell* 70:937 (1992)), no significant change in TRF2 expression was observed (FIG. 13A). The shRNA knockdown of Δ133p53 in CC1 cells, which express Δ133p53, but not wt p53, due to the homozygous genomic deletion (Horikawa, I. et al., *Hum. Mol. Genet.* 4:313 (1995)), resulted in no change in TRF2 expression (FIG. 13C) or cell proliferation (data not shown). Thus, there is no evidence for a gain-of-function activity of Δ133p53.

Discussion

This study provides a novel mechanistic link among p53, telomeres and cellular senescence in humans by establishing the causative role of p53 in the regulation of TRF2, a key component of the telomere-binding protein complex (Verdun, R. E. et al., *Nature* 447:924 (2007)). Our data show that, in addition to the involvement of p53 in the ATM-p53-p21$^{WAF1}$ pathway (Herbig, U. et al., *Mol. Cell.* 14:501 (2004)) and the miR-34a-mediated pathway (Chang, T. C. et al., *Mol. Cell.* 26:745 (2007); He, L. et al., *Nature* 447:1130 (2007); Raver-Shapira, N. et al., *Mol. Cell.* 26:731 (2007)), which could signal DNA damage at telomeres to the cell cycle control, p53 functions to directly regulate the structure and function of telomeres through the TRF2 regulation. This represents a novel p53 regulation mode of cellular proliferation and senescence. In agreement with this notion, the TRF2 overexpression extended the cellular replicative lifespan, as previously reported (Karlseder, J. et al., *Science* 295:2446 (2002)), but to a lesser extent than the Δ133p53 overexpression, and the co-overexpression of TRF2 and Δ133p53 had a minimal additional effect to the overexpression of Δ133p53 alone (FIG. 4H). In summary, this study indicates that Δ133p53 functions as a physiological regulator of cellular senescence by modulating multiple, wt p53-regulated signaling pathways to cellular senescence. Given that TRF2 inhibits the ATM-initiated DNA damage signaling at telomeres (Denchi, E. L. et al., *Nature* 448:1068 (2007)), our data also suggest that a feedback loop involving ATM, p53 and TRF2 may amplify the p53-mediated and DNA damage-induced cellular responses.

A novel mechanism for inactivating the tumor suppressor functions of wt p53 was characterized in this work: the inhibition by its own natural isoform. Similar to the viral oncoproteins, such as HPV E6 and SV40 T antigen, in in vitro cell transformation models (Harley, C. B. et al., Gerontol. 27:375 (1992)), Δ133p53 inhibits the wt 53 activity to extend in vitro replicative lifespan of normal human cells. Our preliminary findings showed high levels of Δ133p53 expression in some cancer cell lines with wild-type p53 retained (Fujita, K. et al., unpublished observations), suggesting that Δ133p53 may also play a critical role in human carcinogenesis. Even in the absence of p53 gene mutations, the upregulation of Δ133p53 could counteract the wt p53 activity, allowing the premalignant cells to bypass the senescence checkpoint and acquire oncogenic mutations during the extended replicative lifespan.

The senescence-associated p53 isoform switching revealed herein provide the basis for a new strategy for the p53-based manipulation of aging and carcinogenesis. The detection of highly expressed Δ133p53 in the absence of a p53 mutation in cancer diagnosis identifies cases in which the specific inhibition of Δ133p53 can activate p53-dependent cellular senescence, and therefore, will be of great therapeutic value.

Example 6

Δ133p53, p53β, and a p53-Regulated MicroRNA, miR-34a are Regulators of Replicative Cellular Senescence The finite replicative potential of normal human cells leads to an irreversible proliferation arrest called replicative cellular senescence, which constitutes a critical mechanism for tumour suppression in vivo and may contribute to organismal ageing. p53 plays a central role in the regulation of replicative senescence. The human p53 gene encodes, in addition to full-length p53, several truncated p53 isoforms[5], whose roles are poorly understood. Here, the inventors show that the p53 isoforms (Δ133p53 and p53β and a p53-induced microRNA (miR-34a)[6] are involved in p53-mediated replicative senescence. A switching in endogenous protein expression from Δ133p53 to p53β was associated with replicative senescence, but not premature senescence induced by either oncogene expression or acute telomere dysfunction, in normal human fibroblasts. The endogenous expression of miR-34a was also upregulated at replicative senescence. The siRNA-mediated knockdown of endogenous Δ133p53 induced cellular senescence, which was associated with the upregulation of p53 transcriptional targets p21$^{WAF1}$ and PAI-1[7]. Conversely, the antisense inhibition of endogenous miR-34a delayed the onset of replicative senescence. In the overexpression experiments, p53β cooperated with full-length p53 to accelerate cellular senescence, while Δ133p53 extended the cellular replicative lifespan with the repression of miR-34a, further supporting the roles of the p53 isoforms and miR-34a in cellular senescence. It is also discovered that freshly isolated, human senescent T lymphocytes (CD8+, CD28− and CD57+ [8, 9]; and with an increased senescence marker HP1-γ[10, 11]) and colon adenoma tissues with senescence markers, p16$^{INK4A}$ and senescence-associated β-galactosidase[12, 13], expressed elevated levels of p53β and reduced levels of Δ133p53. Senescence-associated p53 isoform switching occurs during both physiologically and pathologically induced senescence, and in various human cell types in vitro and in vivo.

Our recent progress provides evidence for the p53 isoform switching in humans in vivo. We examined senescent CD8+ T lymphocytes, which are marked by CD28−/CD57+ and accumulate as humans age and in HIV (human immunodeficiency virus)-infected persons (Effros et al., Immunol. Rev. 205: 147-57, 2005; Brenchley et al., Blood 101: 2711-20, 2003) and observed elevated levels of p53β and reduced levels of Δ133p53 in these senescent T cells. Human colon adenomas, premalignant tumors associated with accelerated senescence (Kuilman et al., Cell 133: 1019-31, 2008; Collado et al., Nature 436; 642, 2005), also had elevated levels of p53β and reduced levels of Δ133p53. These in vivo results reproduce the findings from cultured fibroblasts in vitro and indicate a therapeutic application of the p53 isoforms.

Normal human somatic cells can undergo only a limited number of cell divisions, eventually reaching an irreversible proliferation arrest called replicative cellular senescence[2, 9]. Various cellular stresses (e.g., oncogene activation, oxidative stress and DNA damage) can also induce cellular senescence[1-3]. Whether replicatively induced or prematurely stress-induced, cellular senescence constitutes a critical mechanism for tumour suppression in vivo and may contribute to organismal ageing[1-3]. The p53 signalling pathway plays a central role in the regulation of cellular senescence[2, 3]. Although the alternative mRNA splicings and the use of an alternative promoter in the human p53 gene produce several truncated p53 isoforms[4], their regulation and function are poorly understood. Here, we examine the expression profiles of two p53 isoforms (p53β and Δ133p53, for which the specific antibodies were raised; see below) during cellular senescence in vitro and in vivo, their biological activities in regulating cellular senescence, and the role of miR-34a[5] as a downstream effector of p53-mediated senescence.

Figure 14:
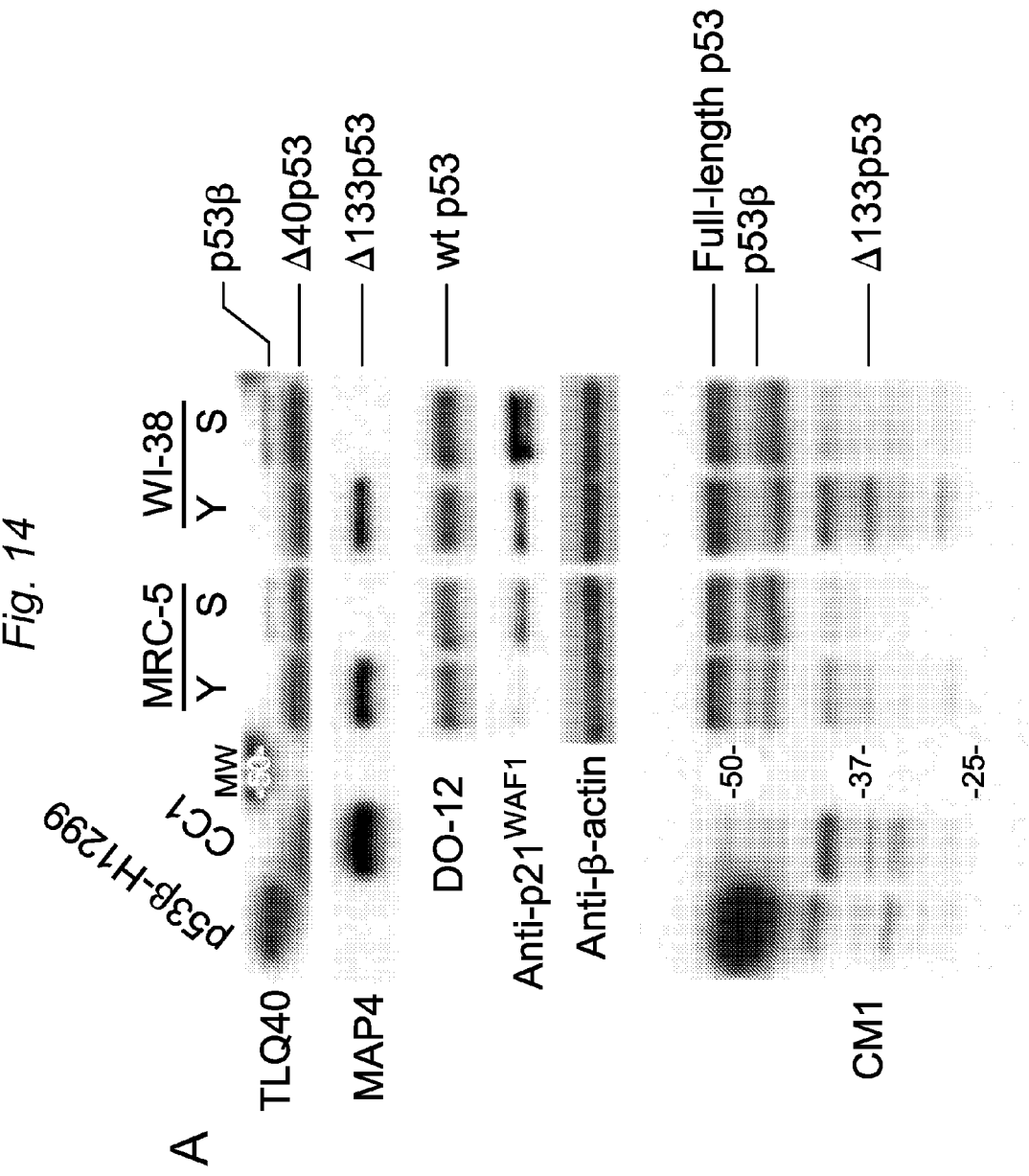
FIG. 14. Replicative senescence-associated changes in expression of endogenous p53 isoforms and p53-regulated microRNA-34a. a, Induction of p53β and repression of Δ133p53 at replicative senescence. The immunoblot analyses were performed in early-passage (Y) and senescent (S) human fibroblast strains MRC-5 and WI-38. The examined passage numbers were 30 (Y) and 65 (S) for MRC-5; and 30 (Y) and 58 (S) for WI-38. TLQ40, an antibody detecting p53β isoforms; MAP4, an antibody detecting Δ133p53; DO-12, an antibody used to detect full-length p53; CM1, an antibody used to simultaneously detect full-length p53, p53β and Δ133p53. Δ40p53β was a predominant form detected by TLQ40 and was constitutively expressed in both early-passage and senescent cells. p21$^{WAF1}$ expression was also examined. β-actin was a loading control. H1299 cells overexpressing p53β and CC1 cells were used as the positive controls for p53β and Δ133p53, respectively. b, miR-34a expression during replicative senescence. The same set of MRC-5 and WI-38 fibroblasts as used in a were examined for miR-34a expression by real-time qRT-PCR. The data were normalized with control RNU66 expression and shown as the relative values (mean±s.d. from triplicate sample). Three independent experiments were carried out and the reproducible results were obtained. *, p<0.001. **, p<0.01. c and d, Extension of cellular replicative lifespan by the inhibition of miR-34a expression. Late-passage MRC-5 fibroblasts (at passage 58) were transfected with the antisense oligonucleotide against miR-34a and the control oligonucleotide (EGFP). The effectiveness of the antisense miR-34a was confirmed by the real-time qRT-PCR (error bars represent s.d. from triplicate sample) (c). The transfection was repeated every 4 days and the cumulative population doublings (PDL) were examined (d). e, Knockdown of miR-34a expression partially inhibits Nutlin-3A-induced senescence. hTERT-immortalized human fibroblasts (hTERT/NHF) were transfected with the antisense miR-34a or control oligonucleotide, and then induced to senesce by treatment with 10 μM of Nutlin-3A for 72 h. Summary of senescence-associated β-galactosidase (SA-β-gal) assay is shown. The data (mean±s.d.) were from three independent experiments. *, p<0.05.
Figure 14:
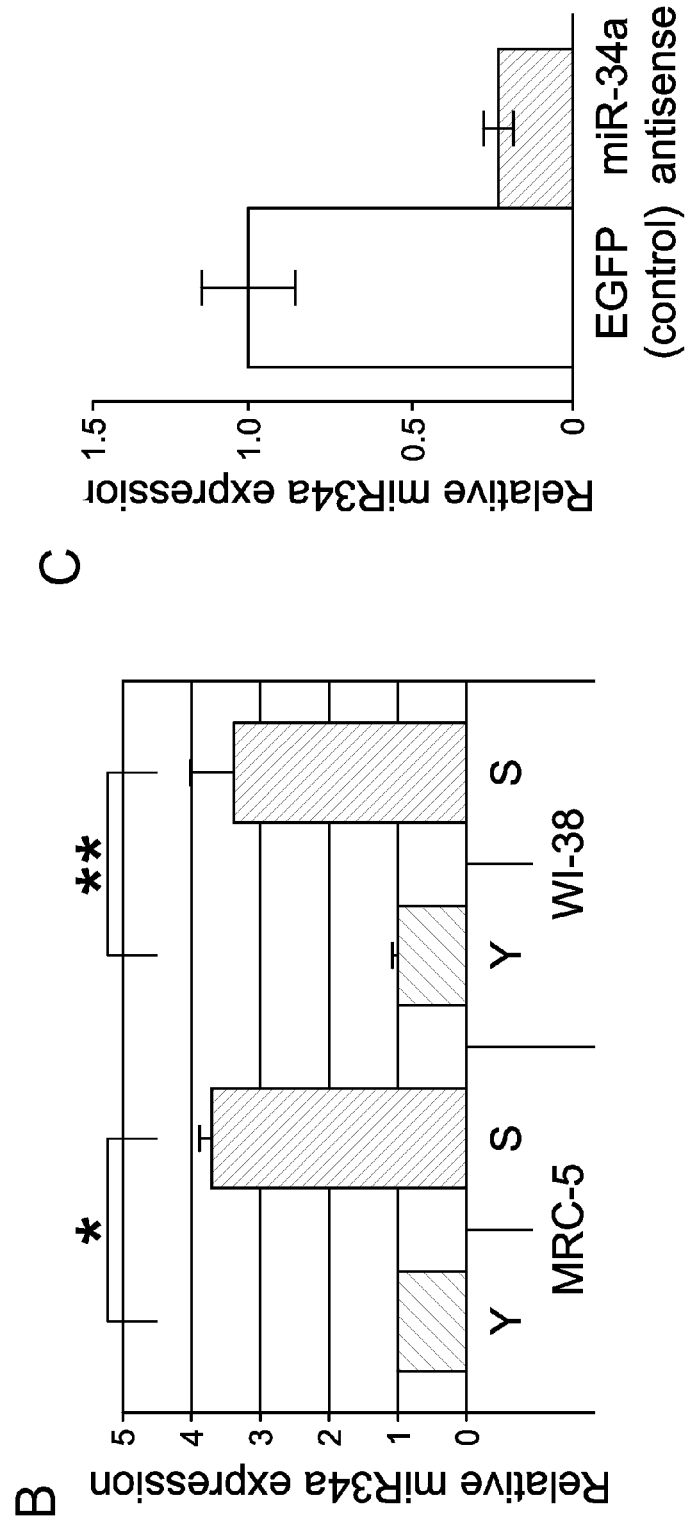
Figure 14:
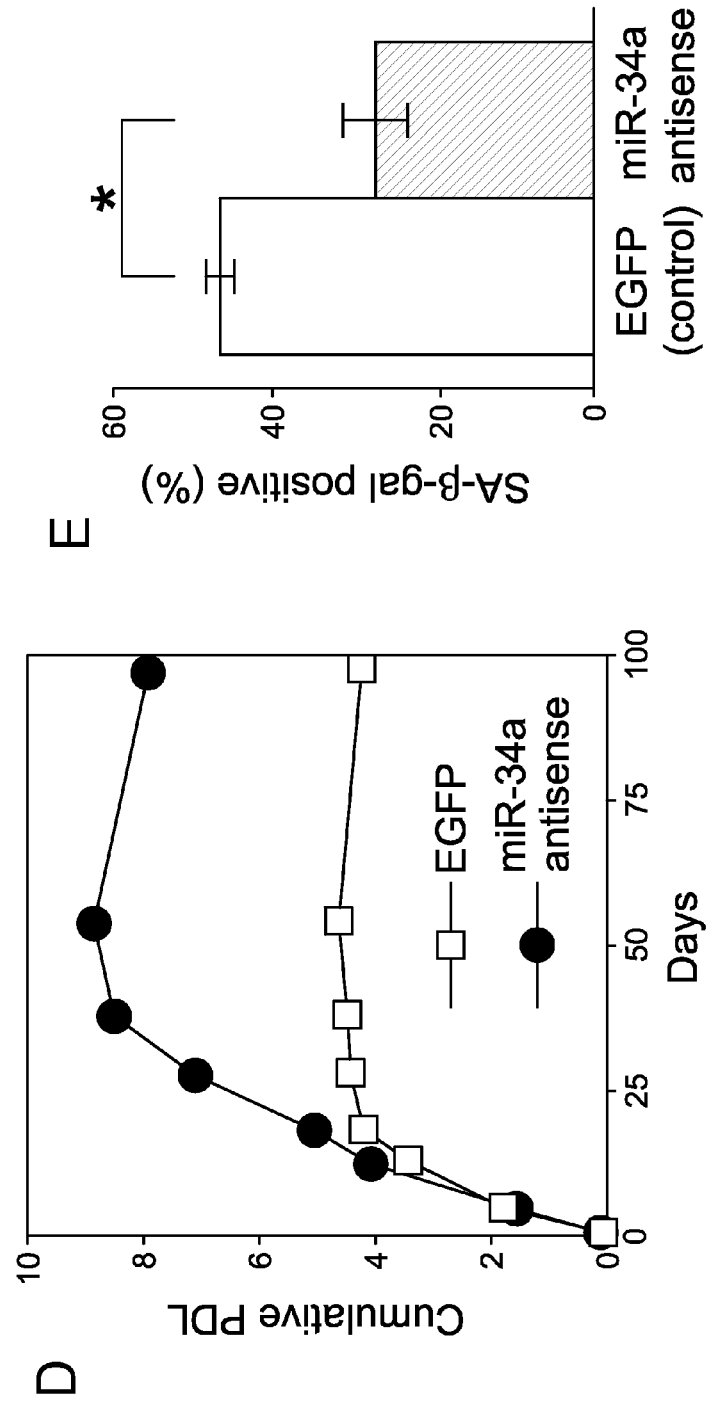
Figure 18:
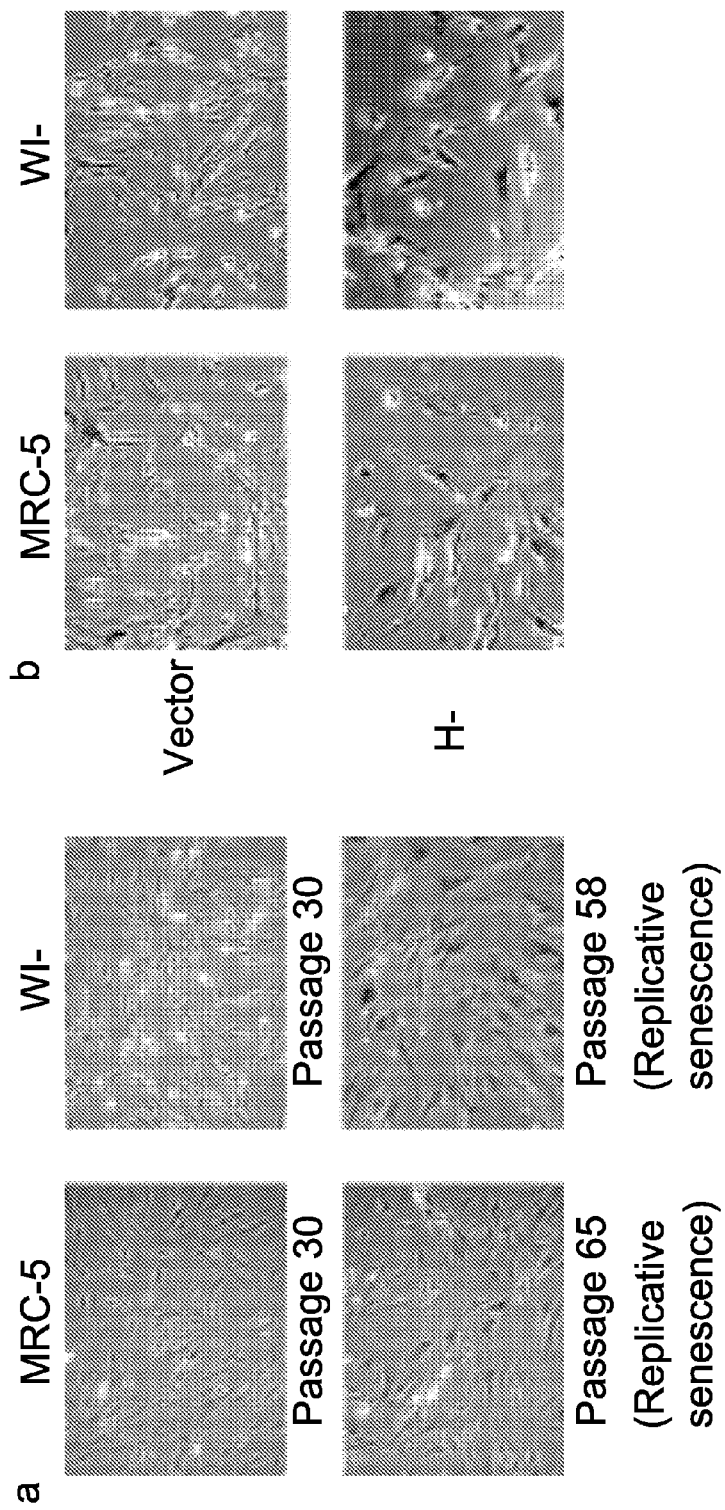
FIG. 18. SA-β-gal staining in replicative senescence and oncogene-induced premature senescence. a, MRC-5 and WI-38 fibroblasts at early passage (upper panels) and at replicative senescence (lower panels). b, MRC-5 and WI-38 retrovirally transduced with vector control (upper panels) and pBabe-Puro ras (H-RasV12) (Serrano et al. Cell 88, 593-602 (1997)) (lower panels). Note that premature senescence by POT1 knockdown was induced and confirmed by SA-β-gal staining as described in our previous study (Yang et al. Cancer Res. 67, 11677-11686 (2007)). The dominant-negative TRF2-induced senescence was also as previously described by the present inventors (Yang et al. Mol. Cell. Biol. 25, 1070-1080 (2005)) and others (van Steensel et al. Cell 92, 401-413 (1998)).
Figure 19:
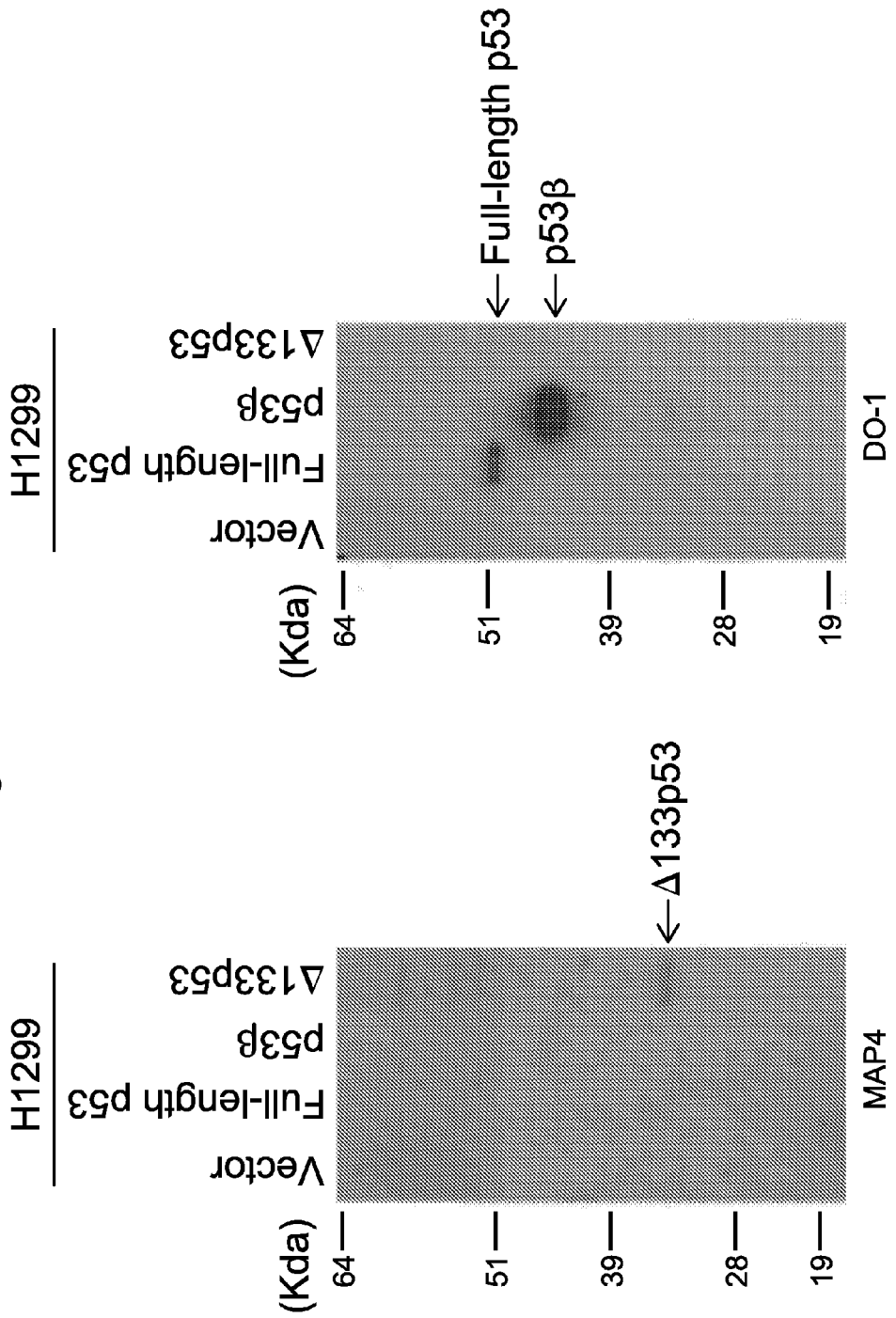
FIG. 19. MAP4 specifically recognizes Δ133p53. H1299 cells (p53-null) transfected with the expression vector for wild-type (wt) p53, p53β or Δ133p53 were analyzed in immunoblot using MAP4 (left) and DO-1 (right) antibodies. MAP4 detects Δ133p53, but not wt p53 or p53β.
Figure 20:
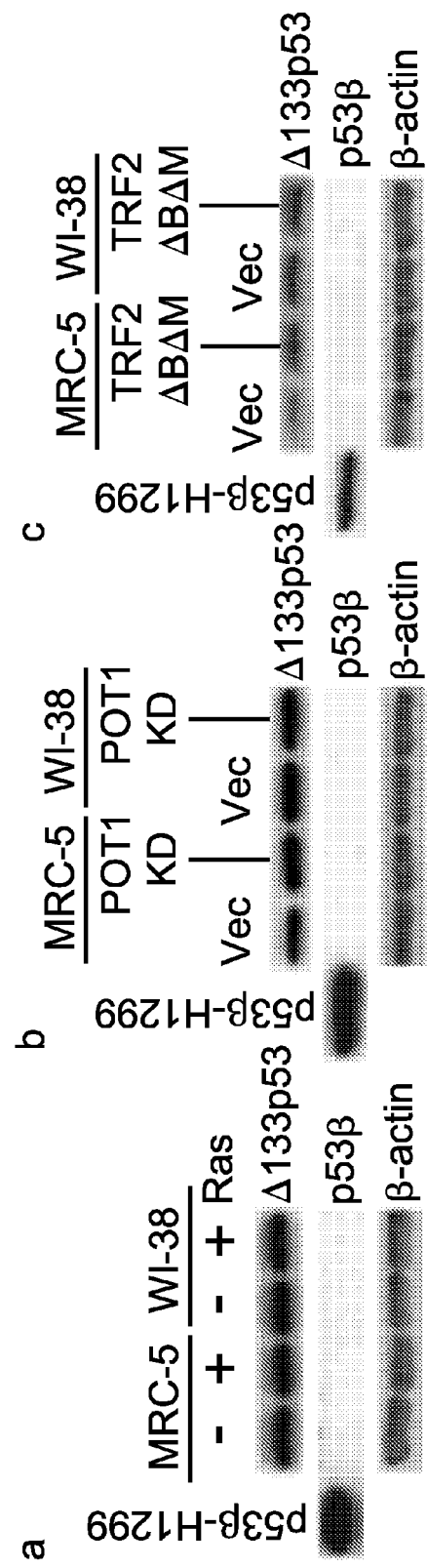
FIG. 20. p53 isoform switching does not occur with premature senescence. Δ133p53 and p53β expression in oncogene-induced senescence (overexpression of H-RasV12) (Serrano et al. Cell 88, 593-602 (1997)) (a) and premature senescence with acute telomere dysfunction induced by shRNA knockdown of POT1 (Yang et al. Cancer Res. 67, 11677-11686 (2007)) (b) or overexpression of a dominant-negative TRF2 mutant (Yang et al. Mol. Cell. Biol. 25, 1070-1080 (2005); van Steensel et al. Cell 92, 401-413 (1998)) (c). Early-passage MRC-5 and WI-38 (at passage 32) were used. H1299 cells overexpressing p53β was the positive control for p53β. β-actin was a loading control.
Figure 35:
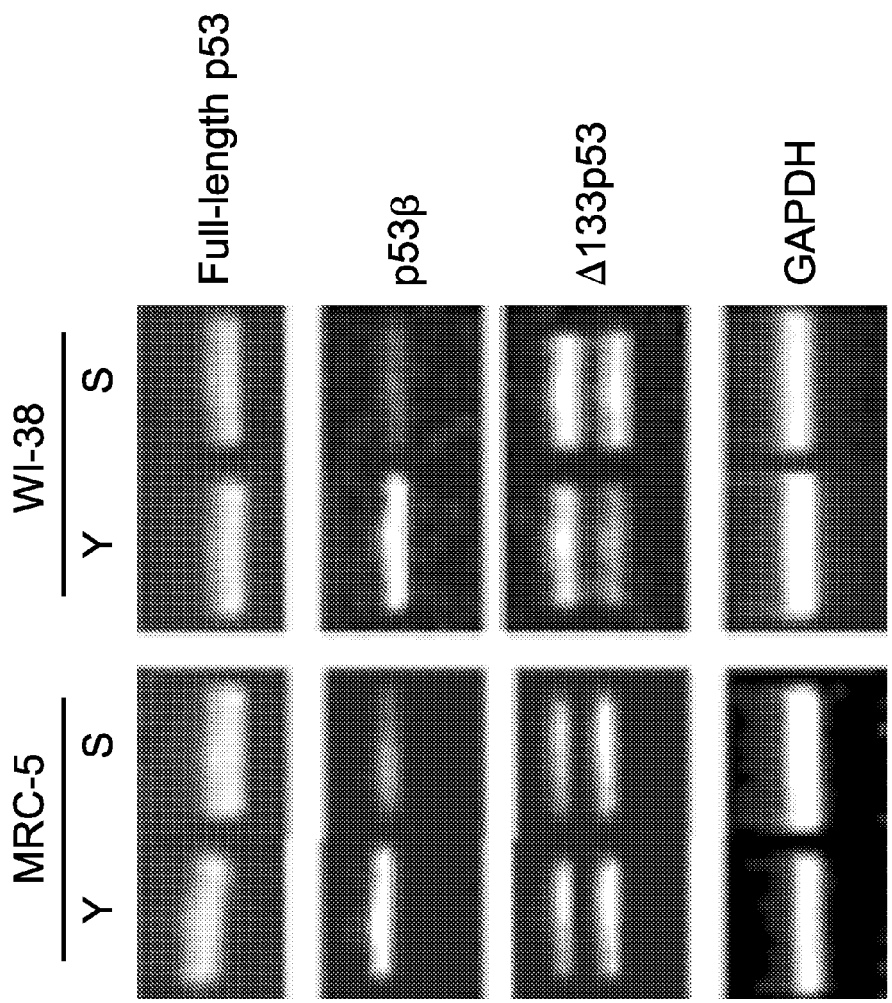
FIG. 35. mRNA expression analysis of p53 isoforms in human fibroblasts. The same sets of cells as in FIG. 14a were analyzed by RT-PCR. The primers to amplify wt p53 were: 5'-CTC ACC ATC ATC ACA CTG GAA-3' (SEQ ID NO:6) and 5'-TCA TTC AGC TCT CGG AAC ATC-3' (SEQ ID NO:7). The primers specifically detecting the alternative splicing for p53β were: 5'-CTT TGA GGT GCG TGT TTG TGC-3' (SEQ ID NO:8)and 5'-TTG AAA GCT GGT CTG GTC CTG A-3'(SEQ ID NO.:9). The primers specifically amplifying Δ133p53 mRNA transcribed from the promoter in intron 4 were: 5'-TGG GTT GCA GGA GGT GCT TAC-3' (SEQ ID NO:10)and 5'-CCA CTC GGA TAA GAT GCT GAG G-3' (SEQ ID NO:11). The lower bands correspond to the reported Δ133p53 sequences (GenBank DQ186650). The upper bands are from mRNA with intron 5 unspliced. GAPDH was amplified as a control as previously described (Horikawa and Barrett *Mol. Carcinog.* 22, 65-72 (1998)).

The endogenous expression of two major p53 isoforms, p53β and Δ133p53, was examined in normal human fibroblast strains (MRC-5 and WI-38) at early passage (both strains at passage number 30, Y in FIG. 14a) and at replicative senescence (MRC-5 at passage 65 and WI-38 at passage 58, S in FIG. 14a) (FIG. 18a). p53β, detected by the TLQ40 antibody[5], lacks the C-terminal oligomerisation domain due to an alternative RNA splicing[5]; and Δ133p53, detected by the MAP4 antibody (FIG. 19), lacks the N-terminal transactivation and proline-rich domains due to the transcription from an alternative promoter in intron 4[5]. While the expression of full-length p53 (detected by DO-12) showed no changes during replicative senescence, p53β was specifically detected when the cells became senescent. In remarkable contrast, the expression of Δ133p53 was markedly diminished in the senescent cells. The immunoblot analysis using CM1 antibody showed that p53β and Δ133p53 were expressed less abundantly than full-length p53 but still at readily detectable levels (FIG. 14a). Premature senescence induced by oncogenic Ras (FIG. 18b) or acute telomere dysfunction (by knockdown of POT1[14] or overexpression of a dominant-negative TRF2 mutant[15]) was not associated with either induced p53β or diminished Δ133p53 (FIG. 20), suggesting that the p53 isoform switching is specific to replicative cellular senescence. The RT-PCR analyses showed that the p53 isoform switching at replicative senescence was not due to a change in mRNA expression (FIG. 35).

Figure 21:
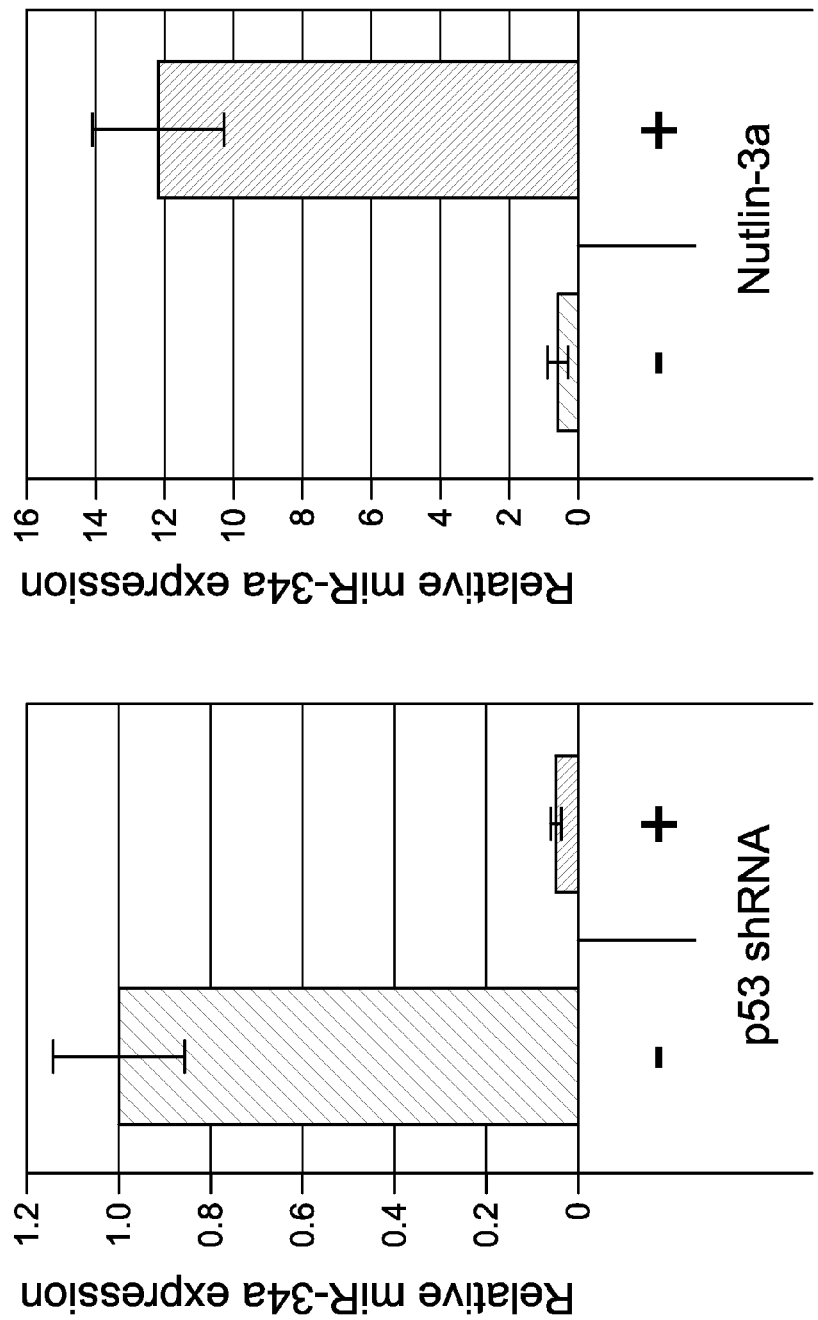
FIG. 21. miR-34a expression is p53-dependent. hTERT-immortalized human fibroblasts (hTERT/NHF) (Sengupta et al. EMBO J. 22, 1210-1222 (2003)) transduced with the shRNA knockdown vector targeting p53 (Brummelkamp and Agami Science 296, 550-553 (2002)) (left) or treated with 10 μM of Nutlin-3a for 36 h (Kumamoto et al. Cancer Res. 68, 3193-3203 (2008)) (right) were examined for miR-34a expression, as in FIG. 14b. The data (mean±s.d. from triplicate sample) is shown as the relative expression level to control cells (–).

In addition to the upregulation of p21$^{WAF1}$ (FIG. 14a), which mediates p53-induced senescence[16, 17], the replicatively senescent MRC-5 and WI-38 fibroblasts expressed increased amounts of miR-34a (FIG. 14b), a microRNA that is transcriptionally activated by full-length p53[6, 18] (FIG. 21) and has an ability to induce cellular senescence when overexpressed[6, 19]. To examine the role of endogenous miR-34a in cellular senescence, an antisense oligonucleotide was developed to knockdown the endogenous expression of miR-34a (FIG. 14c). The antisense inhibition of miR-34a in late-passage human fibroblasts (MRC-5 at passage 58) extended their replicative lifespan by approximately five population doublings (PDLs) (FIG. 14d). The Nutlin-3A-induced senescence, which is dependent on the accumulation and activation of endogenous p53[20], was significantly but partially (by approximately 50%) inhibited by the antisense knockdown of endogenous miR-34a (FIG. 14e). These findings provide the first evidence that the endogenous levels of miR-34a, as one of the downstream effectors of p53, plays a physiological role in the regulation of cellular senescence.

Figure 15:
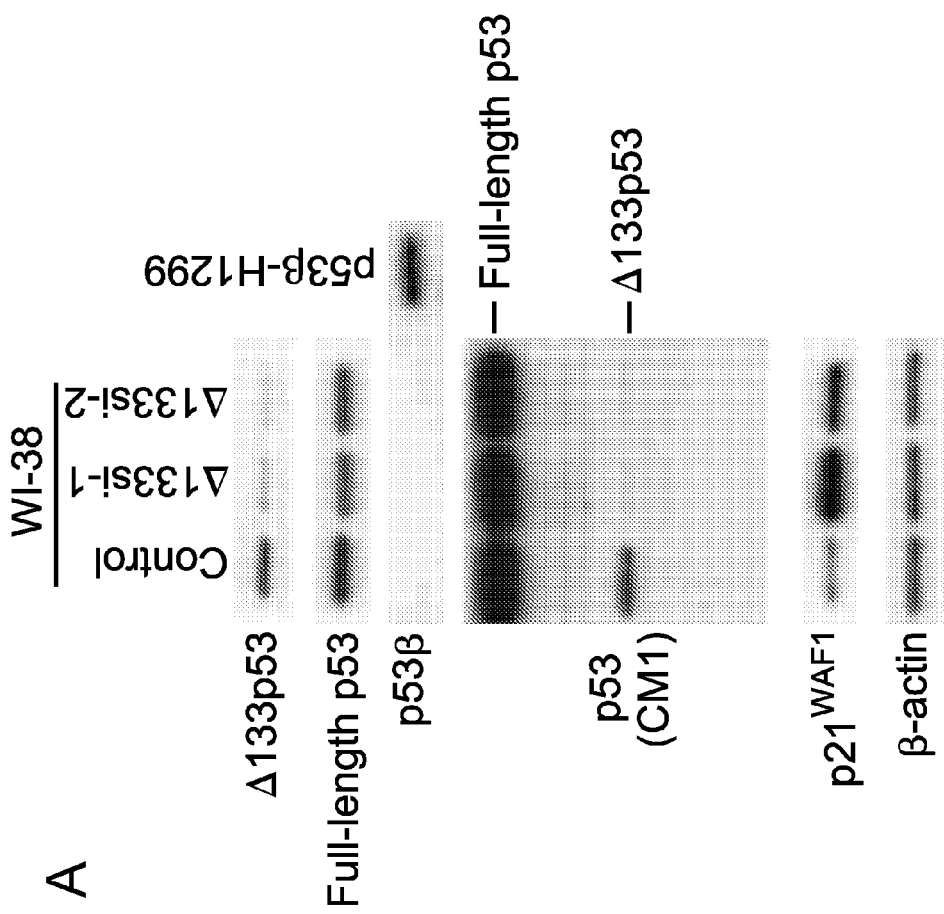
FIG. 15. Knockdown of endogenous Δ133p53 induces cellular senescence. Early-passage WI-38 fibroblasts (at passage 30) were transfected with siRNAs targeting Δ133p53 (Δ133si-1 and Δ133si-2) and a control oligonucleotide twice (at day 1 and day 4), and at day 7 were used for immunoblot analyses (a) and examined for SA-β-gal activity (b and c), bromo-deoxyuridine (BrdU) incorporation (d) and PAI-1 (plasminogen activator inhibitor-1) expression (e). a, siRNA-mediated repression of Δ133p53. Expressions of full-length p53 (DO-1 antibody), Δ133p53 (MAP4 antibody), p53β (TLQ40 antibody) and p21$^{WAF1}$ were examined. The expression levels of full-length p53 and Δ133p53 were also confirmed by the CM1 antibody. β-actin was a loading control. H1299 expressing p53β was the positive control for TLQ40. b, Representative pictures of SA-β-gal staining. c, Summary of SA-β-gal assay. The data (mean±s.d.) were from three independent experiments. *, p<0.01. d, BrdU incorporation assay. The number of BrdU-positive cells/the total number of cells examined (at least 100 cells for each well) was recorded. Data are mean±s.d. from triplicate wells. *, p<0.05. **, p<0.01. e, The real-time qRT-PCR assay of PAI-1. The relative expression levels of PAI-1 mRNA are shown. Error bars represent s.d. from triplicate sample. *, p<0.05. **, p<0.01.
Figure 15:
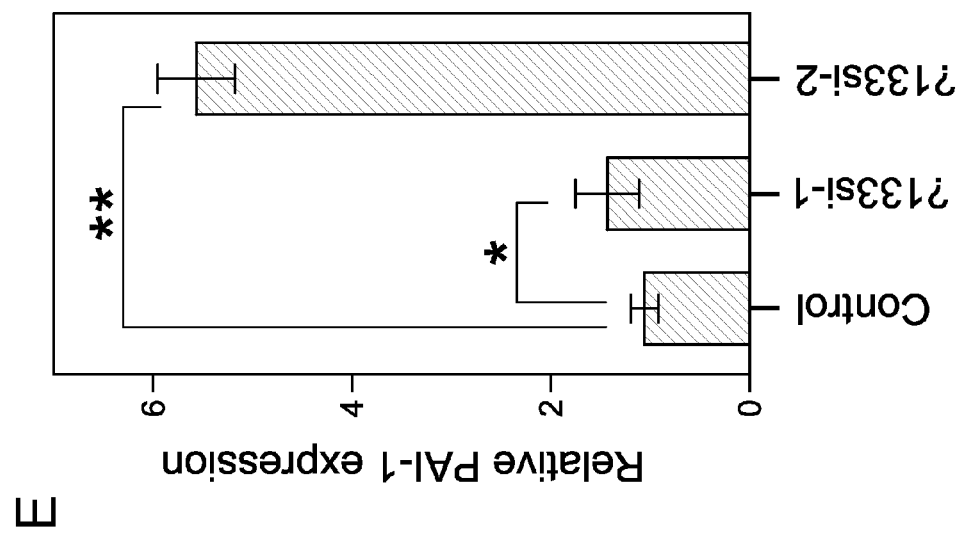
Figure 22:
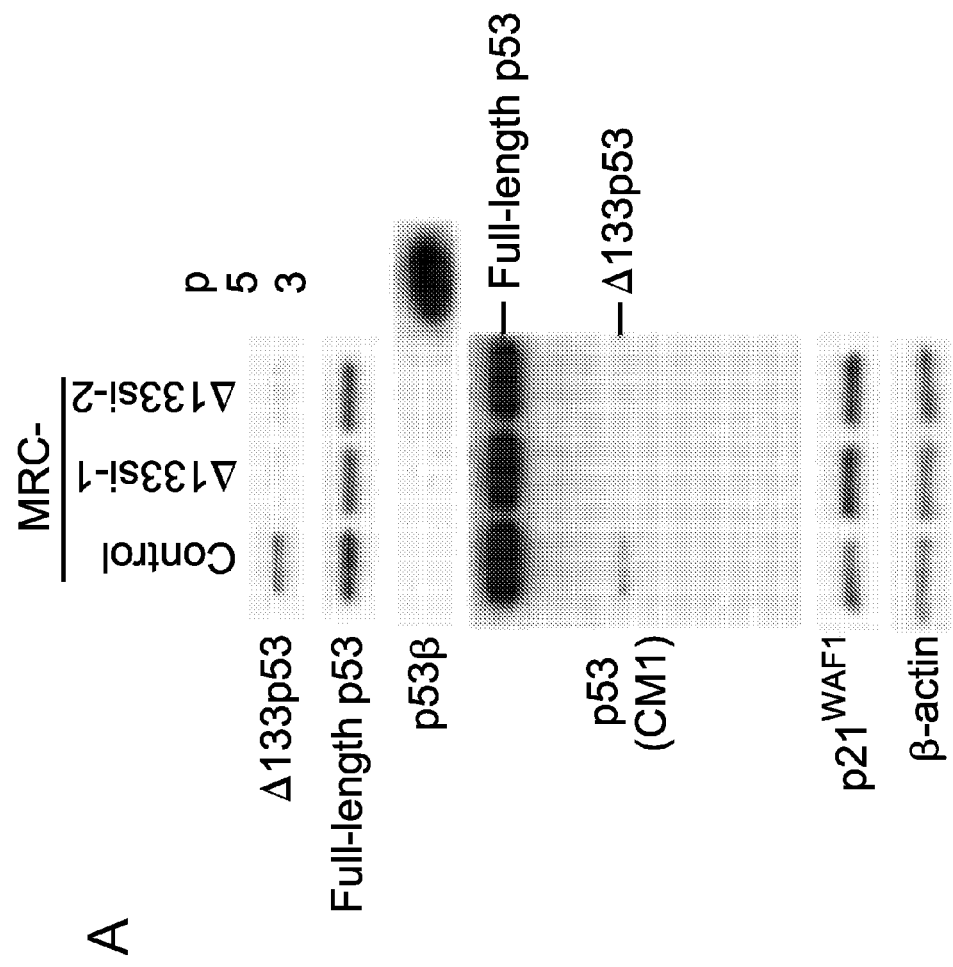
FIG. 22. Knockdown of endogenous Δ133p53 induces cellular senescence. Early-passage MRC-5 fibroblasts (at passage 32) were transfected with the siRNAs targeting Δ133p53 (Δ133si-1 and Δ133si-2) and a control oligonucleotide and examined in immunoblot analyses (a), SA-β-gal assay (b) and BrdU incorporation assay (c), as performed in FIG. 2. *, p<0.001.
Figure 22:
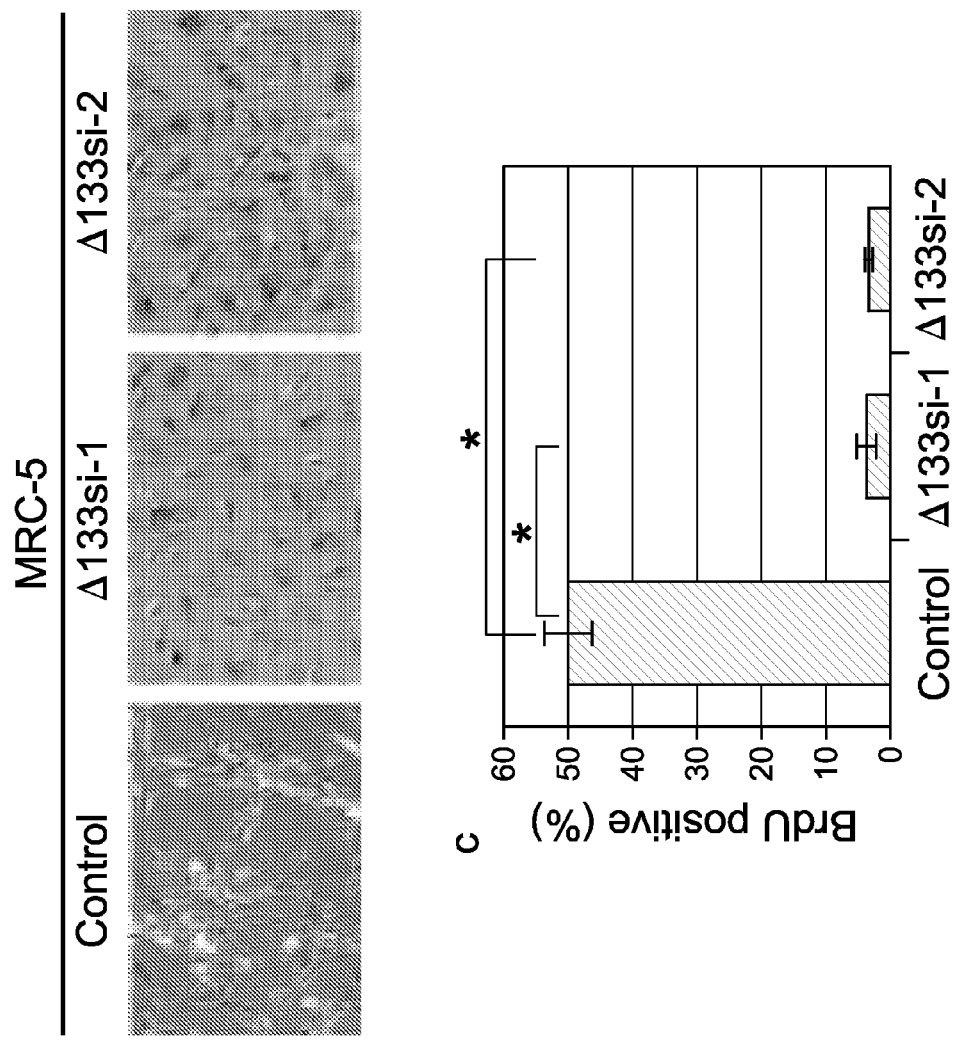
Figure 23:
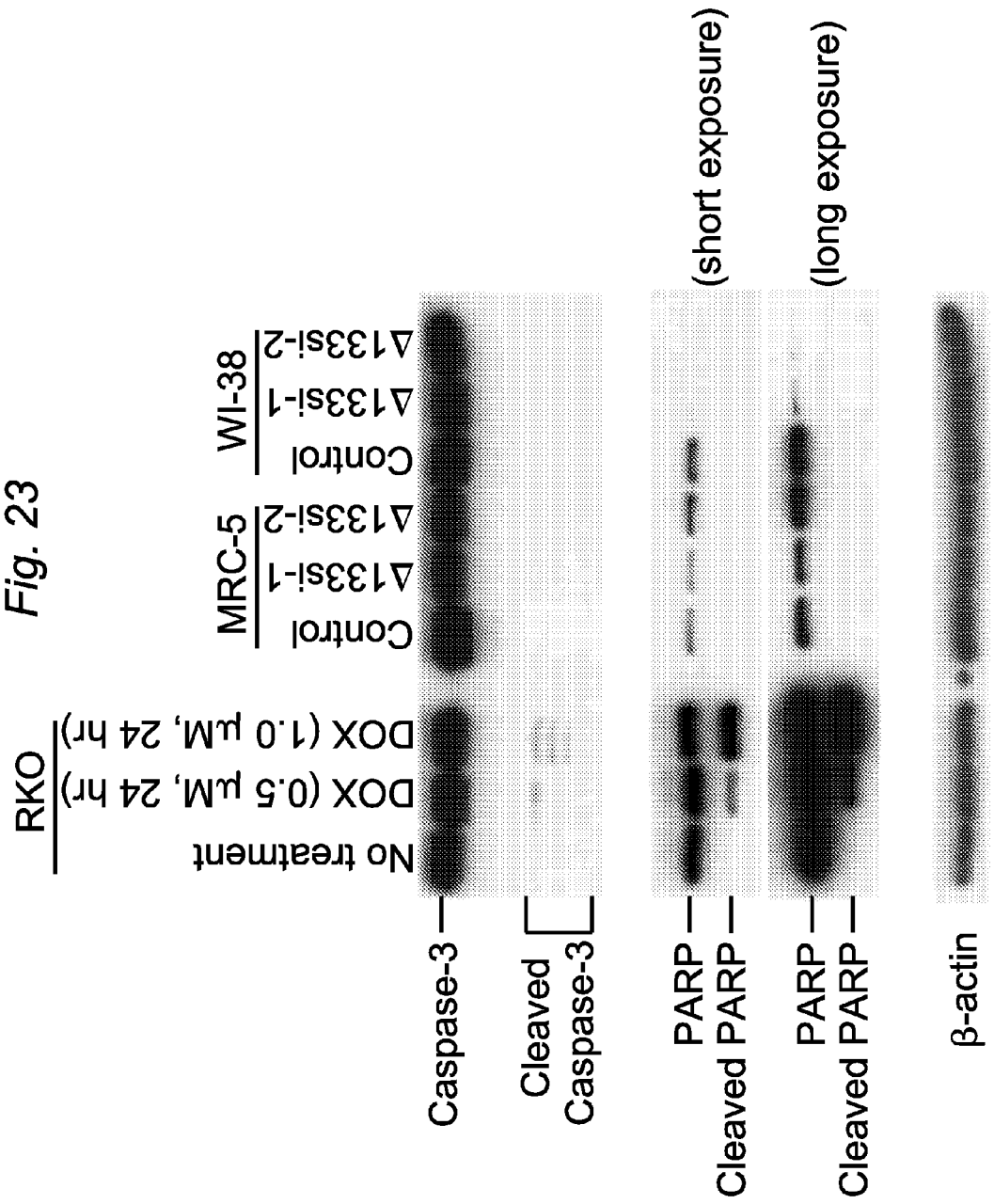
FIG. 23. Δ133p53 knockdown does not induce apoptosis in human fibroblasts. MRC-5 and WI-38 transfected with control, Δ133si-1 and Δ133 si-2 oligonucleotides were examined for caspase-3 (top) and PARP (middle, short and long exposure) in immunoblot. RKO cells treated with doxorubicin (DOX) were included as the positive control showing apoptosis. β-actin was a loading control (bottom). No cleaved caspase-3 or PARP was observed in Δ133p53-knocked-down fibroblasts.
Figure 24:
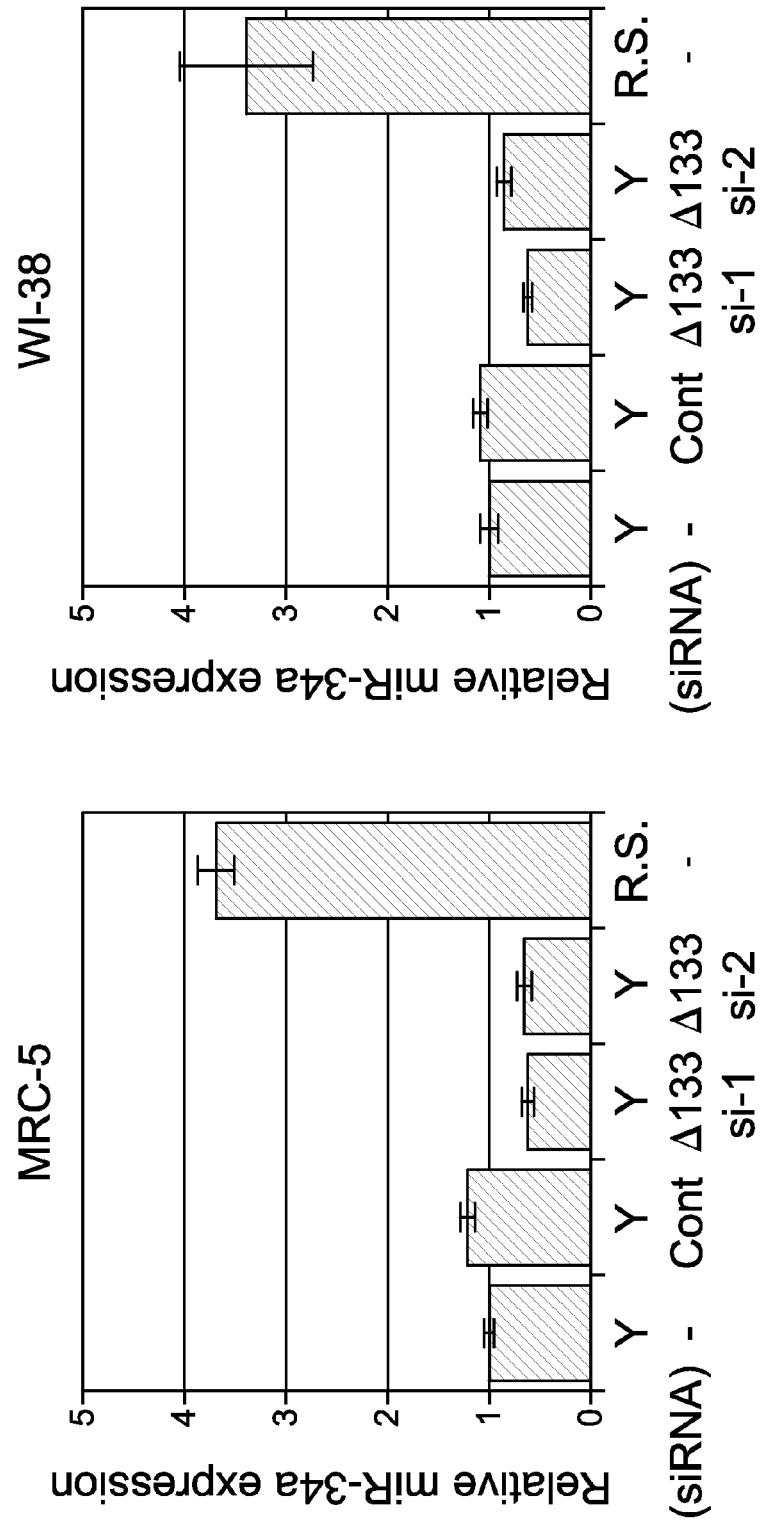
FIG. 24. mir-34a is not upregulated at Δ133p53 knockdown-induced senescence. MRC-5 and WI-38 transfected with control, Δ133si-1 and Δ133si-2 oligonucleotides were examined for miR-34a expression, as in FIG. 14b, together with untransfected early-passage (Y) and replicatively senescent (R.S.) cells. The data (mean±s.d. from triplicate sample) are shown as the relative expression levels to untransfected early-passage cells (Y, –).

The endogenous expression of Δ133p53 was knocked down by RNA interference in early-passage WI-38 (FIG. 15) and MRC-5 (FIG. 22). Two small interfering RNA (siRNA) oligonucleotides (Δ133si-1 and Δ133si-2), which target the sequences that are present in Δ133p53 mRNA as 5' untranslated region, but spliced out of full-length p53 mRNA as intron 4, efficiently downregulated the endogenous Δ133p53 with a minimal effect on full-length p53 and no induction of p53β (FIG. 15a and FIG. 22a). The cells transfected with Δ133si-1 and Δ133si-2, but not those with a control scrambled oligonucleotide, underwent a senescent growth arrest uniformly and rapidly (within 7 days), showing the flattened cell morphology (FIG. 15b, FIG. 22b), the induction of SA-β-gal activity (FIG. 15b, 15c, 22b), and the attenuation of BrdU incorporation (FIG. 15d, 22c). These results indicate that the endogenous expression of Δ133p53 is critical to the replicative potential of normal human fibroblasts, and that the downregulation of Δ133p53 can play a physiological role in the induction of cellular senescence. The Δ133p53 knockdown-induced senescence was accompanied by the upregulation of p21$^{WAF1}$ (FIG. 15a, 22a) and PAI-1 (plasminogen activator inhibitor-1) (FIG. 15e), another p53 target gene responsible for the induction of replicative senescence', consistent with the activation of the full-length p53 function upon a relief from the dominant-negative inhibition by Δ133p53[5]. Immunoblot analyses of PARP [poly(ADP-ribose) polymerase] or caspase-3 did not show a sign of apoptosis in these siRNA-transfected fibroblasts (FIG. 23). Unlike at replicative senescence, miR-34a was not upregulated at Δ133p53 knockdown-induced senescence (FIG. 24), suggesting that some (e.g., p21$^{WAF1}$ and PAI-1), but not all (e.g., miR-34a), p53 target genes respond to an acute inhibition of Δ133p53 and are sufficient for the full induction of cellular senescence.

Figure 16:
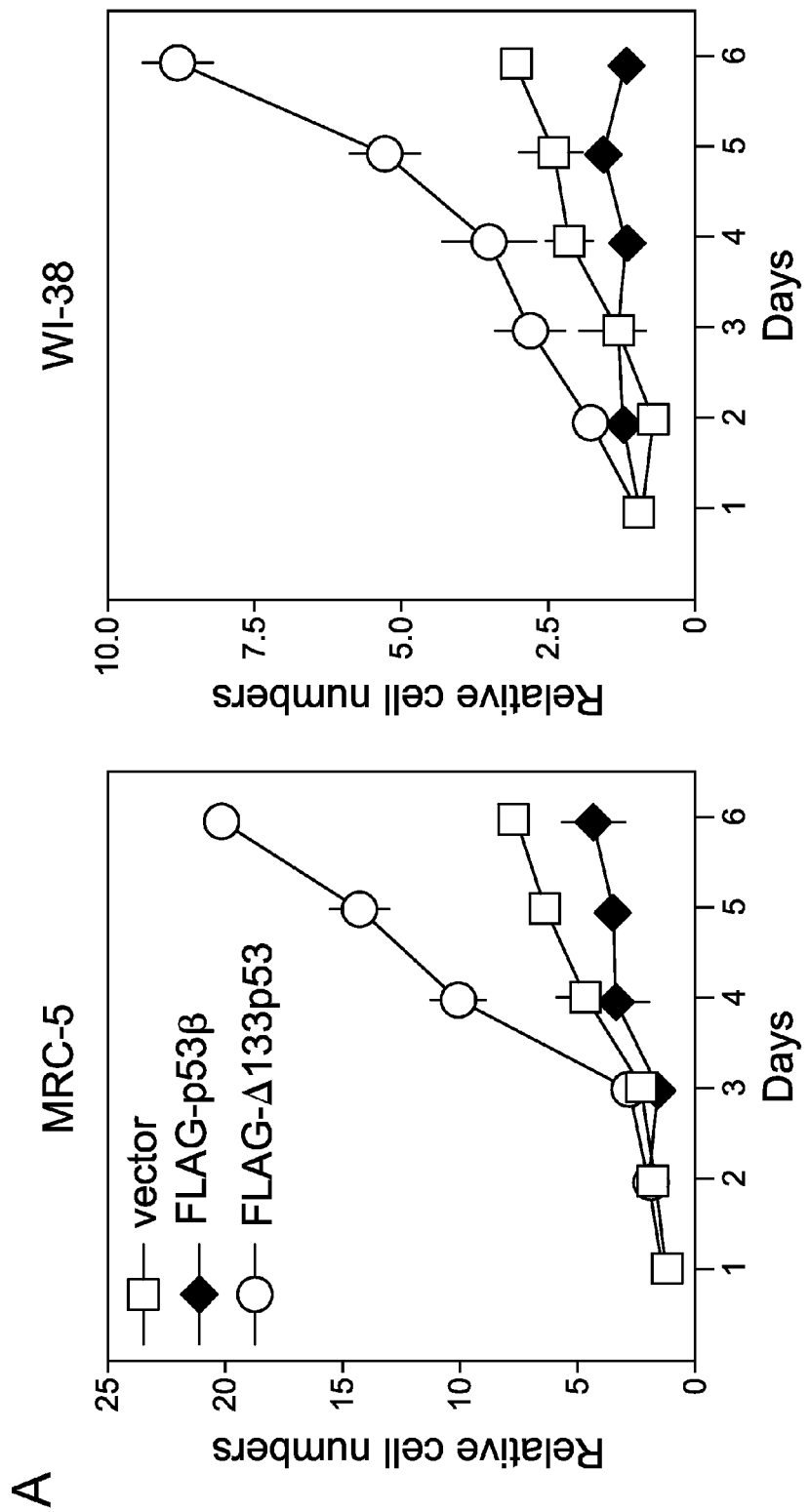
FIG. 16. Overexpression of p53β induces senescence and overexpression of Δ133p53 extends replicative lifespan. Effects of retrovirally overexpressed p53β and Δ133p53 on cell proliferation and senescence. a, Early-passage MRC-5 and WI-38 fibroblasts (both at passage 32) were retrovirally transduced with vector alone (open squares), full-length p53 (open diamonds), FLAG-tagged p53β (closed circles) and FLAG-tagged Δ133p53 (closed triangles), and used in cell proliferation assay at 8 days after retroviral transduction. The cell numbers were counted daily and the data (mean±s.d.) were from three independent experiments. b, Summary of SA-β-gal assay. The same set of cells as in (a) were examined at 8 days after retroviral transduction. The data (mean±s.d.) were from three independent experiments. *, p<0.01. c, Extension of cellular replicative lifespan by Δ133p53. The FLAG-Δ133p53 retroviral vector (open circles) or the control vector (open squares) was transduced to human fibroblasts at late passage (MRC-5 at passage 53 and WI-38 at passage 51). The cumulative PDL were calculated and plotted to days after G418 selection. d, SA-β-gal staining of control and Δ133p53-overexpressing MRC-5 fibroblasts. The pictures at 36 days post-selection are shown. e, Repression of miR-34a expression by Δ133p53. RNA samples from MRC-5 (at passage 53) before transduction (day 0), MRC-5 with control vector and MRC-5 overexpressing Δ133p53 (at days 20, 36 and 96 post-selection) were analyzed as in FIG. 14b. The value before transduction was defined as 1.0 and the expression levels in the other samples were expressed as the relative values (mean±s.d. from triplicate sample). f, Telomere length and telomeric 3' overhang in Δ133p53-overexpressing cells. Genomic DNA samples from MRC-5 with FLAG-Δ133p53 or control vector were used in the in-gel hybridization with $^{32}$P-[CCCTAA]$_4$ (SEQ ID NO:5)probe under denatured (for telomere length) and native (for telomeric 3' overhang) conditions. Lane 1, MRC-5 before transduction; lanes 2-3, vector control (days 4 and 35 post-selection); lanes 4-6, FLAG-Δ133p53 (days 4, 35 and 96 post-selection). The telomere lengths were measured as peak TRF (terminal restriction fragment) lengths. The amounts of telomeric 3' overhang were normalized with loaded DNA amounts (EtBr) and shown as percent signals to the cells before transduction.
Figure 16:
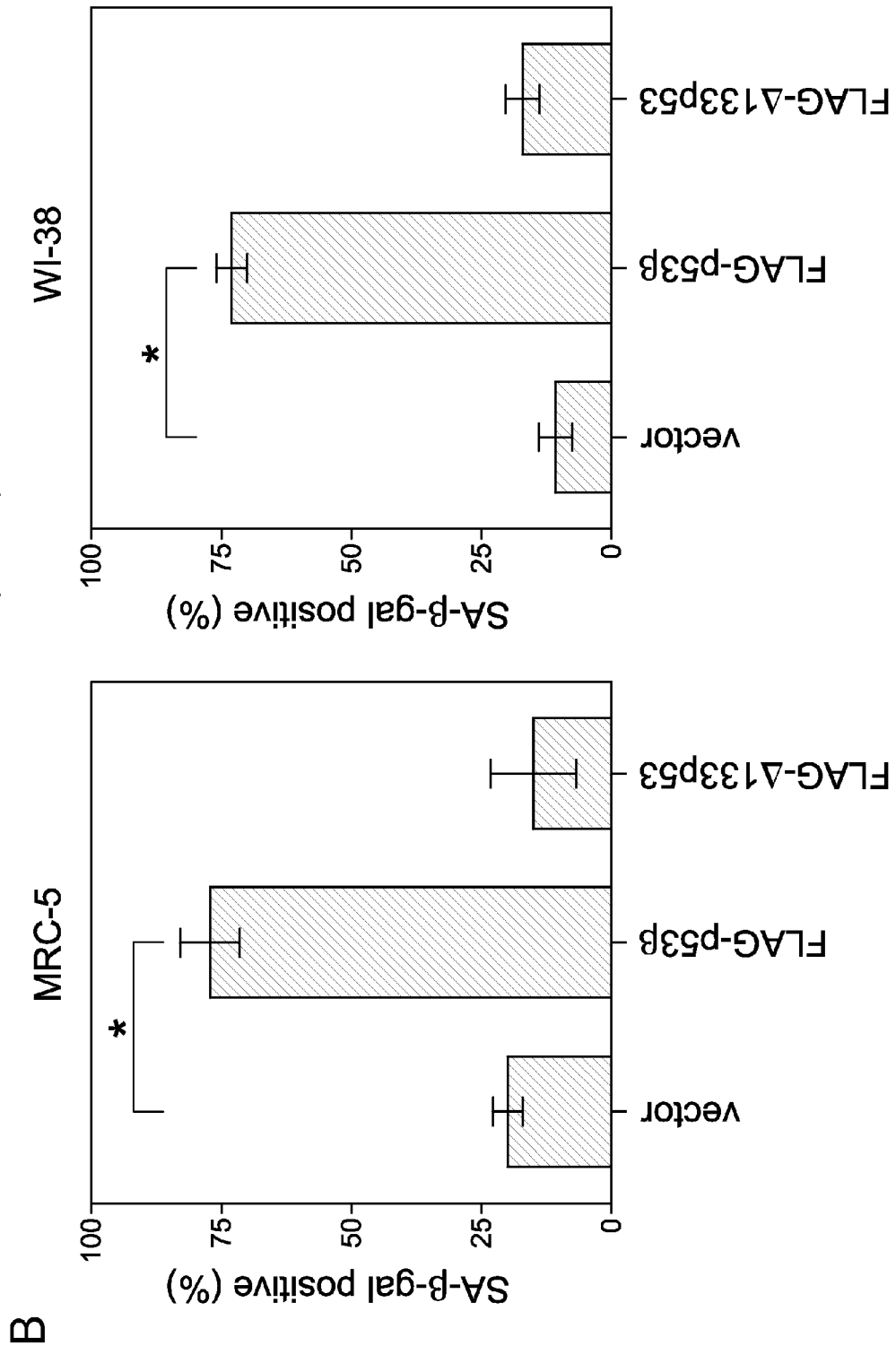
Figure 16:
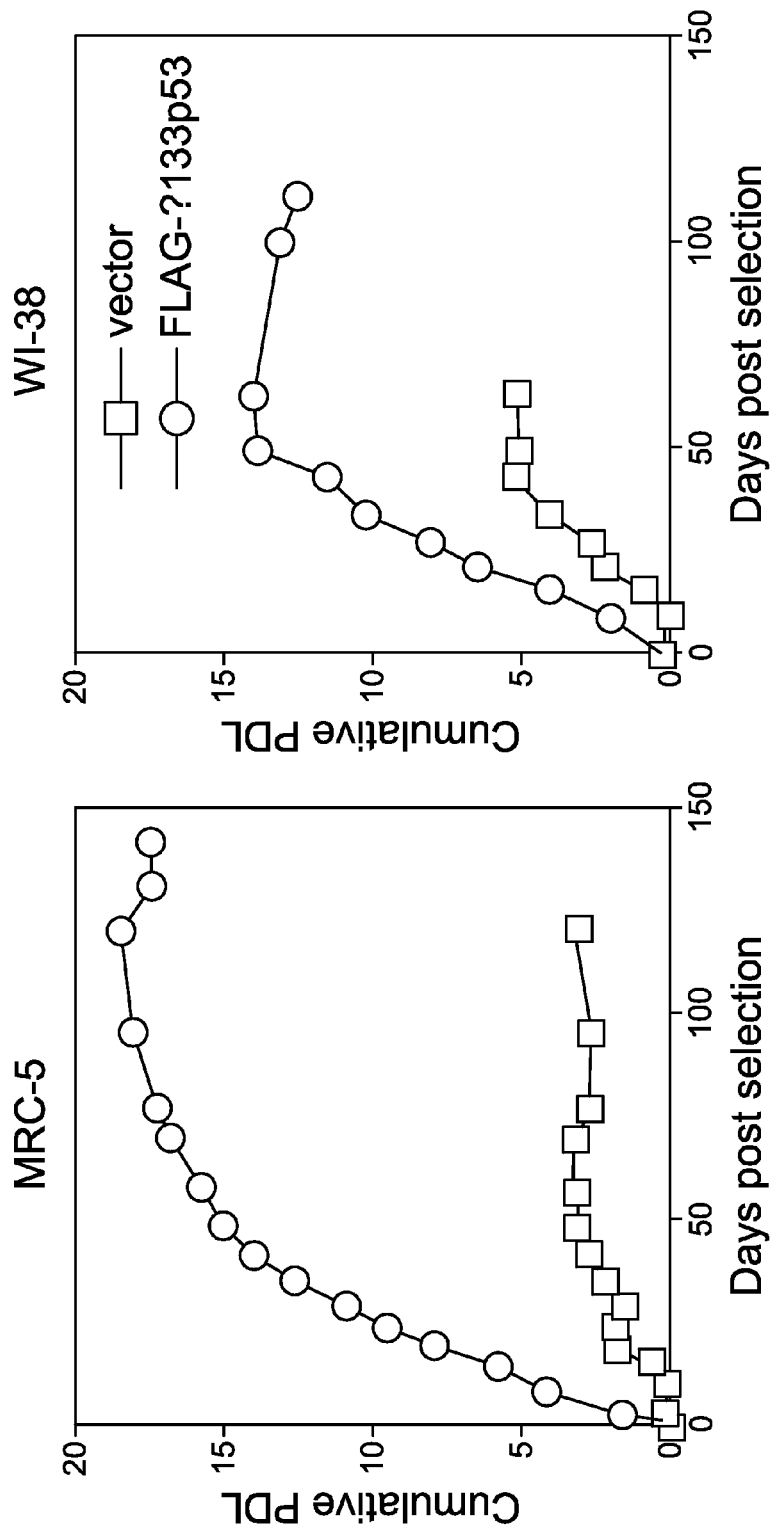
Figure 16:
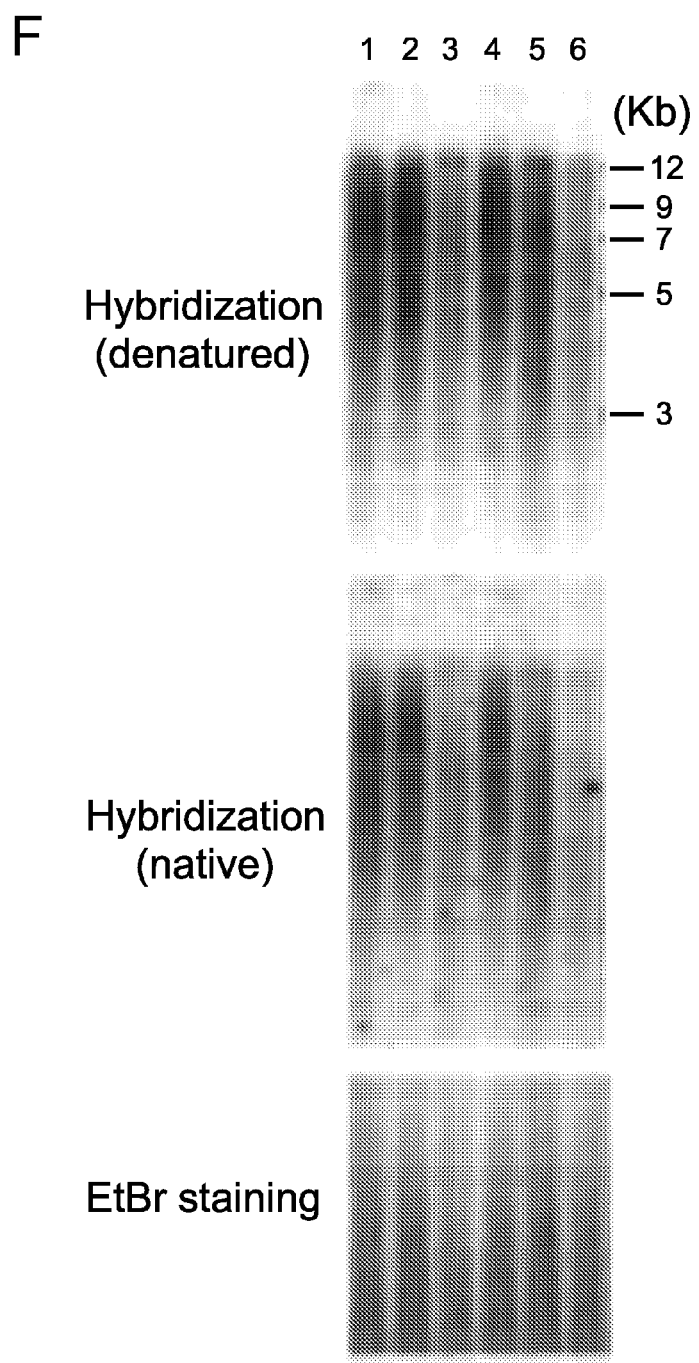
Figure 16:
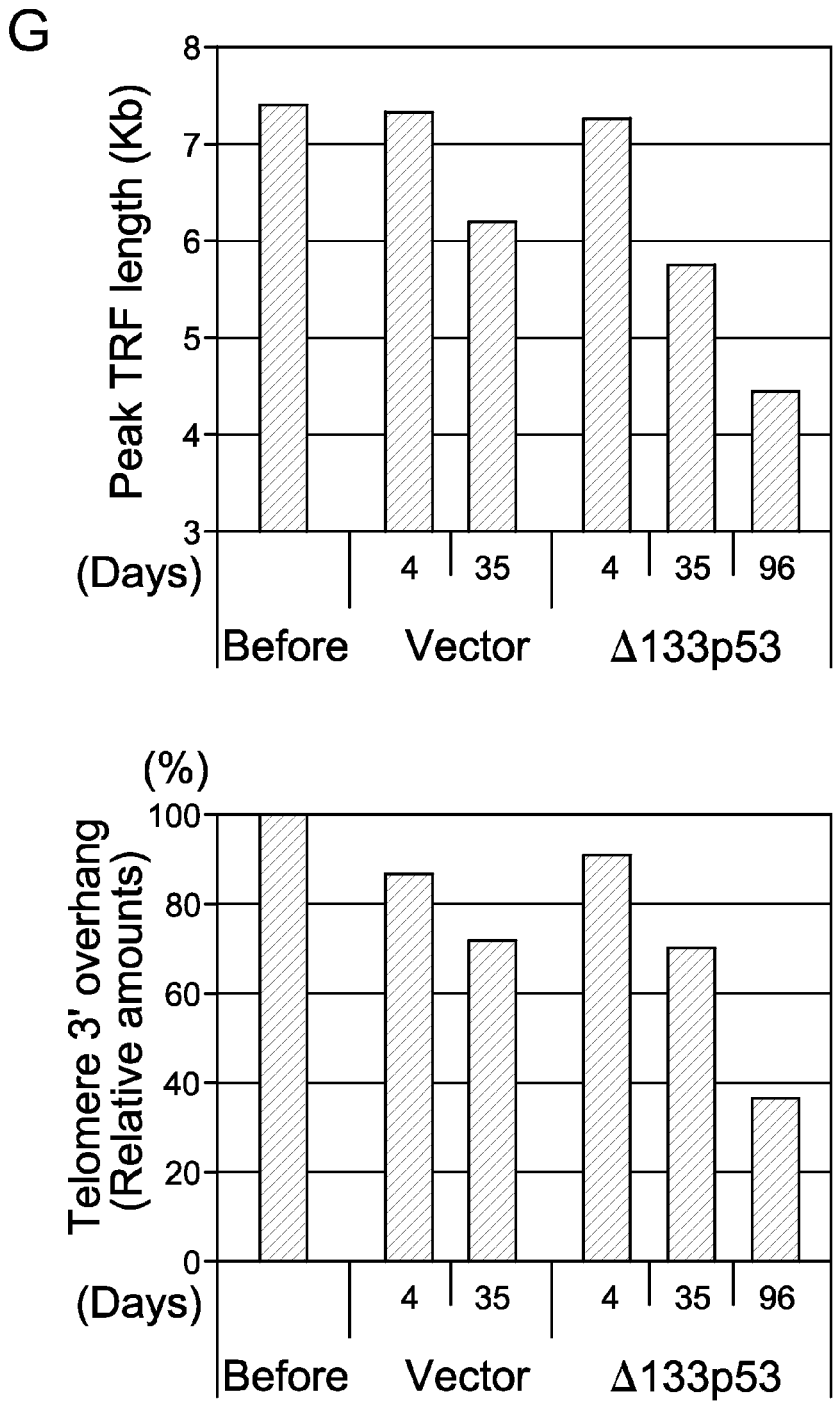
Figure 25:
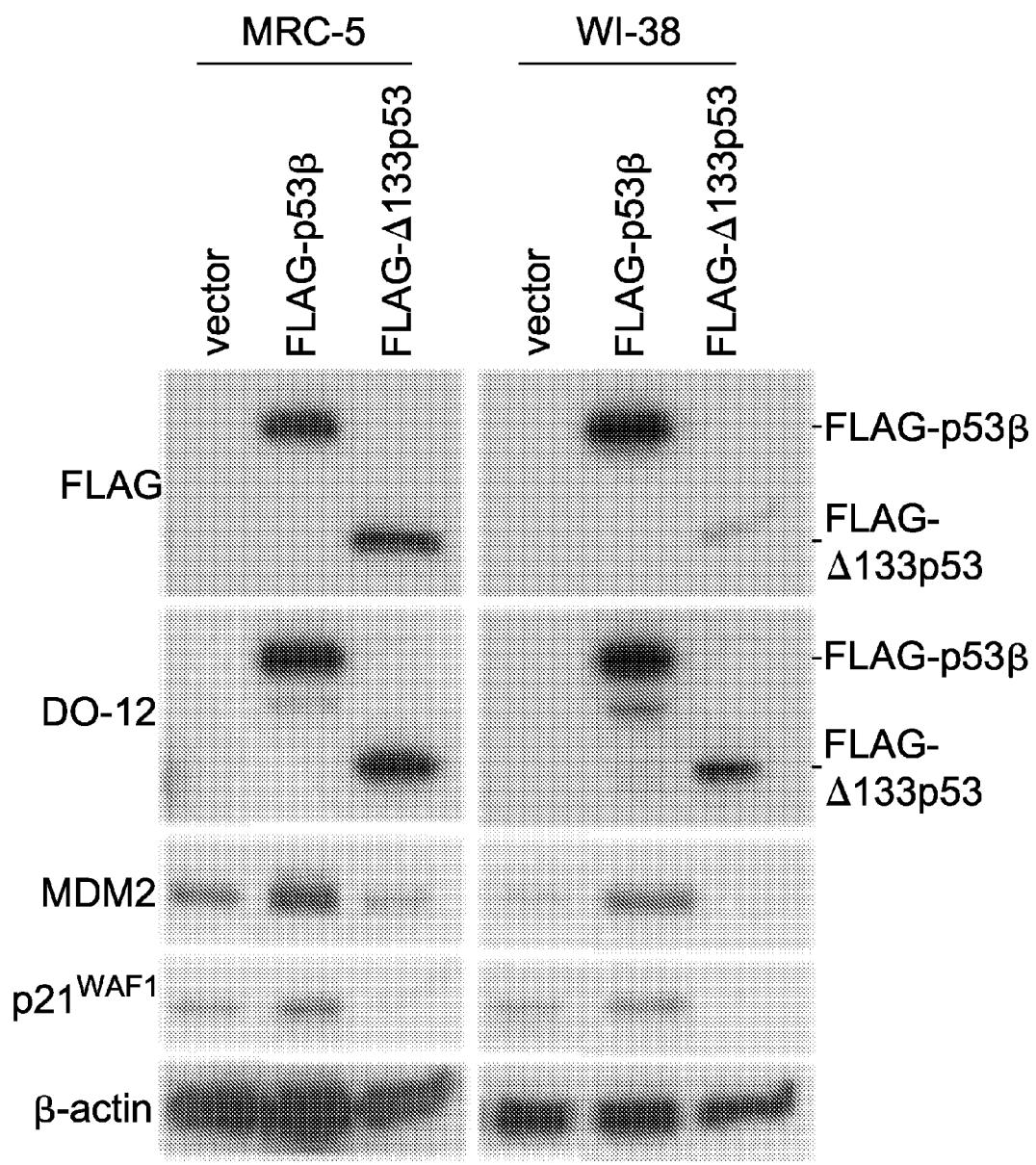
FIG. 25. Retroviral overexpression of p53 isoforms in human fibroblasts. The retroviral vectors driving full-length p53, FLAG-tagged p53β and FLAG-tagged Δ133p53 were transduced to human fibroblasts at early passage (at passage number 30 for both strains) and the immunoblot analyses of the overexpressed full-length p53 and p53 isoforms, MDM2 and p21$^{WAF1}$ were performed. Protein samples were prepared from the cells at 8 days after retroviral transduction. The anti-FLAG antibody detected FLAG-tagged p53β and FLAG-tagged Δ133p53. The DO-12 antibody detected full-length p53, FLAG-tagged p53β and FLAG-tagged Δ133p53. β-actin was a loading control.

To further examine the effects of the p53 isoforms on cell proliferation and senescence, the FLAG-tagged p53β and Δ133p53, as well as full-length p53, were retrovirally expressed in the early-passage human fibroblast strains (FIG. 16, 25). Similar to full-length p53, p53β inhibited cell proliferation (FIG. 16a) and induced cellular senescence, characterized by the senescence-associated β-galactosidase (SA-β-gal) activity (FIG. 16b). The senescence induction by p53β overexpression was associated with the upregulation of the full-length p53 transcriptional targets, p21$^{WAF1}$ and MDM2[21] (FIG. 25), confirming that p53β enhances the intrinsic transcriptional activity of p53 as previously described[5]. p53β also inhibited cell proliferation and induced cellular senescence in a telomerase-immortalized fibroblast cell line (FIG. 26). However, the overexpression of p53β had no effect on cell proliferation, cellular senescence or the expression of p21$^{WAF1}$ and MDM2 in p53-null MDAH041 fibroblasts (homozygous for a frameshift mutation at codon 184)[22] (data not shown), indicating that p53β co-operates with full-length p53 to enhance its senescence-inducing activity. In contrast to full-length p53 and p53β, the overexpression of Δ133p53 in MRC-5 and WI-38 fibroblasts accelerated cell proliferation (FIG. 16a) without inducing cellular senescence (FIG. 16b), and repressed the expression of p21$^{WAF1}$ and MDM2 (FIG. 25).

Figure 27:
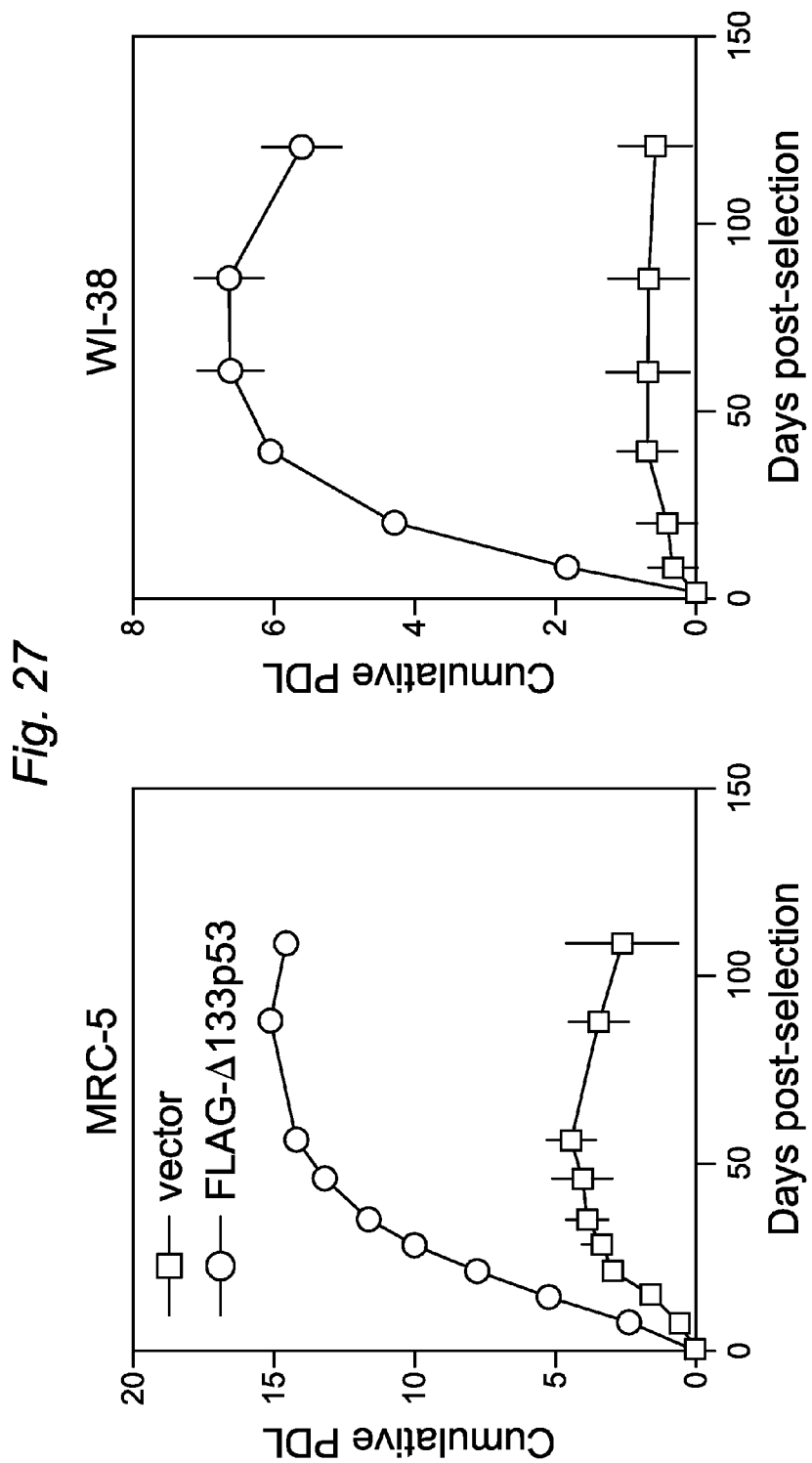
FIG. 27. Δ133p53 overexpression extends the replicative lifespan in human fibroblasts. Late-passage MRC-5 (at passage 55) and WI-38 (at passage 53) were transduced with the FLAG-Δ133p53 retroviral vector or the control vector and examined for the cumulative PDL, as in FIG. 16c.

The biological effects of Δ133p53 were more evident when overexpressed in the late-passage human fibroblasts, just before the senescent stage. In MRC-5 and WI-38, whereas the vector control cells underwent senescent growth arrest at only one to five PDLs after retroviral transduction, the Δ133p53-overexpressing cells reproducibly bypassed this normal senescence point and continued to proliferate for six to 15 more PDLs (FIG. 16c, 16d, 27). As shown in FIG. 16e, the expression of miR-34a in Δ133p53-overexpressing MRC-5 remained restricted to low levels throughout the replicative lifespan. The Δ133p53-induced extension of the replicative lifespan was not due to telomere stabilization; in the Δ133p53-overexpressing cells, both the overall length of telomeres and the amount of telomeric 3' overhangs continued to be reduced beyond those in the senescent vector control cells (FIG. 16f; compare Δ133p53 at day 96 and vector at day 35). Similar to other human cell cultures showing the lifespan extension with a progressive erosion of telomeres, including SV40 large T- and HPV E6/E7-expressing fibroblasts[23], the extension of replicative lifespan by Δ133p53 is thus attributed to the repression of p21$^{WAF1}$ (FIG. 25), which results in the failure to arrest the cell cycle[16], and the repression of miR-34a (FIG. 16e), which can allow a group of genes for cell cycle progression to remain expressed[18].

Figure 28:
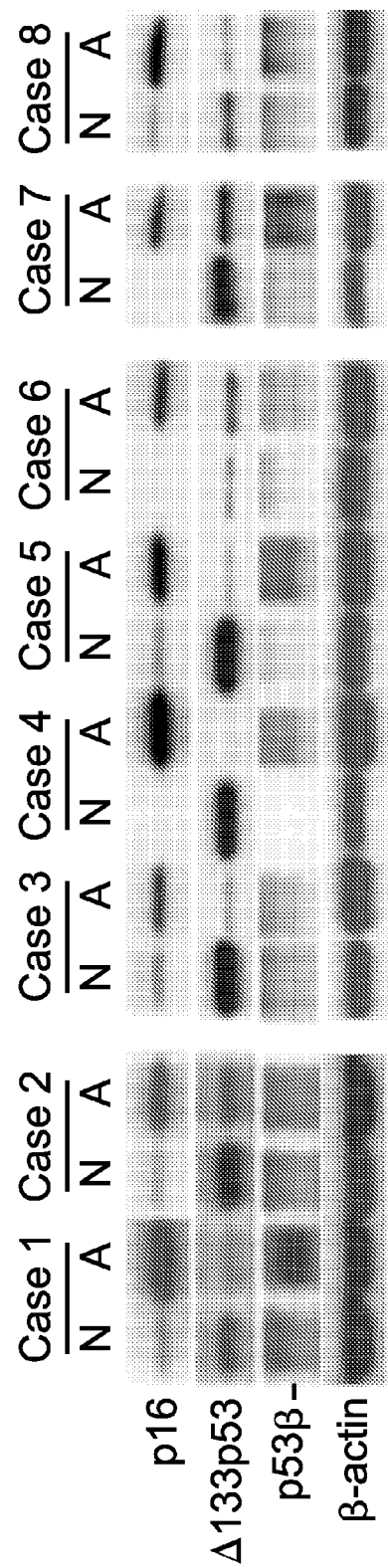
FIG. 28. Immunoblot analyses of p16$^{INK4A}$, Δ133p53 and p53β in human colon adenomas. Eight cases of matched non-adenoma (N) and adenoma (A) tissues were examined for p16$^{INK4A}$, Δ133p53 and p53β. β-actin was the control for quantitation. The data shown in FIGS. 34e and 4f were from the quantitative analysis of these results.
Figure 29:
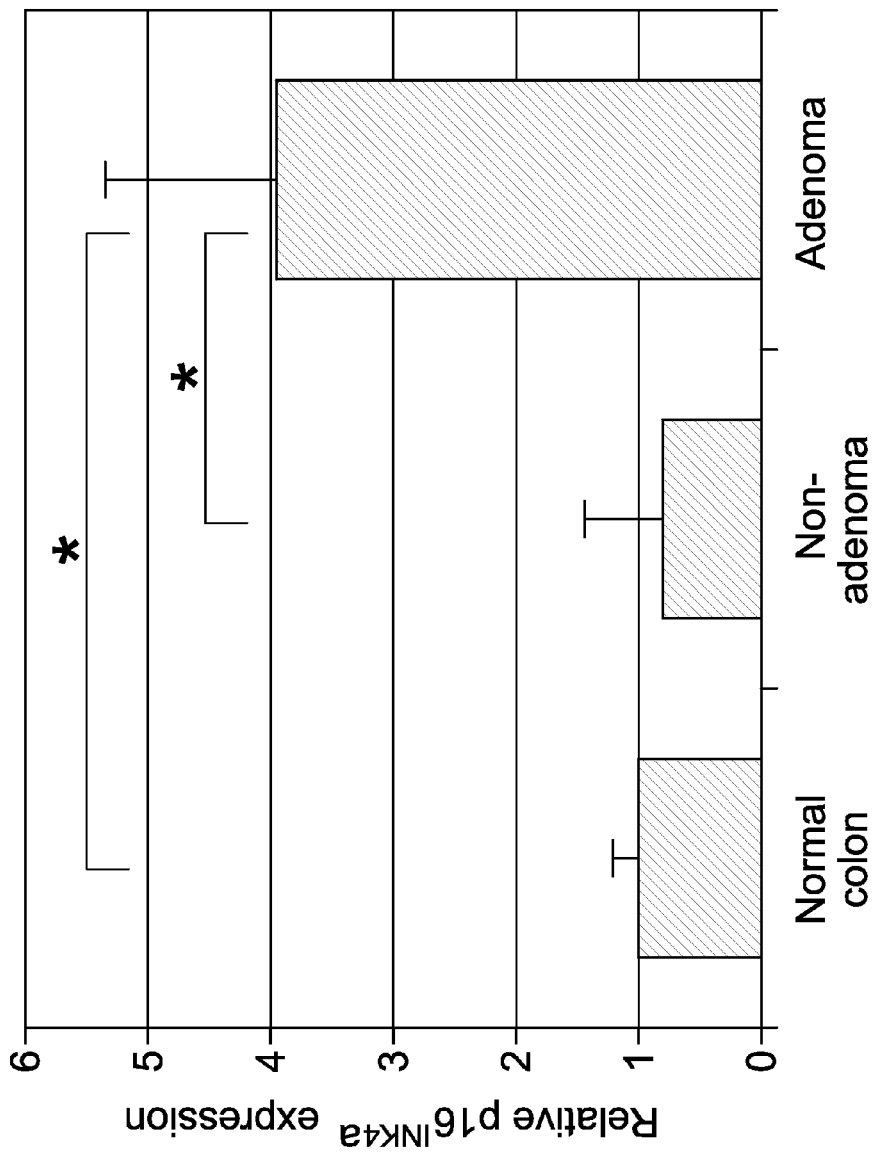
FIG. 29. Increased p16$^{INK4a}$ expression in colon adenomas. The expression levels of p16$^{INK4A}$, an in vivo senescence marker, were examined in 9 normal colon tissues (Table 1) and 8 pairs of non-adenoma and adenoma tissues (Table 2) and quantitatively analyzed. The data (mean±s.d.) are shown as the relative values to normal colon samples. *, p<0.0001.
Figure 30:
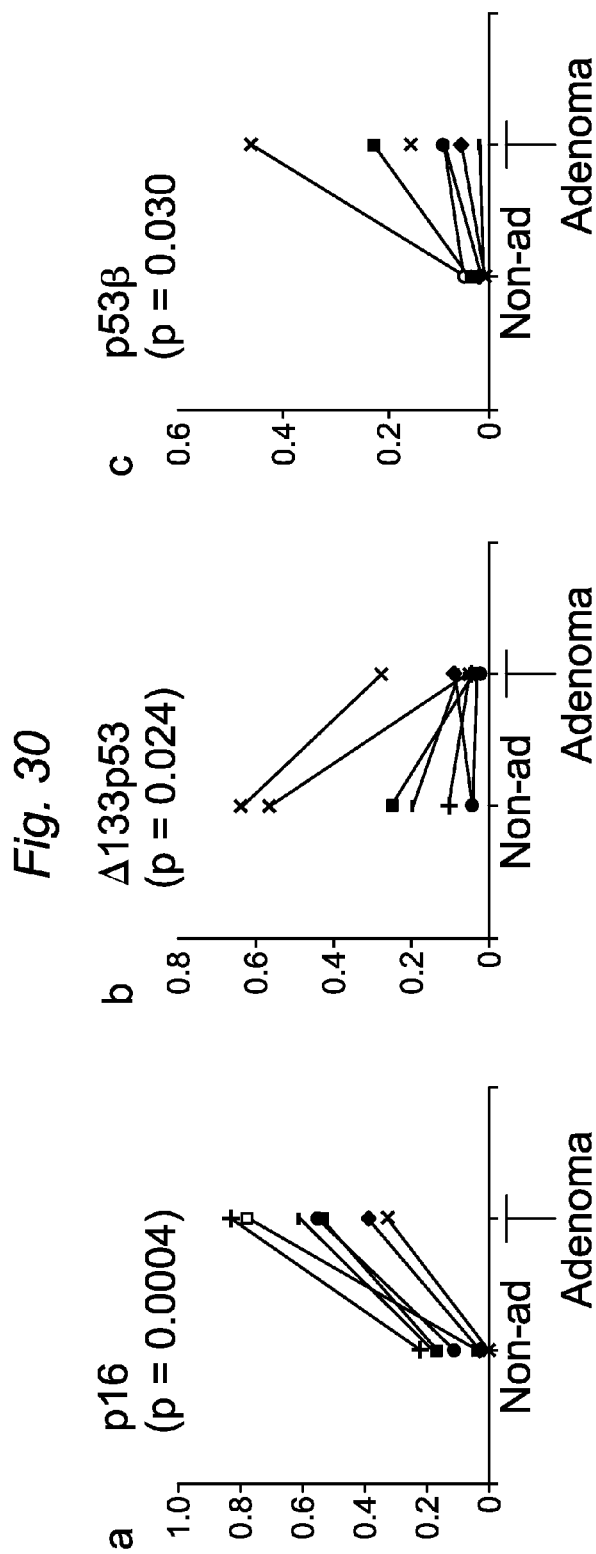
FIG. 30. Paired t-test analyses of p16$^{INK4a}$, Δ133p53 and p53β expression in matched colon adenoma and non-adenoma tissues. The same data as in FIG. 17b and FIG. 29 from 8 pairs of non-adenoma (Non-ad) and adenoma tissues were analyzed by paired t-test. The vertical axes are the expression levels normalized with β-actin. The p-values for p16$^{INK4A}$, Δ133p53 and p53β are 0.0004, 0.024 and 0.03, respectively, and the corresponding Bonferroni corrected p-values are 0.001, 0.07 and 0.09, respectively. Case 1, aqua; case 2, blue; case 3, cyan; case 4, yellow; case 5, lavender; case 6, navy; case 7, purple; and case 8, brown.
Figure 34:
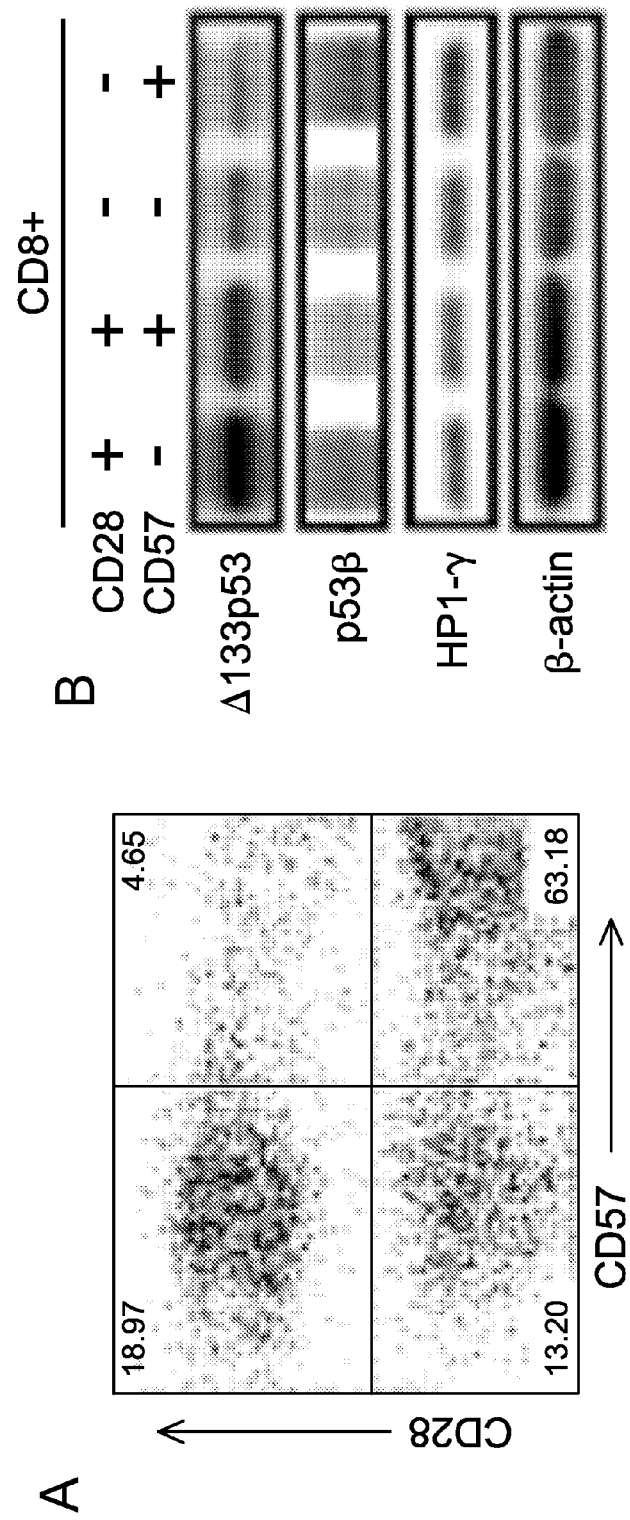
FIG. 34. p53 isoform switching in vivo. a-c, Increased p53β and decreased Δ133p53 expression during CD8$^+$ T lymphocyte senescence in vivo. a, CD8$^+$ T lymphocytes were purified from blood samples freshly isolated from healthy donors of age ≥50 years old, and sorted by flow cytometry using anti-CD28 and anti-CD57 antibodies. The result of 50-year-old male is shown. b, Representative immunoblot of p53β and Δ133p53. The results of 65-year-old male are shown. HP1-γ was examined as a senescence marker. β-actin was a loading control for quantitation. c, The expression levels of p53β and Δ133p53 in each of the quadrants were quantitated in immunoblot analyses and shown as the relative values to the CD28$^-$CD57$^+$ quadrant (p53(3)) or CD28$^+$CD57$^-$ quadrant (Δ133p53). The data (mean±s.d.) were from three donors (60-year-old female, 65-year-old male and 50-year-old male). The p-values from ANOVA trend analysis are shown. d-f, Elevated expression of p53β and reduced expression of Δ133p53 in colon adenomas with senescent phenotypes. d, SA-β-gal staining of non-adenoma and adenoma tissues. The results of case 7 are shown. The rectangular areas are enlarged in the right panels. Bars, 500 e, The expression levels of p53β and Δ133p53, as well as a senescence marker p16$^{INK4A}$, were examined in 9 normal colon tissues obtained from immediate autopsy (Table 1) and 8 matched pairs of non-adenoma and adenoma tissues surgically resected (Table 2) and quantitatively analyzed. The data (mean±s.d.) are shown in a logarithmic scale as the relative values to normal colon samples. *, p<0.05. , p<0.0005. *, p<0.00005. f, The same data as in (e) from 8 matched pairs of non-adenoma (Non-ad) and adenoma tissues were analyzed by paired t-test. The vertical axes are the expression levels normalized with β-actin. The p-values for p16$^{INK4A}$, Δ133p53 and p53β are 0.0004, 0.024 and 0.03, respectively, and the corresponding Bonferroni corrected p-values are 0.001, 0.07 and 0.09, respectively. Case 1, aqua; case 2, blue; case 3, cyan; case 4, yellow; case 5, lavender; case 6, navy; case 7, purple; and case 8, brown.
Figure 34:
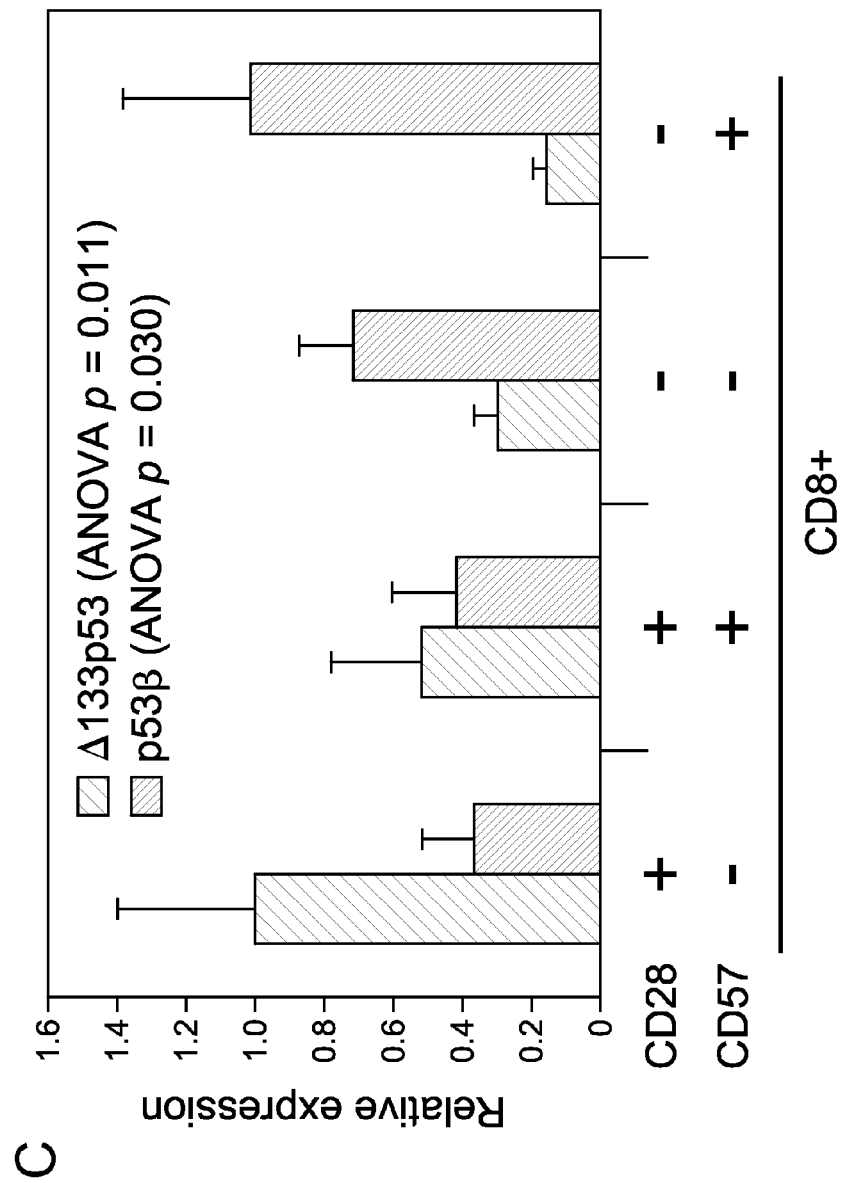
Figure 34:
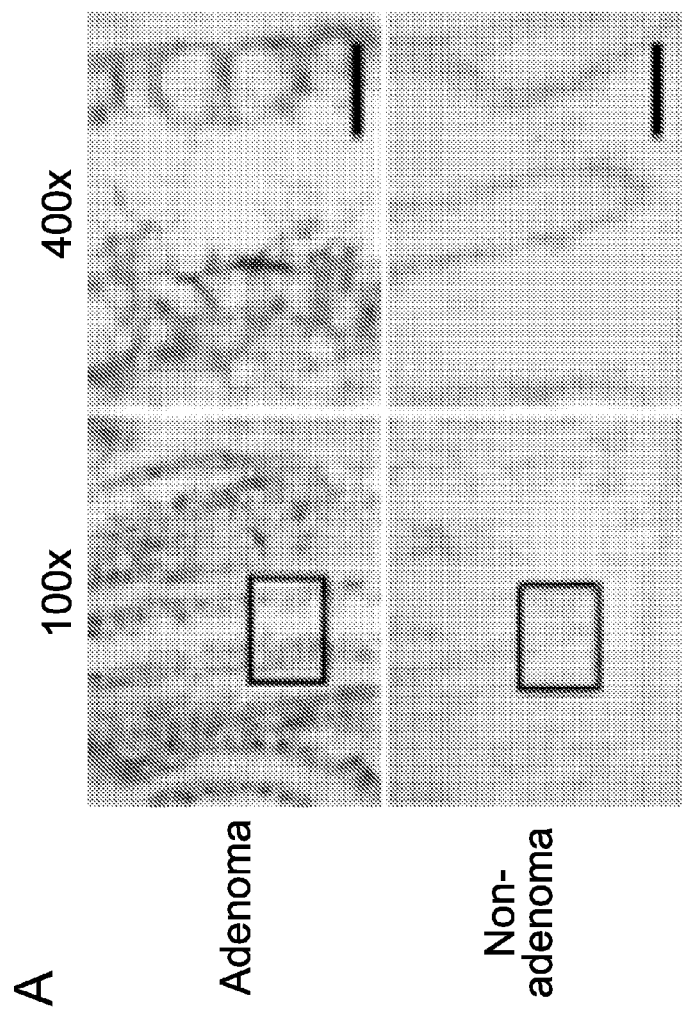
Figure 34:
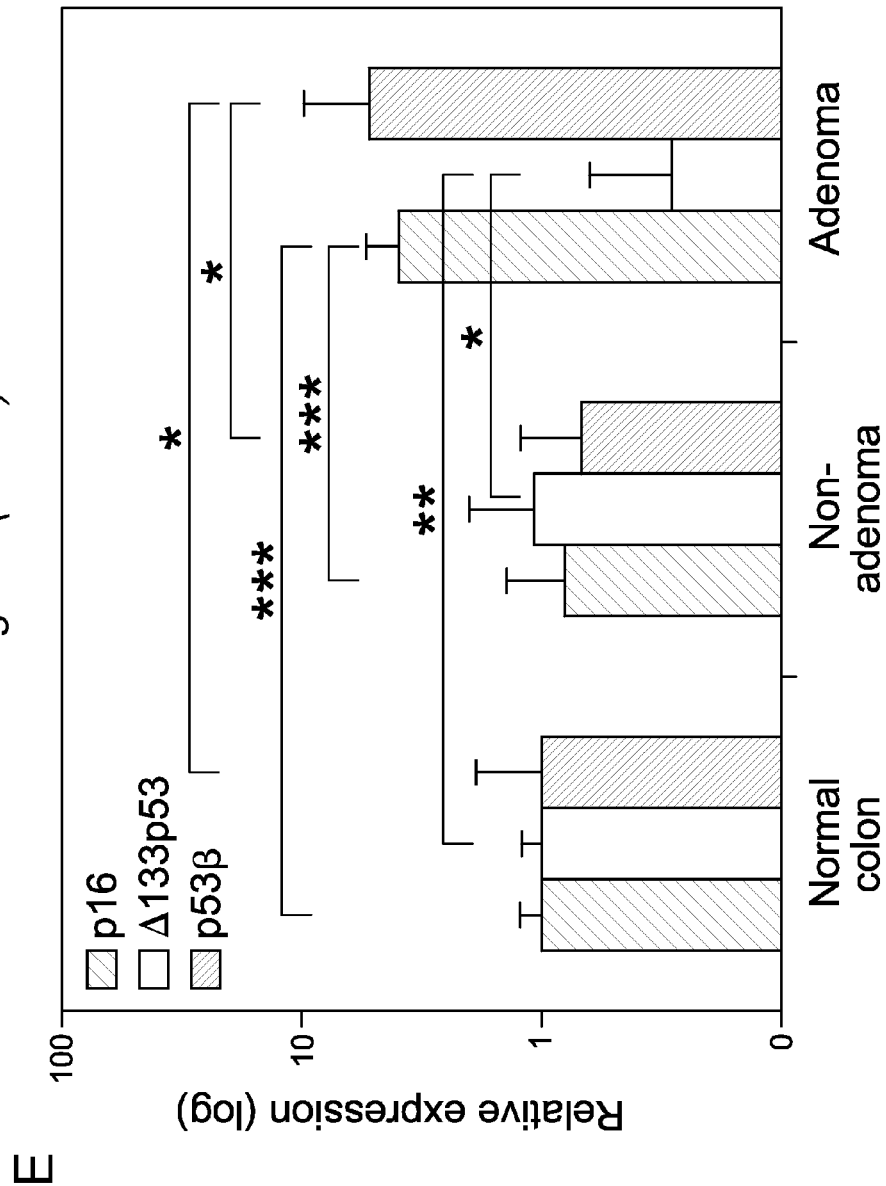
Figure 34:
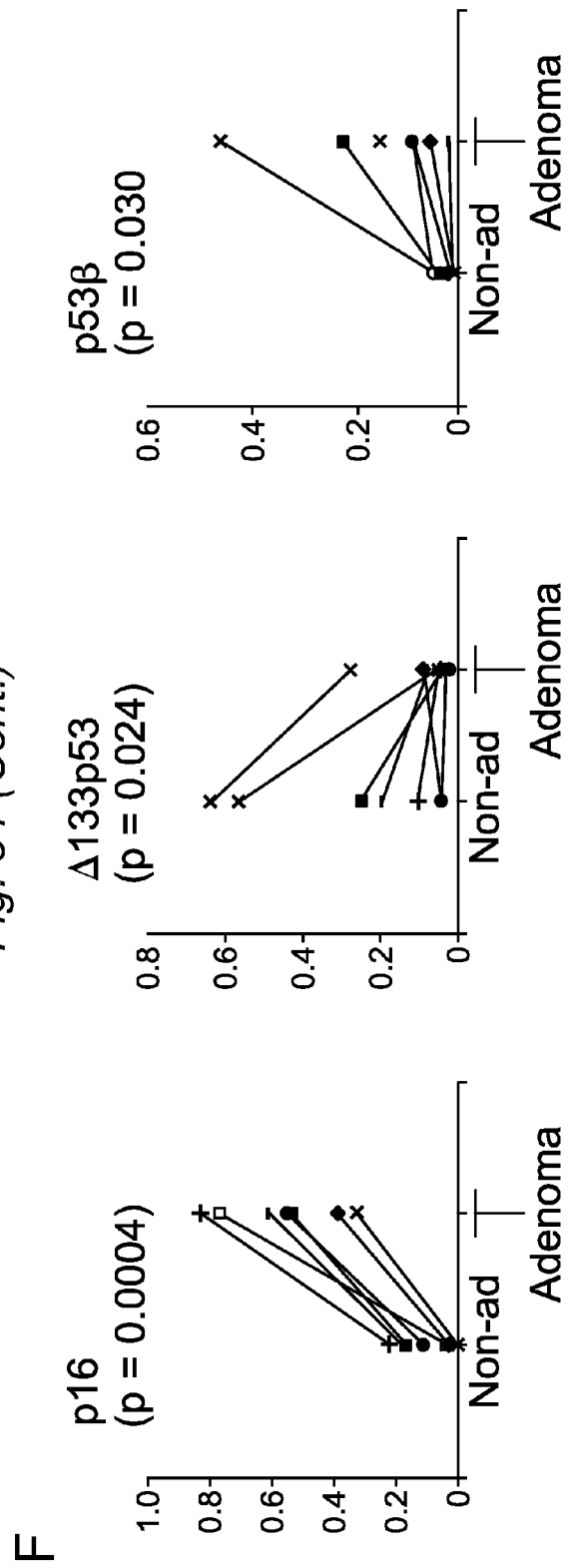
Figure 36:
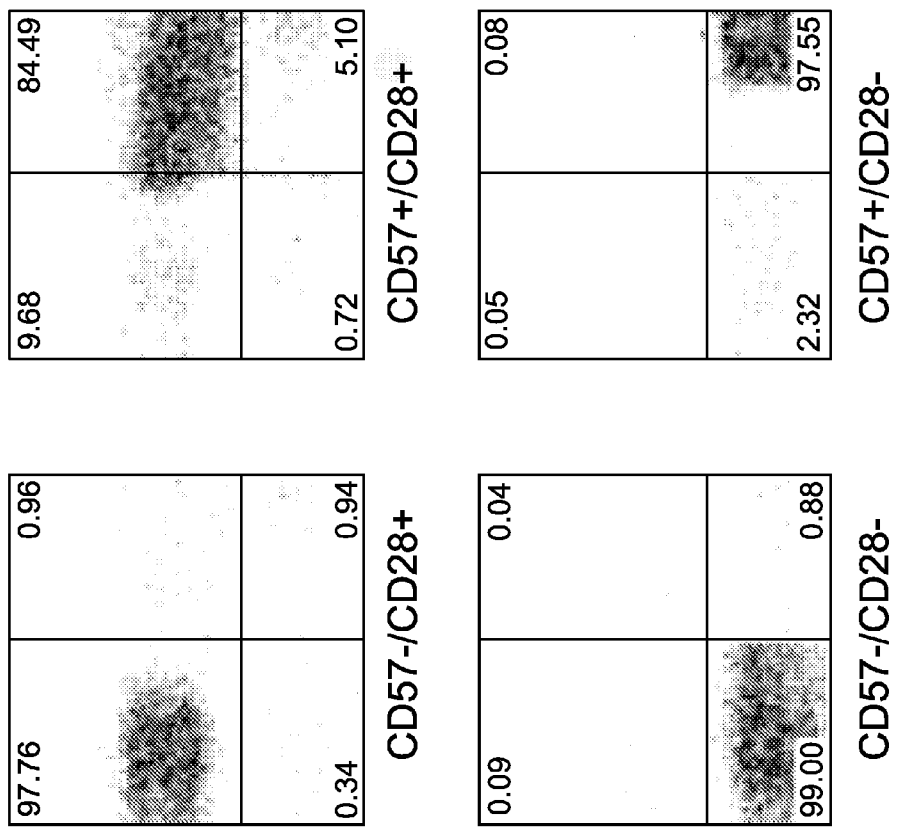
FIG. 36. FACS (Fluorescence-activated cell sorting) of human $CD8^+$ T lymphocytes. a, Summary of the sorted fractions from three donors. b, The purity of sorted fractions was checked by FACS reanalysis. The result of 50-year-old male is shown. c, Immunoblot analysis of the sorted fractions for HP1-γ as a senescence marker (Collado et al. *Nature* 436, 642 (2005); Narita et al. *Cell* 113, 703-716 (2003); Zhang et al. *J. Cell Science* 120, 1572-1583 (2007)). The expression levels of HP1-γ were quantitated and expressed as the relative values to $CD28^+CD57^-$ fraction. The data (mean±s.d.) were from three donors. The difference between $CD28^+CD57^-$ and $CD28^-CD57^+$ fractions is statistically significant ($p<0.05$).
Figure 36:
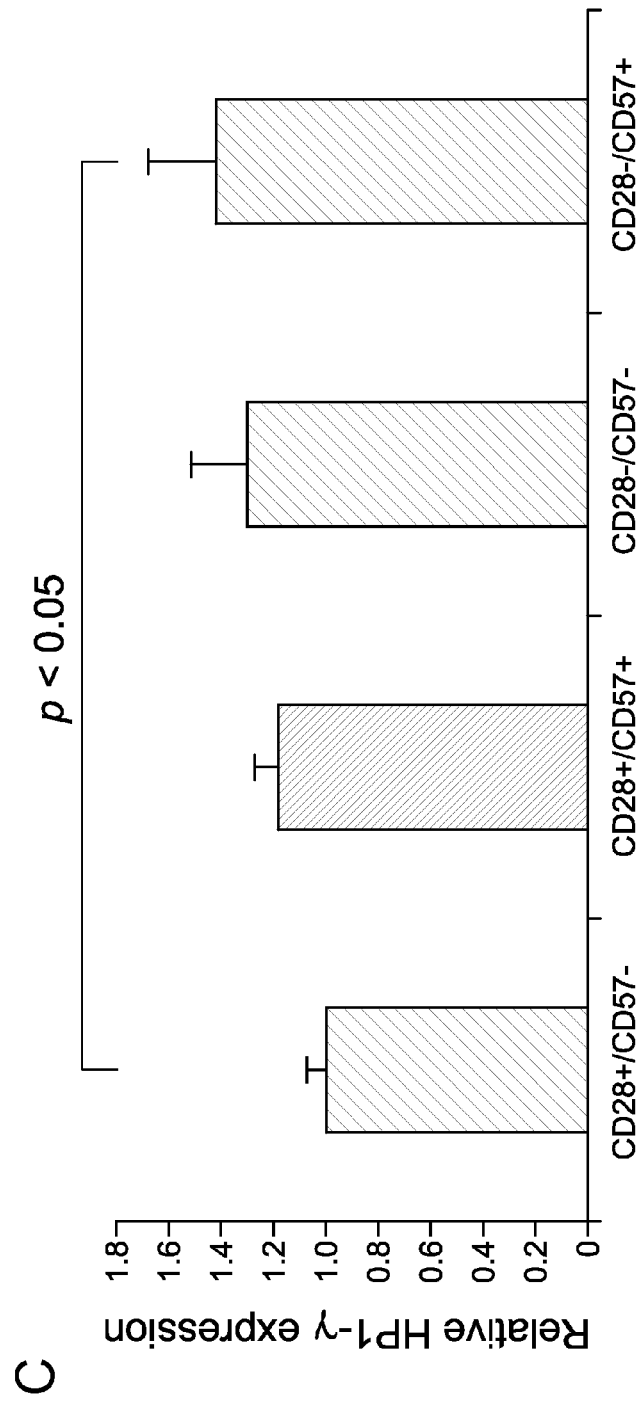
Figure 37:
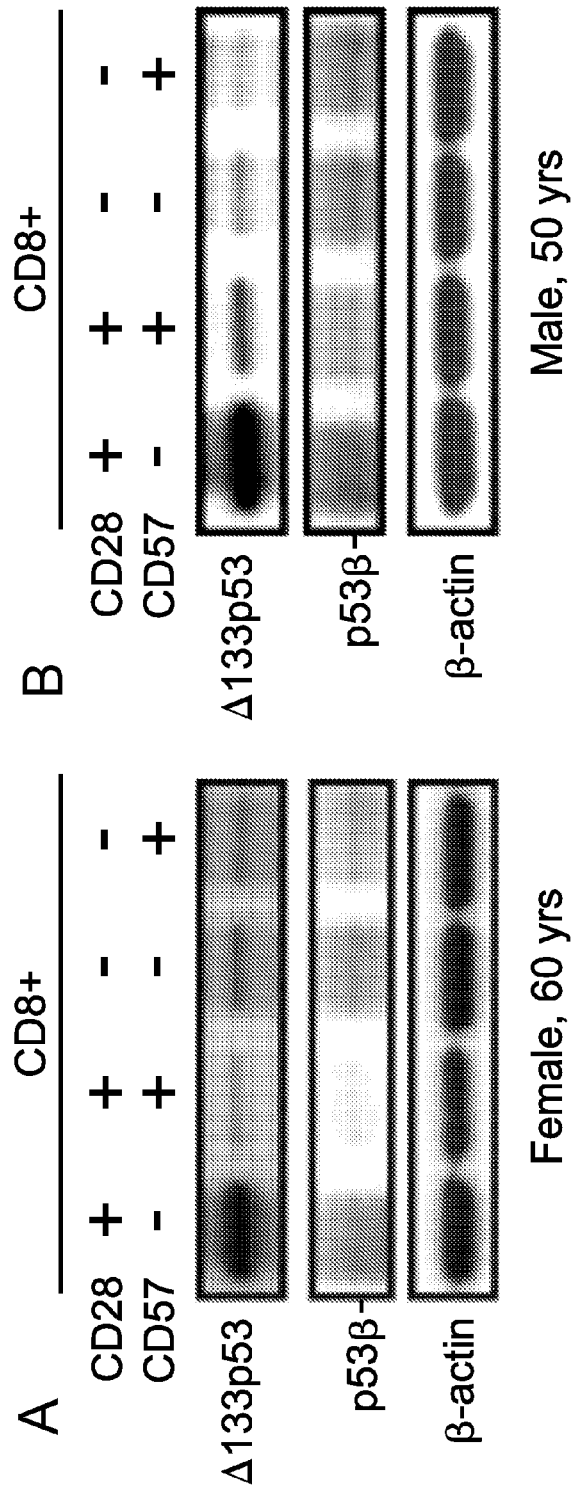
FIG. 37. Δ133p53 and p53β expression in human $CD8^+$ T lymphocytes. Immunoblot analysis as shown in FIG. 14b. a, 60-year-old female. b, 50-year-old male.

To investigate whether the p53 isoforms are also involved in cellular senescence in vivo, CD8$^+$ T lymphocytes were freshly isolated from healthy donors of age ≥50 yrs and fractionated by flow cytometry using the CD28 and CD57 antibodies (FIGS. 34a, 36a and 36b), where CD28$^-$ and CD57$^+$ were the surface markers specific to replicative senescence of CD8$^+$ T lymphocytes[8, 9]. The senescent state of these CD8$^+$ T lymphocytes was confirmed by increased levels of a senescence marker HP1-γ[10, 11] (FIG. 34b, FIG. 36c). The results from three independent donors showed that Δ133p53 and p53β were down- and up-regulated, respectively, in the order from CD28$^+$CD57$^-$ (non-senescent), CD28$^+$CD57$^+$, CD28$^-$CD57$^-$ to CD28$^-$CD57$^+$ (most senescent) fractions (FIG. 35b, 35c, 37), in vivo reproducing the p53 isoform switching as observed in human fibroblasts in cell culture in vitro. We also examined human colon adenomas, which are premalignant tumours associated with telomere shortening-induced replicative senescence[24, 25] and oncogene-induced, interleukin-regulated premature senescence[10, 12, 13]. Consistently, we observed positive SA-β-gal staining in adenoma tissues (FIG. 34d). When normal colon tissues obtained from immediate autopsy[26] (n=9) (Table 1) and 8 pairs of surgically resected, matched non-adenoma and adenoma tissues (Table 2) were compared (FIG. 34e, FIG. 28), the expression of p16$^{INK4A}$, an in vivo senescence marker[27], was significantly more abundant in colon adenomas than in non-adenomas or normal colon tissues, as reported previously[12, 28]. As expected from this increase in senescence, colon adenoma tissues expressed elevated levels of p53β and reduced levels of Δ133p53 compared with non-adenoma and normal colon tissues. The increased expression of pb16$^{INK4A}$ and p53β and the decreased expression of Δ133p53 in adenoma tissues were also observed in the paired analysis of the 8 cases of matched non-adenoma and adenoma tissues (FIG. 34f). These results suggest that the p53 isoform switching occurs not only in cultured cells in vitro but also in humans in vivo, during both physiologically and pathologically induced senescence (T lymphocytes in the elderly and colon adenomas, respectively), and in cells of different origins (mesenchymal, hematopoietic and epithelial origins).

Figure 17:
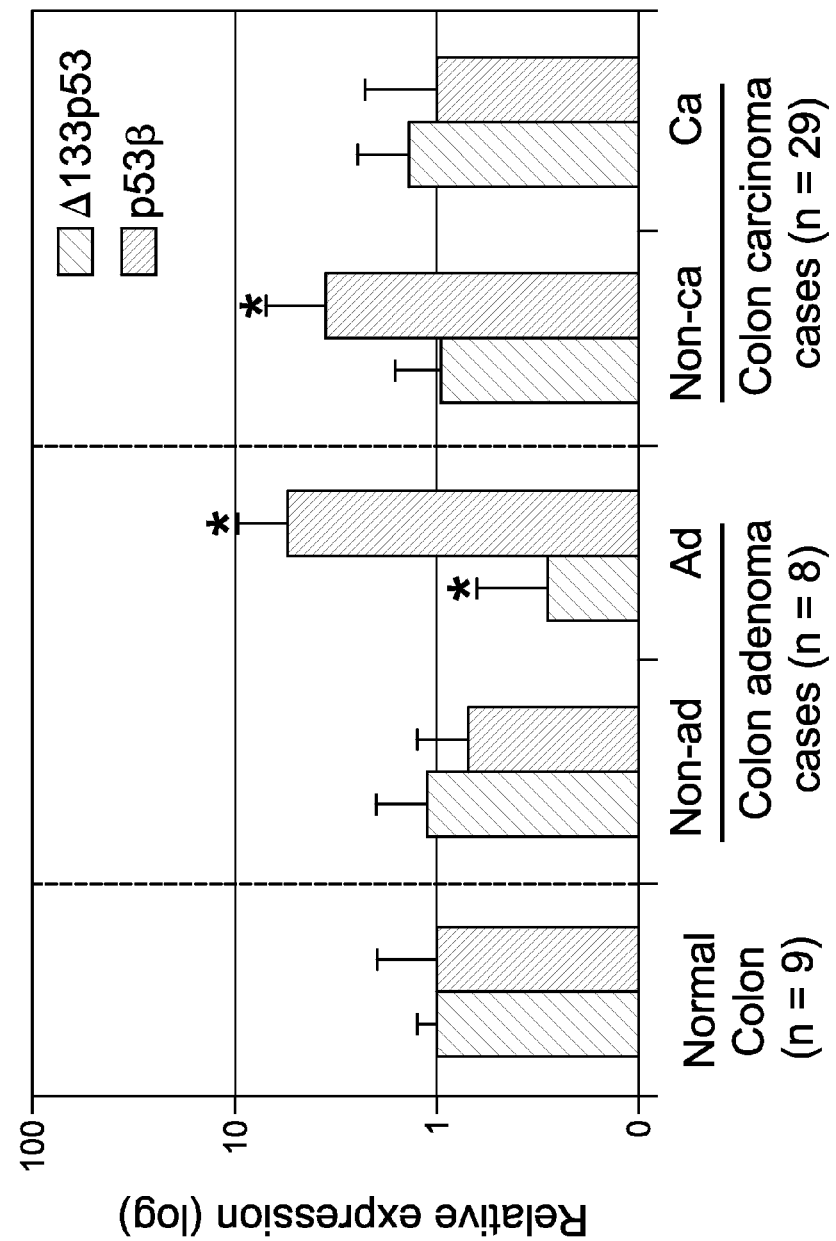
FIG. 17. p53 isoform expression profiles in colon carcinogenesis in vivo. Elevated expression of p53β and reduced expression of Δ133p53 in colon adenomas with senescent phenotypes, but not in colon carcinomas. (a) SA-β-gal staining of non-adenoma and adenoma tissues. The results of case 7 are shown. The rectangular areas are enlarged in the right panels. Bars, 500 μm. (b) The expression levels of p53β and Δ133p53 were quantitatively examined in 9 normal colon tissues obtained from immediate autopsy[21] (Table 1), 8 matched pairs of non-adenoma and adenoma tissues (Table 2) and 29 matched pairs of non-carcinoma and carcinoma tissues (Table 3). The data (mean and s.d.) are shown in a logarithmic scale as the relative values to normal colon samples. *, p<0.05 compared with normal colon. (c) The expression levels of p53β and Δ133p53 in colon carcinomas were analyzed according to tumour stage. The data of normal colon and adenoma samples are same as those in (b). The expression levels (mean and s.d.) in adenomas, stage I (n=8), stage II (n=11) and stage III (n=10) carcinomas are shown as relative log 2 values to normal colon (defined as 0, not shown). *, p<0.05.
Figure 17:
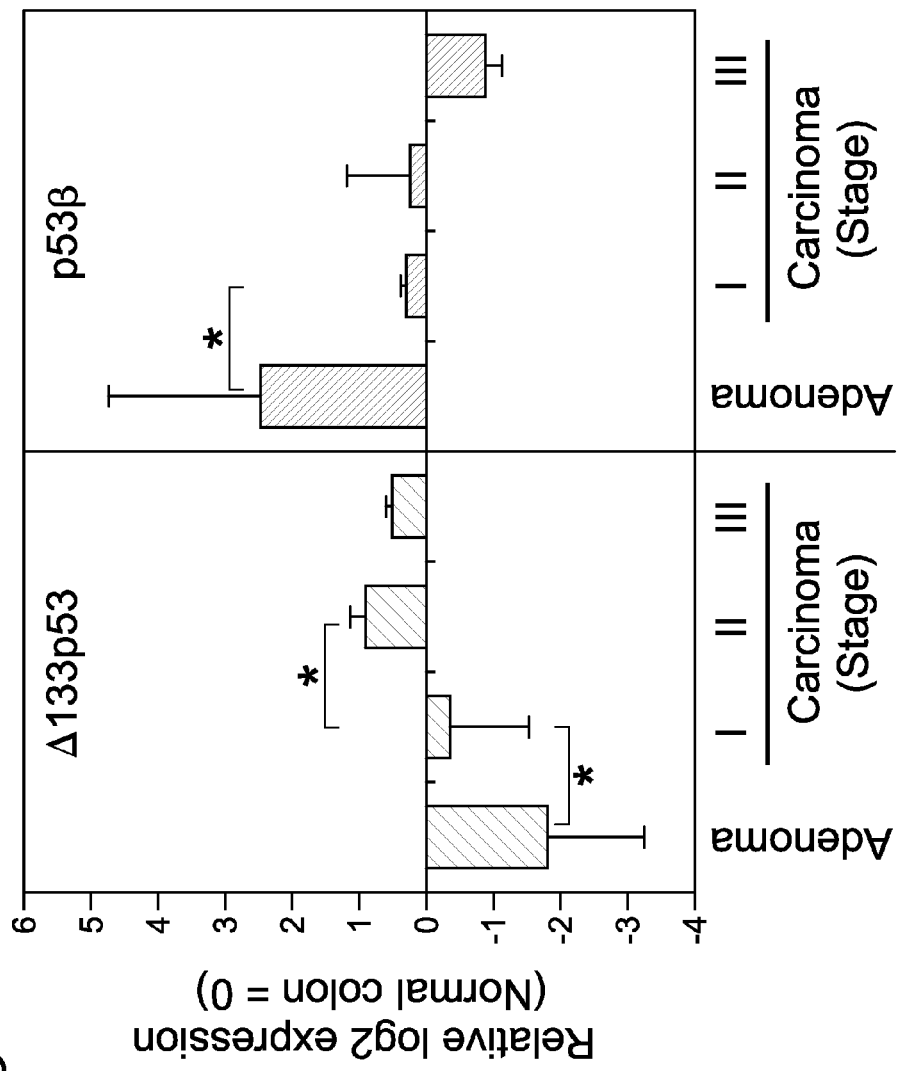
Figure 31:
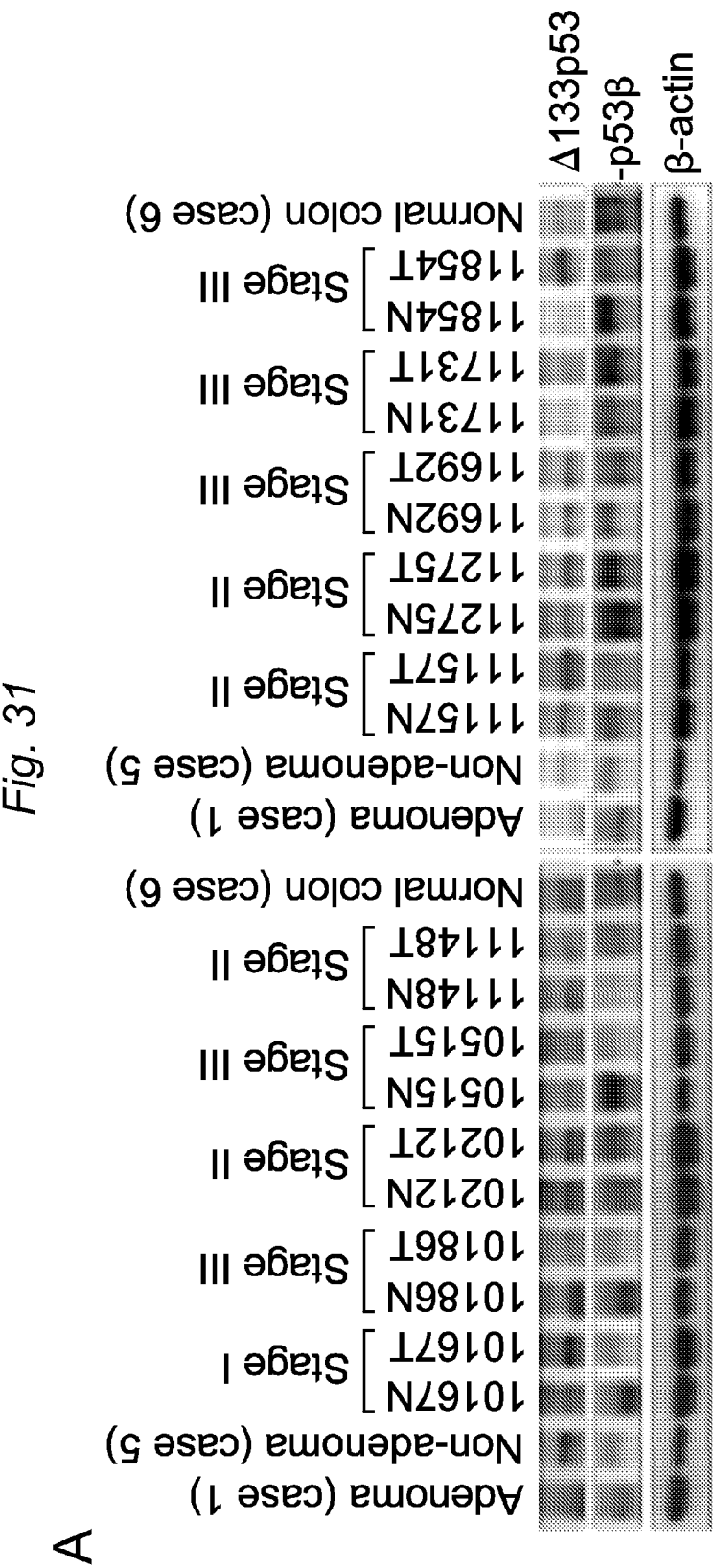
FIG. 31. Immunoblot analyses of Δ133p53 and p53β expression in matched colon carcinoma and non-carcinoma tissues. Twenty-nine cases of matched colon carcinoma (T) and non-carcinoma (N) tissues (Table 3) were examined for Δ133p53 and p53β. β-actin was the control for normalization. Each of the six SDS-PAGE gels included 5 pairs of carcinoma/non-carcinoma tissues, as well as the same set of normal colon, non-adenoma and adenoma samples, which allowed quantitative comparisons among different blots and different histopathological types, as in FIGS. 17b and c. One case (12375) was duplicated. The data shown in FIG. 17b (Non-ca and Ca), 4c (Carcinoma, stage I, II and III) and FIG. 32 were from the quantitative analysis of these results.
Figure 31:
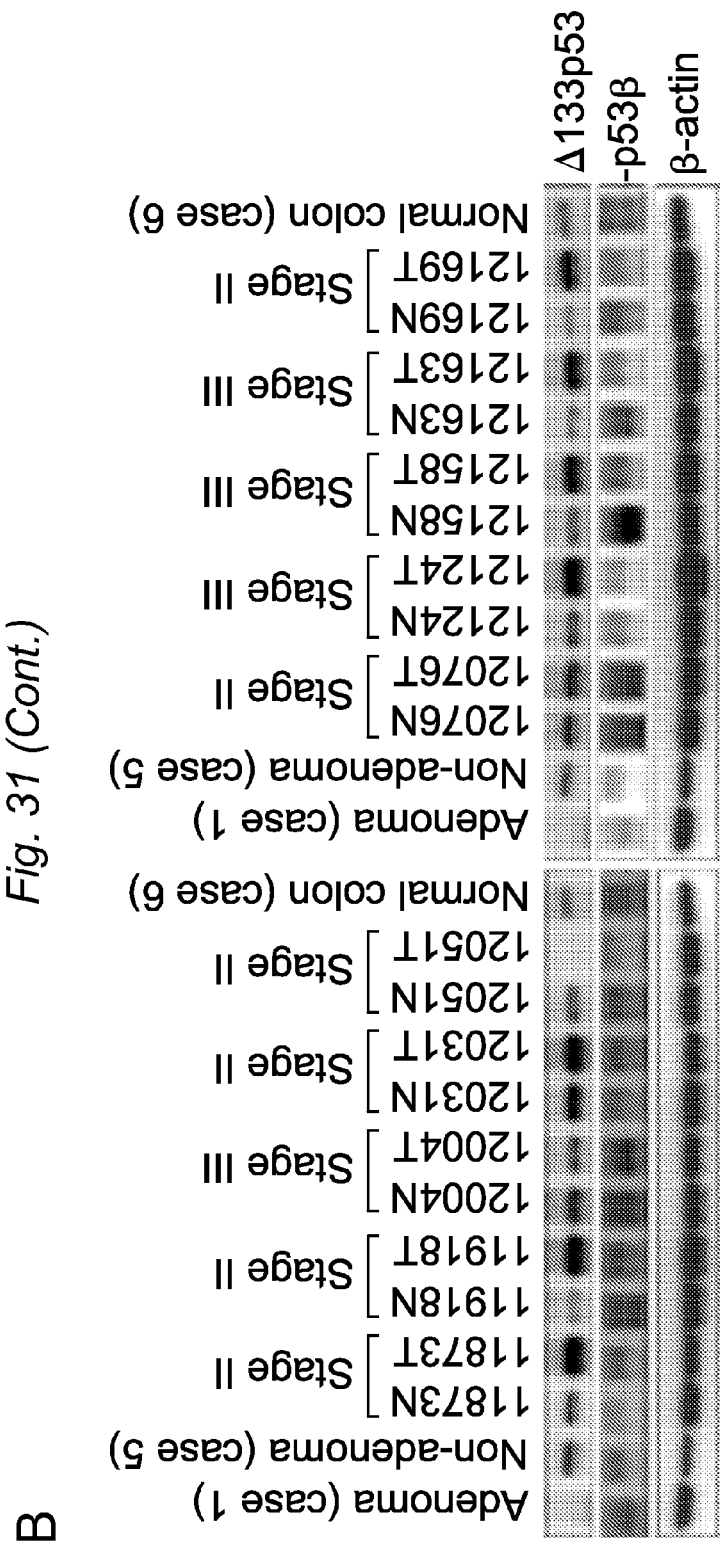
Figure 31:
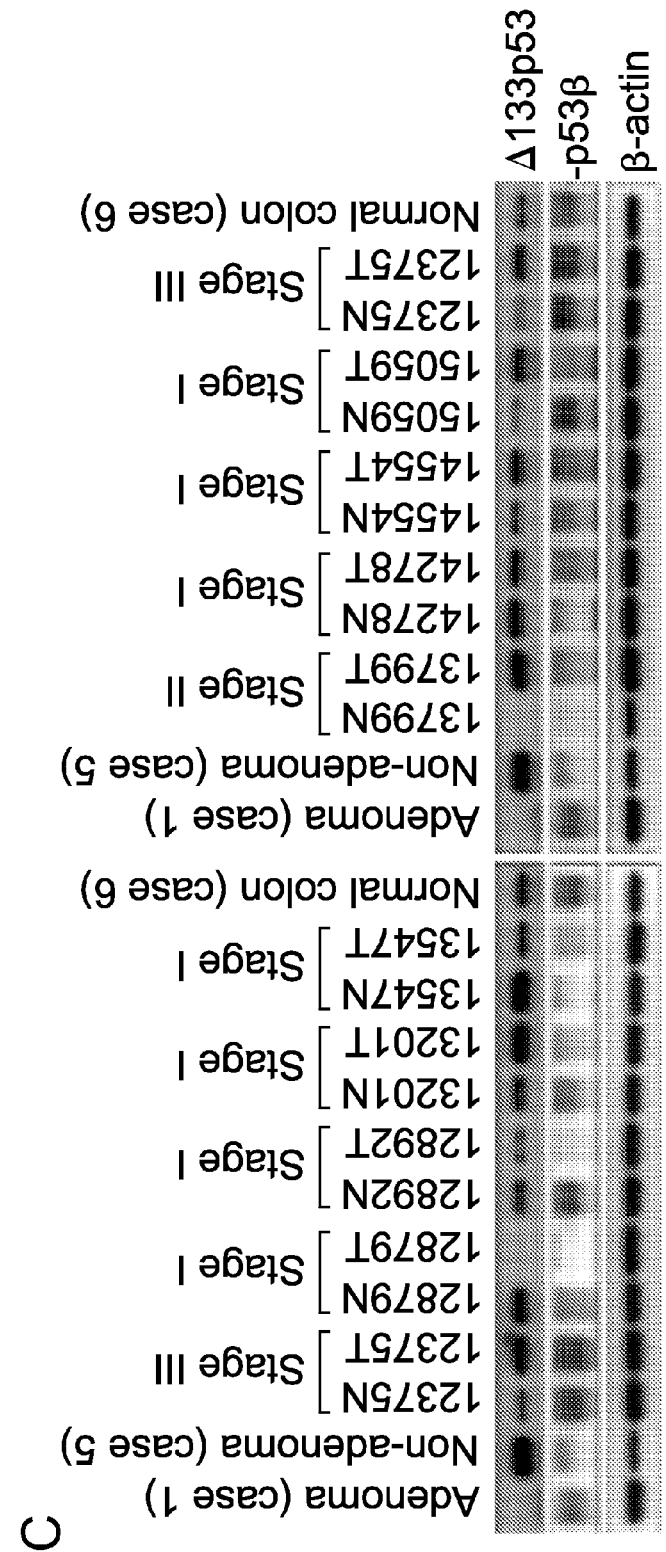
Figure 32:
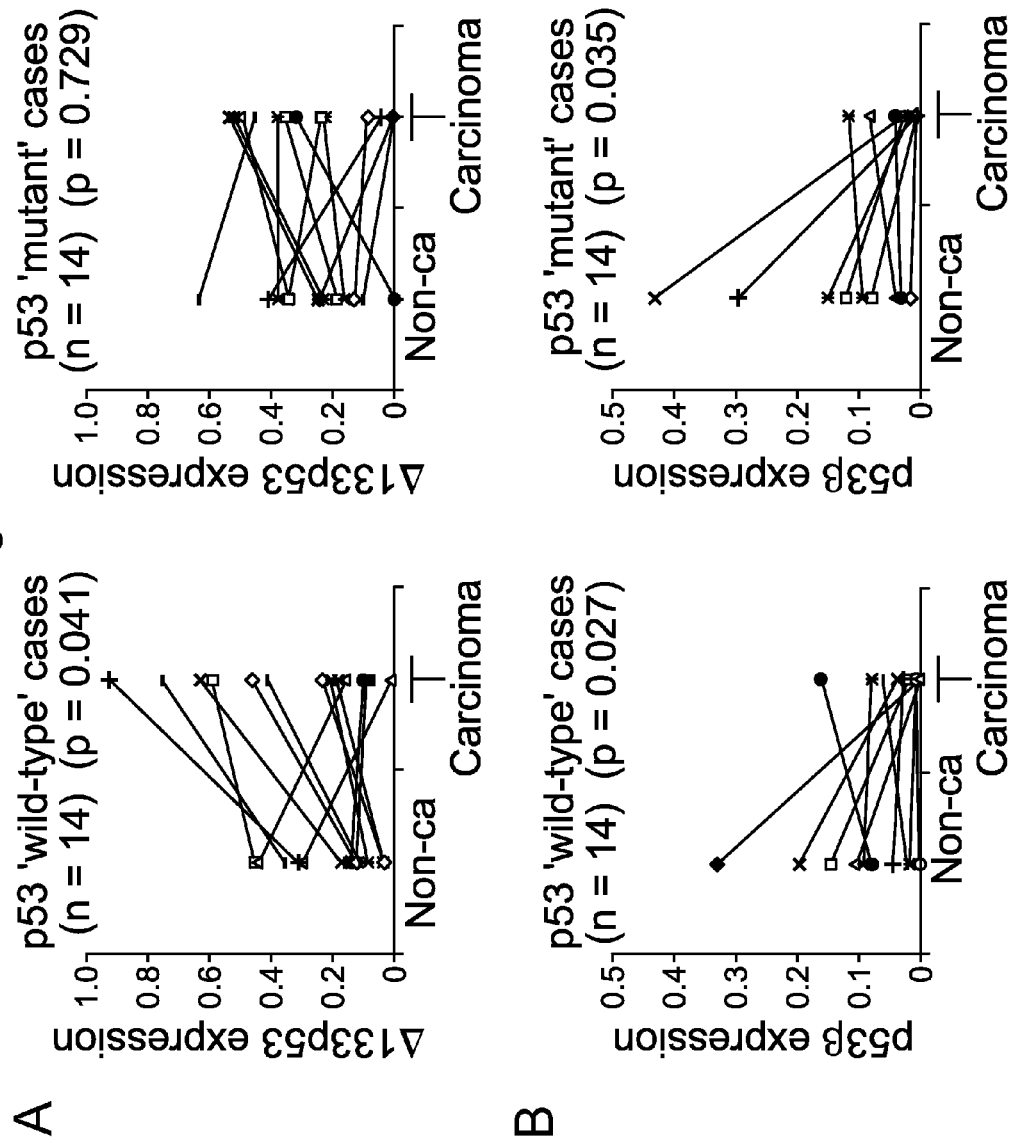
FIG. 32. Paired t-test analyses of Δ133p53 and p53β expression in p53 'wild-type' versus 'mutant' cases of colon carcinomas. Twenty-eight cases of colon carcinomas were divided into two subgroups assumedly with 'wild-type' or 'mutant' p53, based on the immunohistochemical staining of p53 and MDM2 (Costa et al., *The Journal of pathology* 176, 45-53 (1995); Nenutil et al., *The Journal of pathology* 207, 251-259 (2005)). In each subgroup, the expression levels of Δ133p53 (a) and p53β (b) were compared between non-carcinoma (Non-ca) and carcinoma tissues by paired t-test. The vertical axes are the expression levels normalized with β-actin. The p-values are in the parentheses. The p53 'wild-type' carcinomas, but not "mutant" carcinomas, expressed significantly higher levels of Δ133p53. p53β was significantly less abundant in carcinoma tissues in both subgroups because of the marked increase in non-carcinoma tissues (FIG. 17b). The actual values in each of the 28 cases are shown in Table 4.

We also examined 29 cases of matched colon carcinoma and non-carcinoma tissues (Table 3) for Δ133p53 and p53β expression (FIG. 31). In contrast to colon adenomas, colon carcinoma tissues (FIG. 17b, bars "Ca") did not show the senescence-associated p53 isoform expression signature, with Δ133p53 increased and p53β decreased back to similar levels to those in normal colons and non-adenoma tissues. Although the adjacent non-carcinoma tissues (FIG. 17b, bars "Non-ca") expressed significantly elevated levels of p53β, which were comparable to those in adenomas, its biological importance is currently unknown. When colon carcinoma tissues were compared among clinical stages (FIG. 17c), the stage I carcinomas already failed to maintain the characteristics of adenomas, showing significantly increased Δ133p53 and decreased p53β compared with adenomas. These results show that the senescence-associated p53 isoform expression signature becomes lost at an early stage of malignant progression. The loss of the signature may signal an escape from the senescence barrier observed in premalignant tumors[1, 3, 8, 20, 23]. A further significant increase in Δ133p53 from stage I to II and a further decrease in p53β from stage II to III (FIG. 17c) suggest that these p53 isoforms may also play a role during stage progression of colon carcinoma. The biological relevance of the function of Δ133p53 in colon carcinogenesis was further substantiated by the subgroup analysis based on p53 status, which was determined by p53 and MDM2 immunohistochemical staining of carcinoma tissues[24, 25] (Table 3). The expression levels of Δ133p53 were significantly higher in carcinoma tissues than in non-carcinoma tissues in the cases assumed to be 'wild-type' p53, but not in the cases assumed to be 'mutant' p53 (FIG. 32 and Table 4). This finding agrees with our in vitro data showing the ability of Δ133p53 to inhibit the wild-type p53 function (FIGS. 15a, 15e, 16e, and 25) and suggests that elevated levels of Δ133p53 may replace p53 gene mutations in colon carcinogenesis in vivo.

Figure 33:
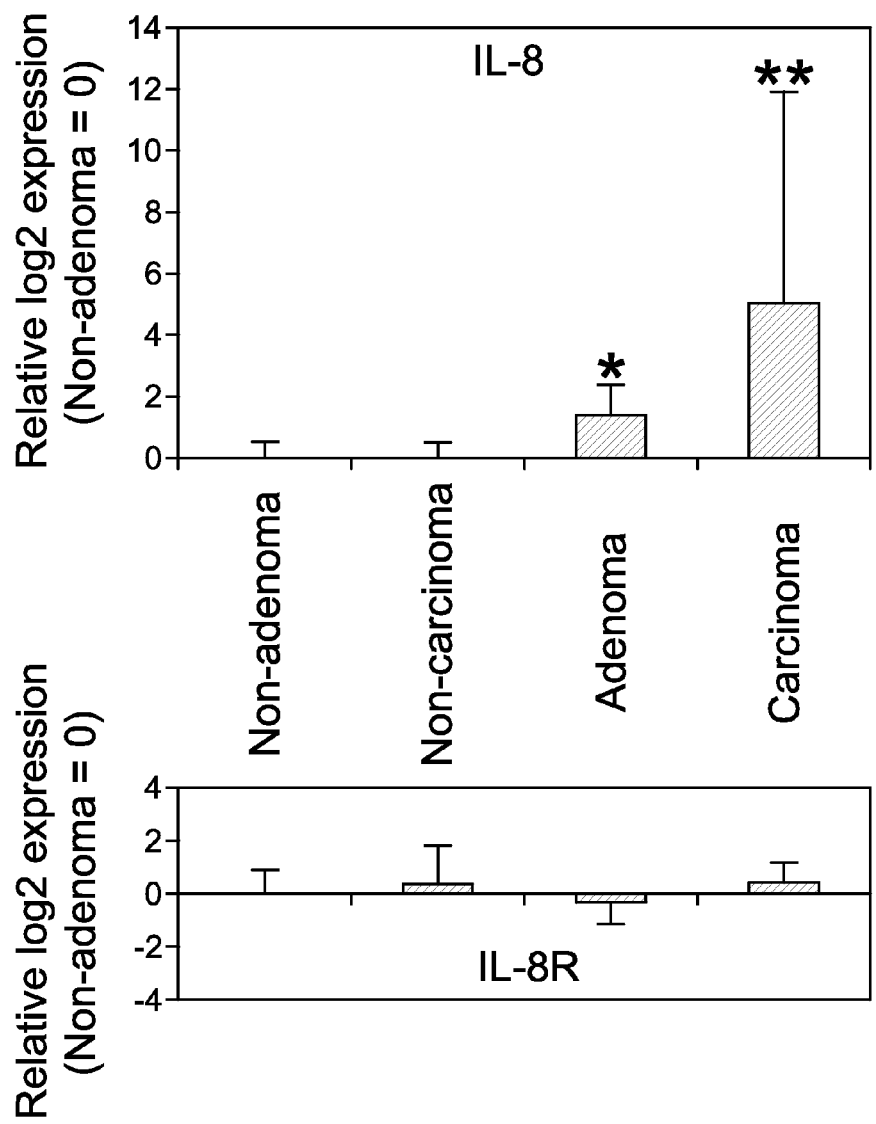
FIG. 33. IL-8 and IL-8R expression in colon adenoma and carcinoma tissues. The mRNA expression levels of IL-8 (upper panel) and IL-8R (lower panel) were examined by qRT-PCR in 8 matched pairs of non-adenoma and adenoma tissues (Table 2) and 29 matched pairs of non-carcinoma and carcinoma tissues (Table 3). The expression levels (mean and s.d.) in non-carcinoma, adenoma and carcinoma samples are shown as relative log 2 values to non-adenoma (defined as 0). *, p<0.05 compared with non-adenoma or non-carcinoma. **, p<0.001 compared with non-adenoma or non-carcinoma.

Interleukin-8 (IL-8) was upregulated in colon adenoma tissues compared with adjacent non-adenoma tissues (FIG. 33), reproducing the recent report by Kuilman et al.[8] and further confirming the senescence status of the adenoma samples used in this study. The IL-8 signalling pathway seems involved in both replicative senescence and oncogene-induced senescence in a p53-dependent manner[23], which are observed in colon adenomas[8, 18-20]. However, it is unlikely that this cytokine-mediated mechanism for senescence primarily regulates, or is regulated by, the senescence-associated expression signature of the p53 isoforms, because colon carcinoma tissues without such signature (FIG. 17b) still expressed remarkably increased levels of IL-8 (FIG. 33), as reported[26], and adjacent non-carcinoma tissues with elevated p53β (FIG. 17b) showed no increase in IL-8 expression (FIG. 33). Considering our in vitro observation that the senescence-associated p53 isoform expression signature is specific to replicative senescence (FIG. 14a and FIG. 20), a full malignant conversion from adenoma to carcinoma may require overcoming the senescence barriers by both p53 isoform-dependent (i.e., replicative senescence) and -independent (e.g., oncogene-induced, interleukin-regulated senescence) mechanisms.

In summary, based on the expression and functional analyses of endogenous proteins, which were supported by the overexpression experiments, this study provides the first evidence for the physiological regulation of replicative cellular senescence by natural p53 isoforms. The data also establish the endogenous miR-34a as a downstream effector in the p53-regulated signalling pathways to cellular senescence.

Figure 38:
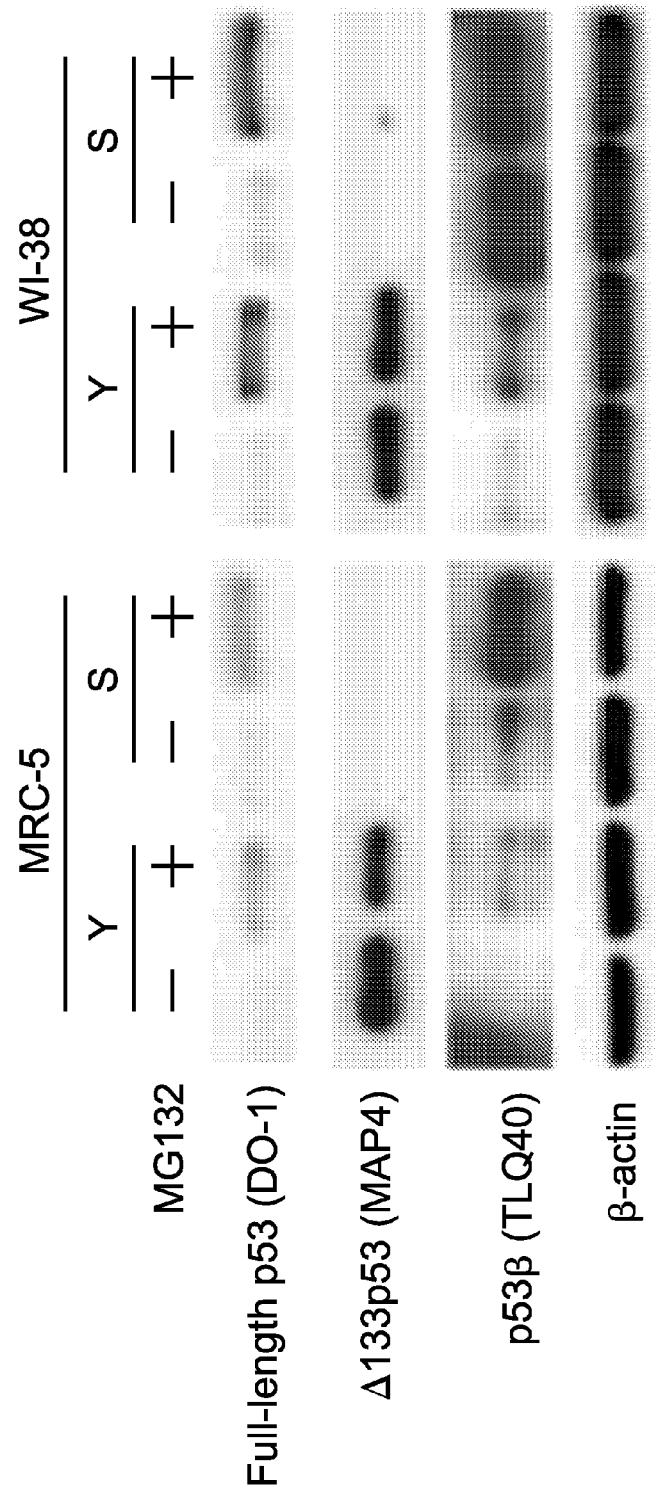
FIG. 38. Δ133p53 is not subject to proteasomal degradation. Early-passage (Y) and replicatively senescent (S) MRC-5 and WI-38 (the same set of cells as in FIG. 14a) were maintained in the presence (+) or absence (−) of 15 μM of the proteasome inhibitor MG-132 for 8 hrs and examined in immunoblot.

Although the exact mechanism of the senescence-associated p53 isoform switching still remains to be determined, we found that Δ133p53, unlike p53β and full-length p53, does not accumulate in the presence of a proteasome inhibitor MG-132 (FIG. 38), suggesting that the differential dynamics of protein turnover may be involved. With the evidence for the p53 isoform switching in vivo in both healthy and disease conditions, this study provides a new p53-based, senescence-mediated strategy for the manipulation of ageing and carcinogenesis processes in vivo[2-4].

Methods

Retroviral vector transduction was performed essentially as previously described[14,29]. Transfection of siRNA and antisense oligonucleotides used the Lipofectamine RNAiMAX transfection reagent (Invitrogen, Carlsbad, Calif.). Cell proliferation, replicative lifespan and senescence assays were essentially as described[14, 20, 29]. For immunoblot analyses, preparation of protein lysates from cells or tissues, SDS-PAGE, transfer to nitrocellulose or PVDF membranes, incubation with antibodies, and signal detection followed the standard procedures. The real-time qRT-PCR for miR-34a expression was performed using the reagents from Applied Biosystems (Foster City, Calif.), essentially as described[6]. To analyze telomeric 3' overhang and telomere length, in-gel Southern hybridization with $^{32}$P-labeled [CCCTAA]$_4$ (SEQ ID NO:5) oligonucleotide, under native and denatured conditions, was performed as previously described[14]. Fluorescence-activated cell sorting (FACS) of human CD8$^+$ T lymphocytes based on CD28 and CD57 expression patterns essentially followed Brenchley et al.[8]. Human tissues were collected with approval from the Institutional Review Board of the National Institutes of Health.

Cells. CC1, a human choriocarcinoma cell line expressing Δ133p53 due to the genomic rearrangement deleting the exons 2, 3 and 4[31], was a gift from Dr. Mitsuo Oshimura (Tottori University, Japan). Normal human fibroblast strains (MRC-5 and WI-38), H1299, RKO and 293T were obtained from American Type Culture Collection (Manassas, Va.). hTERT/NHF, an hTERT (human telomerase reverse transcriptase)-immortalized human fibroblast cell line, was previously described[32]. MDAH041 was kindly provided by Dr. Michael Tainsky (Case Western Reserve University, Cleveland, Ohio). The treatment with Nutlin-3A was as described[20].

Plasmid constructs. To generate the retroviral expression vectors of human p53 isoforms, full-length p53, FLAG-tagged p53β and FLAG-tagged Δ133p53 were PCR-amplified using pSVrp53, pSVp53β and pSVDNp53[5], respectively, as the templates, and then inserted into Not I and Eco RI sites of pQCXIN vector (BD Biosciences, San Jose, Calif.). These constructs were verified by DNA sequencing. The retroviral construct pLPC-Myc-TRF2$^{\Delta B\Delta M}$ was a gift from Dr. Titia de Lange (Rockefeller University, NY). The retroviral expression vector for H-RasV 12 was a gift from Dr. Manuel Serrano (Spanish National Cancer Research Center). The shRNA knockdown vectors targeting p53 and POT1 were previously described[14].

Retroviral vector transduction. The retroviral constructs were transfected into *Phoenix* packaging cells (Orbigen, Inc., San Diego, Calif.) using Lipofectamin 2000 (Invitrogen, Carlsbad, Calif.). Vector supernatants were collected 48 h after transfection and used to infect cells in the presence of 8 μg/ml polybrene (Sigma-Aldrich, St. Louis, Mo.). Two days after infection, the infected cells were selected with 600 μg/ml of G418 (Sigma-Aldrich), 2 μg/ml of puromycin (Sigma-Aldrich) or 1 mg/ml of zeocin (Invitrogen).

siRNA and antisense oligonucleotides. A stealth siRNA duplex oligoribonucleotide targeting Δ133p53 mRNA (Δ133si-1, 5'-UGU UCA CUU GUG CCC UGA CUU UCA A-3', SEQ ID NO:1), its scrambled control, and a standard siRNA duplex oligoribonucleotide targeting Δ133p53 mRNA (Δ133si-2, 5'-CUU GUG CCC UGA CUU UCA A[dT][dT]-3', SEQ ID NO:2) were synthesized at Invitrogen. The following antisense 2'-O-methyl oligonucleotides were purchased from Integrated DNA Technologies (Coralville, Iowa): 5'-AAC AAC CAG CUA AGA CAC UGC CA-3', SEQ ID NO:3, for inhibiting miR-34a; and 5'-AAG GCA AGC UGA CCC UGA AGU-3', SEQ ID NO:4, as a control, which is complementary to the enhanced green fluorescence protein (EGFP). The siRNA and antisense oligonucleotides were transfected at the final concentration of 12 nM and 40 nM, respectively, into MRC-5 and WI-38 fibroblasts by using the Lipofectamine RNAiMAX transfection reagent (Invitrogen) according to the supplier's protocol.

Cell proliferation assay, senescence-associated-β-galactosidase (SA-β-gal) staining, examination of cellular replicative lifespan, and bromo-deoxyuridine (BrdU) incorporation assay. For cell proliferation assay, $2.4 \times 10^5$ cells per well were plated into 12-well plates. These cells were collected and counted daily for a week using a hematocytometer. The experiments were performed at least twice and data at each time point were in triplicate. For examining cellular replicative lifespan, the number of cells was counted at each passage, and the number of population doublings (PDL) achieved between passages was determined by $\log_2$ (number of cells obtained/number of cells inoculated)[29]. SA-β-gal staining was performed as previously described'. For BrdU incorporation assay, cells were incubated with 10 μM of BrdU for 24 h. The incorporated BrdU was detected using an anti-BrdU monoclonal antibody (Amersham Biosciences) and observed with a fluorescent microscope. The nuclei were counterstained with 4',6-diamidino-2-phenylindole (DAPI).

Immunoblot analysis. Cells or tissues were lysed in RIPA buffer [10 mM Tris-HCl, pH 7.5, 150 mM NaCl, 0.1% SDS, 0.1% sodium deoxycholate, 1 mM EDTA, 1% NP-40, complete protease inhibitors (Roche, Indianapolis, Ind.), phosphatase inhibitor cocktail 1 and 2 (Sigma-Aldrich)]. SDS-PAGE, transfer to nitrocellulose or PVDF membranes (Bio-Rad, Hercules, Calif.), incubation with antibodies, and signal detection followed the standard procedures using ECL detection (Amersham Biosciences, Piscataway, N.J.) or SuperSignal West Dura Extended Duration system (Pierce Biotechnology, Rockford, Ill.). The quantitative analysis of the immunoblot data was performed using the ImageJ 1.40 g software (http://rsb.info.nih.gov/ij/).

Antibodies. A polyclonal antibody specifically recognizing Δ133p53 (MAP4) was raised at Moravian Biotechnology (Brno, Czech Republic) in rabbits injected with a mixture of peptides, MFCQLAKTC (SEQ ID NO:13) and FCQLAKTCP (SEQ ID NO:14), which were synthesized as Multiple Antigenic Peptide by Dr. G. Bloomberg (University of Bristol, Bristol, UK). The other primary antibodies used were: TLQ40[5] for p53β; CM1[5], DO-12 (Millipore, Billerica, Mass.) and DO-1 (Santa Cruz Biotechnology, Santa Cruz, Calif.) for p53; EA10 (Carbiochem, San Diego, Calif.) for $p21^{WAF1}$; SMP14 (Santa Cruz Biotechnology) for MDM2; 8G10 (Cell Signaling Technology, Danvers, Mass.) for caspase-3; M2 monoclonal antibody (Sigma-Aldrich) for FLAG tag; AC-15 (Sigma-Aldrich) for β-actin; MAB3450 (Chemicon International, Temecula, Calif.) for HP1-γ; anti-phospho-p53 (Ser15) (Cell Signaling Technology); anti-PARP (Cell Signaling Technology); FITC-conjugated anti-CD8 (BD Biosciences, Franklin Lakes, N.J.); APC-conjugated anti-CD28 (BD Biosciences); and PE-conjugated anti-CD57 (Abcam, Cambridge, Mass.). Horseradish peroxidase-conjugated goat anti-mouse or anti-rabbit antibodies (Santa Cruz Biotechnology) were used as secondary antibodies in immunoblots.

Real-time qRT-PCR for quantification of microRNA expression. RNA samples were prepared by using Trizol (Invitrogen). Reverse transcriptase reactions were performed using TaqMan microRNA reverse transcription kit (Applied Biosystems, cat. no. 4366596) and a miR-34a-specific primer. The TaqMan microRNA assay kit for miR-34a (Applied Biosystems, cat. no. 4373278) was used according to the supplier's protocol. Real-time PCR reactions were performed in triplicate. RNU66 (Applied Biosystems, cat. no. 4373382) was used as a control for quantification. Based on Ct (cycle threshold) values from miR-34a and RNU66 detections, normalized miR-34a expression was calculated by using the ΔΔCt method according to the supplier's protocol (protocol no. 4310255B and User Bulletin no. 4303859B at http://www.appliedbiosystems.com/index.cfm).

Real-time qRT-PCR for PAI-1, IL-8 and IL-8R. For quantitative measurement of PAI-1 mRNA, the SYBR Green PCR Master Mix (Applied Biosystems) was used with the following primers: 5'-CTC CTG GTT CTG CCC AAG T-3' and 5'-CAG GTT CTC TAG GGG CTT CC-3' (SEQ ID NO:16) for PAI-1; and 5'-TTC TGG CCT GGA GGC TAT C-3' (SEQ ID NO:17) and 5'-TCA GGA AAT TTG ACT TTC CAT TC-3' (SEQ ID NO:18) for β-2 microglobulin as an internal control. For IL-8 and IL-8R, the Taqman Universal PCR Master Mix (Applied Biosystems) was used with the following sets of probe and primers purchased from Applied Biosystems: IL-8 (catalog #4331182, Hs00174103 ml); IL-8R (catalog #4331182, Hs001174304 ml); and 18S endogenous control (catalog #4319413).

Measurement of telomeric 3' overhang and telomere length. Genomic DNA samples were digested with Hinf I and electrophoresed through 0.7% agarose gel. After drying at 25° C. for 30 min in a Bio-Rad model 583 gel dryer, the gel was hybridized with $^{32}$P-labeled $[CCCTAA]_4$ (SEQ ID NO:5) oligonucleotide as previously described[34], followed by washing and signal detection using the Typhoon 8600 system (Molecular Dynamics, Sunnyvale, Calif.). The amounts of telomeric 3' overhangs, normalized with loaded DNA amounts detected with ethidium bromide (EtBr) staining of the gel, were quantitated by using the ImageQuant version 5.2 software (Molecular Dynamics). After alkali denaturation (0.5M NaOH/1.5M NaCl) and neutralization (2.5M NaCl/0.5M Tris-HCl, pH 7.5) of the dried gel, the same procedures were repeated to examine telomere length, which was indicated as a peak TRF (terminal restriction fragment) length.

T Cell Sorting. Peripheral blood mononuclear cells from healthy volunteers were isolated using Histopaque-1077 (Sigma-Aldrich). The anti-CD57 (PE-conjugated), anti-CD8 (FITC-conjugated) and anti-CD28 (APC-conjugated) monoclonal antibodies were added at saturating concentrations and the cells were incubated for 30 min on ice and washed twice, then resuspended at a concentration of $20 \times 10^6$ cells/ml. The following cell fractions were sorted using the FACSAria cell-sorting system (BD Biosciences): CD8+/CD28+/CD57−, CD8+/CD28+/CD57+, CD8+/CD28−/CD57−, CD8+/CD28−/CD57+. Viability (>99%) was determined by gating on 7-AAD-negative cells. Purities of sorted cells were determined on at least 5000 events and analyzed using FlowJo software (Tree Star, Ashland, Oreg.).

Human colon tissues. Normal colon tissues were obtained from immediate autopsy at Baltimore area hospitals in Maryland[26]. Pairs of colon adenoma and adjacent non-adenoma tissues were from the University of Maryland Medical Center and the Cooperative Human Tissue Network. All tissues were flash frozen immediately after resected. Tumor histopathology was classified according to the World Health Organization Classification of Tumor system. This study was approved by the Institutional Review Board of the National Institutes of Health. Tables 1 and 2 summarize information on tissue samples used in this study.

REFERENCES

1. Bartkova, J. et al. Oncogene-induced senescence is part of the tumorigenesis barrier imposed by DNA damage checkpoints. *Nature* 444, 633-637 (2006).
2. Collado, M., Blasco, M. A. & Serrano, M. Cellular senescence in cancer and aging. *Cell* 130, 223-233 (2007).
3. Xue, W. et al. Senescence and tumour clearance is triggered by p53 restoration in murine liver carcinomas. *Nature* 445, 656-660 (2007).
4. Campisi, J. & d'Adda di Fagagna, F. Cellular senescence: when bad things happen to good cells. *Nat. Rev. Mol. Cell. Biol.* 8, 729-740 (2007).
5. Bourdon, J. C. et al. p53 isoforms can regulate p53 transcriptional activity. *Genes Dev.* 19, 2122-2137 (2005).
6. He, L. et al. A microRNA component of the p53 tumour suppressor network. *Nature* 447, 1130-1134 (2007).
7. Kortlever, R. M., Higgins, P. J. & Bernards, R. Plasminogen activator inhibitor-1 is a critical downstream target of p53 in the induction of replicative senescence. *Nat. Cell Biol.* 8, 877-884 (2006).
8. Brenchley, J. M. et al. Expression of CD57 defines replicative senescence and antigen-induced apoptotic death of CD8+ T cells. *Blood* 101, 2711-2720 (2003).
9. Effros, R. B., Dagarag, M., Spaulding, C. & Man, J. The role of CD8+ T-cell replicative senescence in human aging. *Immunol. Rev.* 205, 147-157 (2005).
10. Collado, M. et al. Tumour biology: senescence in premalignant tumours. *Nature* 436, 642 (2005).
11. Zhang, X., Sejas, D. P., Qiu, Y., Williams, D. A. & Pang, Q. Inflammatory ROS promote and cooperate with the Fanconi anemia mutation for hematopoietic senescence. *J. Cell Science* 120, 1572-1583 (2007).
12. Dai, C. Y. et al. p16(INK4a) expression begins early in human colon neoplasia and correlates inversely with markers of cell proliferation. Gastroenterology 119, 929-942 (2000).
13. Kuilman, T. et al. Oncogene-induced senescence relayed by an interleukin-dependent inflammatory network. *Cell* 133, 1019-1031 (2008).
14. Yang, Q. et al. Functional diversity of human protection of telomeres 1 isoforms in telomere protection and cellular senescence. *Cancer Res.* 67, 11677-11686 (2007).
15. van Steensel, B., Smogorzewska, A. & de Lange, T. TRF2 protects human telomeres from end-to-end fusions. *Cell* 92, 401-413 (1998).
16. Brown, J. P., Wei, W. & Sedivy, J. M. Bypass of senescence after disruption of p21CIP1/WAF1 gene in normal diploid human fibroblasts. *Science* 277, 831-834 (1997).
17. Herbig, U., Jobling, W. A., Chen, B. P., Chen, D. J. & Sedivy, J. M. Telomere shortening triggers senescence of human cells through a pathway involving ATM, p53, and p21(CIP1), but not p16(INK4a). *Mol. Cell.* 14, 501-513 (2004).
18. Chang, T. C. et al. Transactivation of miR-34a by p53 Broadly Influences Gene Expression and Promotes Apoptosis. *Mol. Cell.* 26, 745-752 (2007).
19. Tazawa, H., Tsuchiya, N., Izumiya, M. & Nakagama, H. Tumor-suppressive miR-34a induces senescence-like growth arrest through modulation of the E2F pathway in human colon cancer cells. *Proc. Natl. Acad. Sci. USA.* 104, 15472-15477 (2007).
20. Kumamoto, K. et al. Nutlin-3a activates p53 to both down-regulate inhibitor of growth 2 and up-regulate mir-34a, mir-34b, and mir-34c expression, and induce senescence. *Cancer Res.* 68, 3193-3203 (2008).
21. Rozan, L. M. & El-Deiry, W. S. p53 downstream target genes and tumor suppression: a classical view in evolution. *Cell Death Differ.* 14, 3-9 (2007).
22. Yin, Y., Tainsky, M. A., Bischoff, F. Z., Strong, L. C. & Wahl, G. M. Wild-type p53 restores cell cycle control and inhibits gene amplification in cells with mutant p53 alleles. *Cell* 70, 937-948 (1992).
23. Harley, C. B., Vaziri, H., Counter, C. M. & Allsopp, R. C. The telomere hypothesis of cellular aging. *Exp. Gerontol.* 27, 375-382 (1992).
24. Hastie, N. D. et al. Telomere reduction in human colorectal carcinoma and with ageing. *Nature* 346, 866-868 (1990).
25. O'Sullivan, J. et al. Telomere length in the colon declines with age: a relation to colorectal cancer? *Cancer Epidemiol. Biomarkers Prev.* 15, 573-577 (2006).
26. Autrup, H., Harris, C. C., Schwartz, R. D., Trump, B. F. & Smith, L. Metabolism of 1,2-dimethylhydrazine by cultured human colon. *Carcinogenesis* 1, 375-380 (1980).
27. Krishnamurthy, J. et al. Ink4a/Arf expression is a biomarker of aging. *J. Clin. Invest.* 114, 1299-1307 (2004).
28. Tada, T. et al. Reduced p16 expression correlates with lymphatic invasion in colorectal cancers. *Hepato-gastroenterology* 50, 1756-1760 (2003).
29. Michishita, E., Park, J. Y., Burneskis, J. M., Barrett, J. C. & Horikawa, I. Evolutionarily Conserved and Nonconserved Cellular Localizations and Functions of Human SIRT Proteins. *Mol. Biol. Cell* 16, 4623-4635 (2005).
30. Ghosh, A., Stewart, D. & Matlashewski, G. Regulation of human p53 activity and cell localization by alternative splicing. *Mol. Cell. Biol.* 24, 7987-7997 (2004).
31. Horikawa, I., Suzuki, M. & Oshimura, M. An aminoterminally truncated p53 protein expressed in a human choriocarcinoma cell line, CC1. *Hum. Mol. Genet.* 4, 313-314 (1995).
32. Sengupta, S. et al. BLM helicase-dependent transport of p53 to sites of stalled DNA replication forks modulates homologous recombination. *EMBO J.* 22, 1210-1222 (2003).
33. Dimri, G. P. et al. A biomarker that identifies senescent human cells in culture and in aging skin in vivo. *Proc. Natl. Acad. Sci. USA.* 92, 9363-9367 (1995).
34. Miura, N. et al. Progressive telomere shortening and telomerase reactivation during hepatocellular carcinogenesis. *Cancer Genet. Cytogenet.* 93, 56-62 (1997).

TABLE 1

Information on normal colon samples obtained from immediate autopsy.

| Case number | Age | Gender | Cause of death |
|---|---|---|---|
| 1 | 25 | Male | Gun shot wound |
| 2 | 29 | Male | Gun shot wound |
| 3 | 16 | Female | Motor vehicle accident (closed head injury) |

TABLE 1-continued

Information on normal colon samples obtained from immediate autopsy.

| Case number | Age | Gender | Cause of death |
|---|---|---|---|
| 4 | 28 | Male | Closed head injury |
| 5 | 23 | Female | Motor vehicle accident (closed head injury) |
| 6 | 52 | Female | Motor vehicle accident |
| 7 | 76 | Female | Motor vehicle accident |
| 8 | 20 | Male | Motor vehicle accident |
| 9 | 19 | Female | Gun shot wound |

TABLE 2

Information on 8 pairs of colon adenoma and non-adenoma samples.

| Case number | Age | Gender | Histopathological diagnosis |
|---|---|---|---|
| 1 | 62 | Male | Tubular adenoma |
| 2 | 64 | Female | Tubular adenoma |
| 3 | 87 | Female | Villous adenoma |
| 4 | 84 | Male | Villous adenoma |
| 5 | 78 | Male | Tubulovillous adenoma |
| 6 | 66 | Male | Tubular adenoma |
| 7 | 79 | Male | Villous adenoma |
| 8 | 78 | Male | Tubulovillous adenoma |

Information on 29 cases of colon carcinoma.

| Case* | Gender | Age | Stage | p53 status** | Histology | Survival (months) |
|---|---|---|---|---|---|---|
| 10167 | M | 55 | I | wild-type | adeno | 154.0 T |
| 10186 | F | 70 | III | mutant | adeno | 153.6 |
| 10212 | F | 66 | II | wild-type | mucinous | 144.3 |
| 10515 | M | 53 | III | mutant | adeno | 61.9 |
| 11148 | F | 63 | II | wild-type | adeno | 26.6 |
| 11157 | M | 73 | II | wild-type | adeno | 130.1 |
| 11275 | M | 76 | II | wild-type | adeno | 90.4 |
| 11692 | M | 58 | III | mutant | adeno | 112.3 |
| 11731 | M | 59 | III | mutant | mucinous | 18.4 |
| 11854 | M | 70 | III | n.d.*** | adeno | 18.8 |
| 11873 | M | 72 | II | wild-type | adeno | 106.7 |
| 11918 | M | 59 | II | wild-type | adeno | 104.9 |
| 12004 | M | 51 | III | mutant | adeno | 102.1 |
| 12031 | M | 50 | II | wild-type | adeno | 38.9 |
| 12051 | M | 70 | II | wild-type | adeno | 79.1 |
| 12076 | M | 76 | II | mutant | adeno | 100.1 |
| 12124 | M | 60 | III | mutant | adeno | 98.6 |
| 12158 | M | 70 | III | mutant | mucinous | 97.9 |
| 12163 | M | 53 | III | mutant | adeno | 5.9 |
| 12169 | M | 67 | II | wild-type | adeno | 97.2 |
| 12375 | F | 66 | III | wild-type | mucinous | 92.2 |
| 12879 | M | 80 | I | mutant | adeno | 62.8 |
| 12892 | M | 69 | I | wild-type | adeno | 79.9 |
| 13201 | F | 60 | I | mutant | adeno | 72.4 |
| 13547 | M | 69 | I | wild-type | adeno | 55.5 |
| 13799 | M | 44 | II | mutant | adeno | 61.2 |
| 14278 | M | 59 | I | mutant | mucinous | 54.1 |
| 14554 | M | 59 | I | mutant | adeno | 50.1 |
| 15059 | M | 67 | I | wild-type | adeno | 43.5 |

*Schetter et al., JAMA 299: 425-436, 2008.
**p53 status was assumed to be 'wild-type' or 'mutant' by immunohistochemical staining of p53 and MDM2 (Costa et al., J. Pathol. 176: 45-53, 1995; Nenutil et al., J. Pathol. 207: 251-259, 2005).
***Not determined.

TABLE 4

Δ133p53 and p53β expression in p53 'wild-type' and 'mutant' cases of colon carcinoma.

| Case- | Δ133p53 Non-ca | Carcinoma | p53 Non-ca | Carcinoma |
|---|---|---|---|---|
| p53 'wild-type' | | | | |
| 10167 - I | 0.0285 | 0.2276 | 0.3299 | 0.0004 |
| 12892 - I | 0.1376 | 0.0892 | 0.1432 | 0.0190 |
| 13547 - I | 0.4270 | 0.1329 | 0.0146 | 0.0604 |
| 15059 - I | 0.0816 | 0.2083 | 0.1946 | 0.0398 |
| 10212 - II | 0.0302 | 0.1529 | 0.1059 | 0.0004 |
| 11148 - II | 0.1458 | 0.1007 | 0.0809 | 0.1596 |
| 11157 - II | 0.3105 | 0.9175 | 0.0453 | 0.0269 |
| 11275 - II | 0.0986 | 0.4103 | 0.0968 | 0.0061 |
| 11873 - II | 0.3557 | 0.7519 | 0.0035 | 0.0077 |
| 11918 - II | 0.0885 | 0.4647 | 0.1268 | 0.0004 |
| 12031 - II | 0.4436 | 0.5961 | 0.0004 | 0.0004 |
| 12051 - II | 0.2774 | 0.0122 | 0.1213 | 0.0004 |
| 12169 - II | 0.1679 | 0.6279 | 0.0154 | 0.0004 |
| 12375 - III | 0.0944 | 0.2126 | 0.0897 | 0.0776 |
| p53 'mutant' | | | | |
| 12879 - I | 0.2421 | 0.0033 | 0.0156 | 0.0004 |
| 13201 - I | 0.1807 | 0.3560 | 0.1160 | 0.0304 |
| 14278 - I | 0.3356 | 0.2461 | 0.0395 | 0.0779 |
| 14554 - I | 0.1567 | 0.2301 | 0.1226 | 0.0485 |
| 12076 - II | 0.3786 | 0.3812 | 0.0932 | 0.1173 |
| 13799 - II | 0.0033 | 0.3206 | 0.0308 | 0.0388 |
| 10186 - III | 0.4134 | 0.0396 | 0.3002 | 0.0004 |
| 10515 - III | 0.1003 | 0.0033 | 0.0215 | 0.0004 |
| 11692 - III | 0.6377 | 0.4520 | 0.0146 | 0.0088 |
| 11731 - III | 0.1403 | 0.0737 | 0.0166 | 0.0249 |
| 12004 - III | 0.2440 | 0.2460 | 0.0744 | 0.0019 |
| 12124 - III | 0.3315 | 0.5139 | 0.0769 | 0.0004 |
| 12158 - III | 0.2558 | 0.5446 | 0.4359 | 0.0267 |
| 12163 - III | 0.2377 | 0.5289 | 0.1512 | 0.0004 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Sequence Listing

SEQ ID NO: 1
5'-UGU UCA CUU GUG CCC UGA CUU UCA A-3'

SEQ ID NO: 2
5'-CUU GUG CCC UGA CUU UCA A[dT][dT]-3'

SEQ ID NO: 3
5'-AAC AAC CAG CUA AGA CAC UGC CA-3'

SEQ ID NO: 4
5'-AAG GCA AGC UGA CCC UGA AGU-3'

What is claimed is:

1. A method of promoting senescence in a cell, the method comprising the step of contacting the cell with an agent that inhibits the function or expression of Δ133p53, but not wildtype p53 expression, thereby promoting cell senescence.

2. The method of claim 1, wherein the agent is an siRNA or a ribozyme.

3. The method of claim 2, wherein the siRNA is an shRNA.

4. The method of claim 1, wherein the cell is a cancer cell.

5. A method of inhibiting cancer cell growth by promoting cell senescence, the method comprising the step of contacting the cancer cell with an agent that inhibits the function or expression of Δ133p53, thereby inhibiting cancer cell growth.

6. The method of claim 5, wherein the agent is an siRNA or ribozyme.

7. A method of treating cancer by promoting cell senescence, the method comprising the step of contacting cancer cells with an agent that inhibits the function or expression of Δ133p53, but not wildtype p53 expression, thereby treating cancer.

8. The method of claim 7, wherein the agent is an siRNA or ribozyme.

* * * * *